(12) United States Patent
Emmanuel et al.

(10) Patent No.: US 9,487,793 B2
(45) Date of Patent: Nov. 8, 2016

(54) POLYNUCLEOTIDES, POLYPEPTIDES AND METHODS FOR INCREASING OIL CONTENT, GROWTH RATE AND BIOMASS OF PLANTS

(71) Applicant: Evogene Ltd., Rechovot (IL)

(72) Inventors: Eyal Emmanuel, Rechovot (IL); Gil Ronen, Emek Hefer (IL); Noa Savir, Givat Brenner (IL)

(73) Assignee: Evogene Ltd., Rehovot (IL)

( * ) Notice: Subject to any disclaimer, the term of this patent is extended or adjusted under 35 U.S.C. 154(b) by 418 days.

(21) Appl. No.: 13/936,226

(22) Filed: Jul. 8, 2013

(65) Prior Publication Data

US 2013/0291223 A1    Oct. 31, 2013

Related U.S. Application Data

(63) Continuation of application No. 12/594,853, filed as application No. PCT/IL2008/000489 on Apr. 9, 2008, now Pat. No. 8,513,488.

(60) Provisional application No. 60/907,568, filed on Apr. 9, 2007.

(51) Int. Cl.
  *C12N 15/82* (2006.01)
  *C07K 14/415* (2006.01)

(52) U.S. Cl.
  CPC .......... *C12N 15/8247* (2013.01); *C07K 14/415* (2013.01); *C12N 15/8261* (2013.01)

(58) Field of Classification Search
  None
  See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 4,943,674 A | 7/1990 | Houck et al. |
| 4,945,050 A | 7/1990 | Sanford et al. |
| 5,011,771 A | 4/1991 | Bellet et al. |
| 5,187,267 A | 2/1993 | Comai et al. |
| 5,192,659 A | 3/1993 | Simons |
| 5,268,463 A | 12/1993 | Jefferson |
| 5,272,057 A | 12/1993 | Smulson et al. |
| 5,281,521 A | 1/1994 | Trojanowski et al. |
| 5,296,462 A | 3/1994 | Thomashow |
| 5,316,931 A | 5/1994 | Donson et al. |
| 5,356,816 A | 10/1994 | Thomashow |
| 5,399,680 A | 3/1995 | Zhu et al. |
| 5,464,765 A | 11/1995 | Coffee et al. |
| 5,466,785 A | 11/1995 | De Framond |
| 5,495,070 A | 2/1996 | John |
| 5,504,200 A | 4/1996 | Hall et al. |
| 5,521,708 A | 5/1996 | Beretta |
| 5,569,597 A | 10/1996 | Grimsley et al. |
| 5,597,718 A | 1/1997 | John et al. |
| 5,604,121 A | 2/1997 | Hilder et al. |
| 5,608,142 A | 3/1997 | Barton et al. |
| 5,608,144 A | 3/1997 | Baden et al. |
| 5,608,149 A | 3/1997 | Barry et al. |
| 5,608,152 A | 3/1997 | Kridl et al. |
| 5,620,882 A | 4/1997 | John |
| 5,659,026 A | 8/1997 | Baszczynski et al. |
| 5,693,507 A | 12/1997 | Daniell et al. |
| 5,859,330 A | 1/1999 | Bestwick et al. |
| 5,880,100 A | 3/1999 | Ogiso et al. |
| 5,981,834 A | 11/1999 | John et al. |
| 6,080,914 A | 6/2000 | Conner |
| 6,084,153 A | 7/2000 | Good et al. |
| 6,313,375 B1 | 11/2001 | Jung et al. |
| 6,313,376 B1 | 11/2001 | Jung et al. |
| 6,359,196 B1 | 3/2002 | Lok et al. |

(Continued)

FOREIGN PATENT DOCUMENTS

| | | |
|---|---|---|
| AU | 2005229157 | 10/2005 |
| AU | 2005234725 | 12/2005 |

(Continued)

OTHER PUBLICATIONS

NCBI reference sequence: NM_125439.2, Jan. 10, 2002, shown in Office Action.*

(Continued)

*Primary Examiner* — Eileen B O Hara

(57) ABSTRACT

Provided are method of increasing oil content, growth rate, biomass, yield and/or vigor of a plant. The methods are effected by upregulating in the plant an expression level of a polypeptide comprising an amino acid sequence at least 90% homologous to the amino acid sequence selected from the group consisting of SEQ ID NOs: 199, 166-198, 200-221, 229-307, 311-330, 351-353, 355-361, 363-364, 366-368, 218, 222-228, 308-310, 350, 354, 362, 365, 523-649, 786-920, 1047 and 1048. Also provided are polynucleotides, nucleic acid constructs, polypeptides and transgenic plants expressing same which can be used to increase oil content, growth rate, biomass, yield and/or vigor of a plant and produce oil.

16 Claims, 3 Drawing Sheets

(56) References Cited

U.S. PATENT DOCUMENTS

| | | | |
|---|---|---|---|
| 6,392,122 | B1 | 5/2002 | Clendennen et al. |
| 6,403,862 | B1 | 6/2002 | Jiao et al. |
| 6,472,588 | B1 | 10/2002 | Haigler et al. |
| 6,670,528 | B1 | 12/2003 | Shinozaki et al. |
| 6,700,038 | B1 * | 3/2004 | Dasgputa .......... C12N 15/8203 435/320.1 |
| 6,720,477 | B2 | 4/2004 | Da Costa e Silva et al. |
| 7,214,786 | B2 | 5/2007 | Kovalic et al. |
| 7,554,007 | B2 | 6/2009 | Ronen et al. |
| 7,812,218 | B2 | 10/2010 | Ronen et al. |
| 7,910,800 | B2 | 3/2011 | Karchi et al. |
| 8,049,069 | B2 | 11/2011 | Wu et al. |
| 8,168,857 | B2 | 5/2012 | Ayal et al. |
| 8,426,682 | B2 | 4/2013 | Ronen et al. |
| 2002/0046419 | A1 | 4/2002 | Choo et al. |
| 2002/0049999 | A1 | 4/2002 | Allen et al. |
| 2002/0148007 | A1 | 10/2002 | Jiao et al. |
| 2002/0160378 | A1 | 10/2002 | Harper et al. |
| 2002/0170088 | A1 | 11/2002 | Wilkins |
| 2003/0005485 | A1 | 1/2003 | Ohlrogge et al. |
| 2003/0074697 | A1 | 4/2003 | Allen et al. |
| 2003/0084485 | A1 | 5/2003 | Zhu et al. |
| 2003/0162294 | A1 | 8/2003 | Verbruggen |
| 2003/0163839 | A1 | 8/2003 | Helentjaris et al. |
| 2003/0233670 | A1 | 12/2003 | Edgerton et al. |
| 2004/0006794 | A1 | 1/2004 | Wilkins |
| 2004/0019927 | A1 | 1/2004 | Sherman et al. |
| 2004/0031072 | A1 | 2/2004 | La Rosa et al. |
| 2004/0034888 | A1 | 2/2004 | Liu et al. |
| 2004/0123343 | A1 | 6/2004 | La Rosa et al. |
| 2004/0172684 | A1 | 9/2004 | Kovalic et al. |
| 2004/0181830 | A1 | 9/2004 | Kovalic et al. |
| 2004/0214272 | A1 | 10/2004 | La Rosa et al. |
| 2005/0108791 | A1 | 5/2005 | Edgerton |
| 2006/0048240 | A1 | 3/2006 | Alexandrov et al. |
| 2006/0101543 | A1 | 5/2006 | Somerville et al. |
| 2006/0107345 | A1 * | 5/2006 | Alexandrov .......... C07K 14/415 800/278 |
| 2006/0123505 | A1 | 6/2006 | Kikuchi et al. |
| 2006/0123516 | A1 | 6/2006 | Ronen et al. |
| 2006/0137043 | A1 | 6/2006 | Puzio et al. |
| 2006/0143729 | A1 | 6/2006 | Alexandrov et al. |
| 2006/0150283 | A1 | 7/2006 | Alexandrov et al. |
| 2006/0168684 | A1 | 7/2006 | Renz et al. |
| 2006/0174373 | A1 | 8/2006 | Gipmans et al. |
| 2006/0179511 | A1 | 8/2006 | Chomet et al. |
| 2006/0183137 | A1 | 8/2006 | Harper et al. |
| 2006/0195943 | A1 | 8/2006 | Feldmann et al. |
| 2006/0206961 | A1 | 9/2006 | Cirpus et al. |
| 2006/0260002 | A1 | 11/2006 | Ronen et al. |
| 2006/0288451 | A1 | 12/2006 | Val et al. |
| 2007/0006345 | A1 | 1/2007 | Alexandrov et al. |
| 2007/0006346 | A1 | 1/2007 | Alexandrov et al. |
| 2007/0044171 | A1 | 2/2007 | Kovalic et al. |
| 2007/0044172 | A1 | 2/2007 | Schneeberger et al. |
| 2007/0061916 | A1 | 3/2007 | Kovalic et al. |
| 2007/0124833 | A1 | 5/2007 | Abad et al. |
| 2007/0169219 | A1 | 7/2007 | Nadzan et al. |
| 2007/0214517 | A1 | 9/2007 | Alexandrov et al. |
| 2007/0261130 | A1 | 11/2007 | Lightner et al. |
| 2008/0072340 | A1 | 3/2008 | Troukhan et al. |
| 2008/0076179 | A1 | 3/2008 | Hartel et al. |
| 2008/0148432 | A1 | 6/2008 | Abad |
| 2008/0196120 | A1 | 8/2008 | Wu et al. |
| 2008/0301839 | A1 | 12/2008 | Ravanello |
| 2009/0089898 | A1 | 4/2009 | Karchi et al. |
| 2009/0093620 | A1 | 4/2009 | Kovalic et al. |
| 2009/0094717 | A1 | 4/2009 | Troukhan et al. |
| 2009/0126042 | A1 | 5/2009 | Ronen et al. |
| 2009/0260109 | A1 | 10/2009 | Ronen et al. |
| 2009/0293154 | A1 | 11/2009 | Yelin et al. |
| 2010/0037352 | A1 | 2/2010 | Alexandrov et al. |
| 2010/0154077 | A1 | 6/2010 | Emmanuel et al. |
| 2010/0319088 | A1 | 12/2010 | Ronen et al. |
| 2011/0080674 | A1 | 4/2011 | Durand |
| 2011/0214206 | A1 | 9/2011 | La Rosa et al. |
| 2012/0060234 | A1 | 3/2012 | Emmanuel et al. |
| 2012/0084885 | A1 | 4/2012 | Alexandrov et al. |
| 2012/0096587 | A1 | 4/2012 | Vinocur et al. |
| 2012/0180164 | A1 | 7/2012 | Ayal et al. |
| 2012/0222169 | A1 | 8/2012 | Ronen et al. |
| 2012/0297504 | A1 | 11/2012 | Granevitze et al. |
| 2013/0125258 | A1 | 5/2013 | Emmanuel et al. |
| 2013/0167265 | A1 | 6/2013 | Panik et al. |
| 2013/0219562 | A1 | 8/2013 | Ronen et al. |
| 2013/0239255 | A1 | 9/2013 | Ronen et al. |
| 2013/0276169 | A1 | 10/2013 | Poraty et al. |

FOREIGN PATENT DOCUMENTS

| | | |
|---|---|---|
| CN | 1823168 | 8/2006 |
| EP | 0834566 | 4/1998 |
| EP | 0905242 | 3/1999 |
| EP | 1033405 | 9/2000 |
| EP | 1225231 | 7/2002 |
| EP | 1586645 | 10/2005 |
| EP | 1945021 | 7/2008 |
| EP | 2154946 | 2/2010 |
| JP | 2005-052114 | 3/2005 |
| JP | 2005-185101 | 7/2005 |
| RU | 2350653 | 3/2009 |
| WO | WO 93/06710 | 4/1993 |
| WO | WO 93/07278 | 4/1993 |
| WO | WO 94/17194 | 8/1994 |
| WO | WO 95/08914 | 4/1995 |
| WO | WO 96/26639 | 9/1996 |
| WO | WO 96/40924 | 12/1996 |
| WO | WO 01/17333 | 3/2001 |
| WO | WO 01/40250 | 6/2001 |
| WO | WO 02/16655 | 2/2002 |
| WO | WO 02/45485 | 6/2002 |
| WO | WO 02/079403 | 10/2002 |
| WO | WO 02/090557 | 11/2002 |
| WO | WO 03/020025 | 3/2003 |
| WO | WO 03/087313 | 10/2003 |
| WO | WO 03/098186 | 11/2003 |
| WO | WO 2004/035798 | 4/2004 |
| WO | WO 2004/053055 | 6/2004 |
| WO | WO 2004/058963 | 7/2004 |
| WO | WO 2004/081173 | 9/2004 |
| WO | WO 2004/092367 | 10/2004 |
| WO | WO 2004/104162 | 12/2004 |
| WO | WO 2004/111183 | 12/2004 |
| WO | WO 2005/084331 | 9/2005 |
| WO | WO 2005/095614 | 10/2005 |
| WO | WO 2005/108422 | 11/2005 |
| WO | WO 2005/121364 | 12/2005 |
| WO | WO 2006/138012 | 12/2006 |
| WO | WO 2007/020638 | 2/2007 |
| WO | WO 2007/049275 | 5/2007 |
| WO | WO 2007/110314 | 10/2007 |
| WO | WO 2007/113237 | 10/2007 |
| WO | WO 2008/069878 | 6/2008 |
| WO | WO 2008/075364 | 6/2008 |
| WO | WO 2008/122980 | 10/2008 |
| WO | WO 2009/009142 | 1/2009 |
| WO | WO 2009/013750 | 1/2009 |
| WO | WO 2009/083958 | 7/2009 |
| WO | WO 2009/141824 | 11/2009 |
| WO | WO 2009/144311 | 12/2009 |
| WO | WO 2010/020941 | 2/2010 |
| WO | WO 2010/049897 | 5/2010 |
| WO | WO 2010/076756 | 7/2010 |
| WO | WO 2010/100595 | 9/2010 |
| WO | WO 2010/143138 | 12/2010 |
| WO | WO 2011/015985 | 2/2011 |
| WO | WO 2011/080674 | 7/2011 |
| WO | WO 2011/135527 | 11/2011 |
| WO | WO 2012/028993 | 3/2012 |
| WO | WO 2012/085862 | 6/2012 |
| WO | WO 2012/150598 | 11/2012 |
| WO | WO 2013/027223 | 2/2013 |
| WO | WO 2013/128448 | 9/2013 |
| WO | WO 2013/179211 | 12/2013 |

(56) References Cited

FOREIGN PATENT DOCUMENTS

| WO | WO 2014/188428 | 11/2014 |
|---|---|---|
| WO | WO 2015/029031 | 3/2015 |
| WO | WO 2015/181823 | 12/2015 |

OTHER PUBLICATIONS

UniProtKB—P38389 (SC61B_ARATH) Protein transport protein SEC61 subunit beta.*
Communication Pursuant to Article 94(3) EPC Dated Oct. 9, 2013 From the European Patent Office Re. Application No. 08869158.9.
Invitation to Pay Additional Fees Dated Oct. 16, 2013 From the International Searching Authority Re. Application No. PCT/IL2013/050725.
Office Action Dated Sep. 9, 2013 From the State Intellectual Property Office of the People's Republic of China Re. Application No. 200910217137.1 and Its Translation Into English.
Supplementary European Search Report and the European Search Opinion Dated Oct. 15, 2013 From the European Patent Office Re. Application No. 10840687.7.
Liu et al. "Plant Full Length Insert Polypeptide Seqid 64542", Database Geneseq [Online], XP002713973, Retrieved From EBI Accession No. GSP:ADY08727, Database Accession No. ADY08727, Apr. 21, 2005. Polypeptide Has 96.4% Identity to SEQ ID No. 653 and Is Used for the Same Purpose, Abstract, Sequence.
Paterson et al. "Sorghum Bicolor Chromosome 2, Whole Genome Shotgun Sequence", NCBI Database [Online], Retrieved From EBI Accession No. EMBL:CM000761, Database Accession No. CM000761, Jun. 24, 2009. Sequence.
Paterson et al. "SubName: Full=Putative Uncharacterized Protein Sb02g004350", Database UniProt [Online], XP002713972, Retrieved From EBI Accession No. UNIPROT:C5XB01, Database Accession No. C5XB01, Sep. 1, 2009. Polynucleotide and Polypeptide Molecules Fully Comprising the Present Molecules According to SEQ ID No. 166, 653, Abstract, Sequence.
Notice of Allowance Dated Nov. 15, 2013 From the US Patent and Trademark Office Re. U.S. Appl. No. 12/669,975.
Advisory Action Before the Filing of an Appeal Brief Dated Dec. 20, 2013 From the US Patent and Trademark Office Re. U.S. Appl. No. 12/834,106.
Applicant-Initiated Interview Summary Dated Dec. 18, 2013 From the US Patent and Trademark Office Re. U.S. Appl. No. 12/834,106.
Applicant-Initiated Interview Summary Dated Dec. 20, 2013 From the US Patent and Trademark Office Re. U.S. Appl. No. 13/125,047.
Requisition by the Examiner Dated Jul. 24, 2014 From the Canadian Intellectual Property Office Re. Application No. 2,683,143.
Communication Pursuant to Article 94(3) EPC Dated Aug. 2, 2013 From the European Patent Office Re. Application No. 10194223.3.
Examination Report Dated Jul. 9, 2013 From the Instituto Mexicano de la Propiedad Industrial Re. Application No. MX/a/2010/007169 and Its Translation Into English.
Examination Report Dated Jun. 26, 2013 From the Instituto Mexicano de la Propiedad Industrial Re. Application No. MX/a/2010/000975 and Its Translation Into English.
Official Action Dated Aug. 12, 2013 From the US Patent and Trademark Office Re. U.S. Appl. No. 12/834,106.
Substantive Examination Report Dated Jul. 31, 2013 From the Intellectual Property Office of the Philippines, Bureau of Patents Re. Application No. 1/2009/501930.
Advisory Action Before the Filing of an Appeal Brief Dated Nov. 19, 2013 From the US Patent and Trademark Office Re. U.S. Appl. No. 12/834,106.
International Search Report and the Written Opinion Dated Nov. 19, 2013 From the International Searching Authority Re. Application No. PCT/IL2013/050725.
Yu et al. "Cell Cycle Checkpoint Protein MAD2 Homolog [Zea Mays]", Database NCBI [Online], GenBank: AAD30555.1, GenBank Accession No. AAD30555, May 17, 1999.
Communication Pursuant to Article 94(3) EPC Dated Nov. 7, 2013 From the European Patent Office Re. Application No. 10748403.2.
Communication Pursuant to Rules 70(2) and 70a(2) EPC Dated Nov. 7, 2013 From the European Patent Office Re. Application No. 10840687.7.
Examination Report Dated Aug. 22, 2013 From the Instituto Mexicano de la Propiedad Industrial Re. Application No. MX/a/2011/009044 and Its Translation Into English.
Official Action Dated Oct. 29, 2013 From the US Patent and Trademark Office Re. U.S. Appl. No. 13/059,231.
Seki et al. "Monitoring the Expression Profiles of 7000 Arabidopsis Genes Under Drought, Cold and High-Salinity Stresses Using a Full-Length cDNA Microarray", The Plant Journal, 31(3): 279-292, 2002.
Tobias et al. "Structure of the Cinnamyl-Alcohol Dehydrogenase Gene Family in Rice and Promoter Activity of a Member Associated With Lignification", Planta, 220: 678-688, 2005.
Official Action Dated Jan. 9, 2014 From the US Patent and Trademark Office Re. U.S. Appl. No. 12/992,902.
Bork et al. "Go Hunting in Sequence Databases But Watch Out for the Traps", Trends in Genetics, TIG, 12(10): 425-427, Oct. 1996.
Doerks et al. "Protein Annotation: Detective Work for Function Prediction", Trends in Genetics, TTG, 14(6): 248-250, Jun. 1998.
Smith et al. "The Challenges of Genome Sequence Annotation or 'The Devil Is in the Details'", Nature Biotechnology, 15: 1222-1223, Nov. 1997.
Examination Report Dated Nov. 27, 2014 From the Ministry of Law and Human Rights of the Republic of Indonesia, Directorate General of the Intellectual Property Rights Re. Application No. W00200903085 and Its Translation Into English.
Communication Pursuant to Article 94(3) EPC Dated Dec. 8, 2008 From the European Patent Office Re. : Application No. 04734072.4.
International Preliminary Report on Patentability Dated Dec. 8, 2005 From the International Bureau of WIPO Re.: Application No. PCT/IL2004/000431.
International Preliminary Report on Patentability Dated Jan. 22, 2009 From the International Bureau of WIPO Re.: Application No. PCT/IL2006/001223.
Invitation to Pay Additional Fees Dated Feb. 7, 2008 From the International Searching Authority Re.: Application No. PCT/IL06/001223.
Invitation to Pay Additional Fees Dated Dec. 18, 2008 From the International Searching Authority Re.: Application No. PCT/IL08/01024.
Advisory Action Before the Filing of an Appeal Brief Dated Aug. 5, 2011 From the US Patent and Trademark Office Re. U.S. Appl. No. 12/083,978.
Advisory Action Before the Filing of an Appeal Brief Dated Aug. 29, 2012 From the US Patent and Trademark Office Re. U.S. Appl. No. 12/457,199.
Applicant-Initiated Interview Summary Dated Aug. 6, 2012 From the US Patent and Trademark Office Re. U.S. Appl. No. 12/669,975.
Communication Pursuant to Article 94(3) EPC Dated Apr. 3, 2012 From the European Patent Office Re.: Application No. 06766224.7.
Communication Pursuant to Article 94(3) EPC Dated Jan. 3, 2013 From the European Patent Office Re. Application No. 09807983.3.
Communication Pursuant to Article 94(3) EPC Dated Jul. 4, 2012 From the European Patent Office Re. Application No. 10194223.3.
Communication Pursuant to Article 94(3) EPC Dated Mar. 8, 2011 From the European Patent Office Re.: Application No. 06809784.9.
Communication Pursuant to Article 94(3) EPC Dated May 8, 2013 From the European Patent Office Re. Application No. 08776651.5.
Communication Pursuant to Article 94(3) EPC Dated Nov. 8, 2010 From the European Patent Office Re.: Application No. 04734072.4.
Communication Pursuant to Article 94(3) EPC Dated Sep. 9, 2009 From the European Patent Office Re.: Application No. 04734072.4.
Communication Pursuant to Article 94(3) EPC Dated May 12, 2010 From the European Patent Office Re.: Application No. 06766224.7.
Communication Pursuant to Article 94(3) EPC Dated Feb. 13, 2009 From the European Patent Office Re.: Application No. 05750089.4.
Communication Pursuant to Article 94(3) EPC DAted Jul. 13, 2012 From the European Patent Office Re. Application No. 11172514.9.

(56) References Cited

OTHER PUBLICATIONS

Communication Pursuant to Article 94(3) EPC Dated Feb. 14, 2012 From the European Patent Office Re.: Application No. 04734072.4.
Communication Pursuant to Article 94(3) EPC Dated Mar. 14, 2011 From the European Patent Office Re. Application No. 07849616.3.
Communication Pursuant to Article 94(3) EPC Dated Jun. 15, 2012 From the European Patent Office Re. Application No. 11154193.4.
Communication Pursuant to Article 94(3) EPC Dated 19, 2012 From the European Patent Office Re.: Application No. 04734072.4.
Communication Pursuant to Article 94(3) EPC Dated Nov. 19, 2010 From the European Patent Office Re.: Application No. 06809784.9.
Communication Pursuant to Article 94(3) EPC Dated Jun. 21, 2012 From the European Patent Office Re. Application No. 11154213.0.
Communication Pursuant to Article 94(3) EPC Dated Oct. 23, 2012 From the European Patent Office Re. Application No. 11154193.4.
Communication Pursuant to Article 94(3) EPC Dated Oct. 23, 2012 From the European Patent Office Re. Application No. 11154213.0.
Communication Pursuant to Article 94(3) EPC Dated Nov. 27, 2009 From the European Patent Office Re.: Application No. 06809784.9.
Communication Pursuant to Article 94(3) EPC Dated Jun. 29, 2011 From the European Patent Office Re. Application No. 08738191.9.
Communication Pursuant to Article 94(3) EPC Dated May 29, 2013 From the European Patent Office Re. Application No. 09823171.5.
Communication Pursuant to Rule 55 EPC Dated Mar. 16, 2012 From the European Patent Office Re. Application No. 11190921.4.
Communication Pursuant to Rule 58 EPC or Rule 159 EPC, Invitation to Remedy Deficiencies in the Application Documents Dated Jan. 19, 2012 From the European Patent Office Re. Application No. 11190922.2.
Communication Pursuant to Rule 69 EPC—Reminder Concerning Payment of the Designation Fee (Art. 79(2) EPC) and of the Examination Fee (Art. 94(1) EPC)—and Invitation Pursuant to Rule 70a(1) EPC Dated Jul. 18, 2011 From the European Patent Office Re. Application No. 11154193.4.
Communication Pursuant to Rule 69 EPC—Reminder Concerning Payment of the Designation Fee (Art. 79(2) EPC) and of the Examination Fee (Art. 94(1) EPC)—and Invitation Pursuant to Rule 70a(1) EPC Dated Jul. 25, 2011 From the European Patent Office Re. Application No. 11154213.0.
Communication Pursuant to Rule 70(2) EPC and Reference to Rule 39(1) EPC Dated Sep. 13, 2010 From the European Patent Office Re.: Application No. 09163033.5.
Communication Pursuant to Rules 70(2) and 70a(2) EPC and Reference to Rule 39(1) EPC Dated Dec. 5, 2011 From the European Patent Office Re. Application No. 10194223.3.
Communication Pursuant to Rules 70(2) and 70a(2) EPC and Reference to Rule 39(1) EPC Dated Nov. 7, 2011 From the European Patent Office Re. Application No. 11172514.9.
Communication Pursuant to Rules 70(2) and 70a(2) EPC Dated Mar. 5, 2013 From the European Patent Office Re. Application No. 10785834.2.
Communication Pursuant to Rules 70(2) and 70a(2) EPC Dated May 7, 2012 From the European Patent Office Re. Application No. 09823171.5.
Communication Pursuant to Rules 70(2) and 70a(2) EPC Dated Jan. 19, 2012 From the European Patent Office Re. Application No. 09807983.3.
Communication Pursuant to Rules 70(2) and 70a(2) EPC Dated Jul. 24, 2012 From the European Patent Office Re. Application No. 10748403.2.
Communication Pursuant to Rules 70(2) and 70a(2) EPC Dated May 24, 2011 From the European Patent Office Re. Application No. 09750276.9.
Communication Pursuant to Rules 70(2) and 70a(2) EPC Dated Aug. 30, 2010 From the European Patent Office Re. Application No. 08738191.9.
Communication Relating to the Results of the Partial International Search Dated Jul. 8, 2009 From the International Searching Authority Re.: Application No. PCT/IL2008/001657.
Communication Under Rule 71(3) EPC Dated Jun. 5, 2012 From the European Patent Office Re.: Application No. 06809784.9.
Communication Under Rule 71(3) EPC Dated Nov. 19, 2012 From the European Patent Office Re. Application No. 08738191.9.
Decision on Granting a Patent for Invention Dated Dec. 7, 2010 From the Rospatent, Federal State Institution, Federal Institute for Industrial Property of the Federal Service for Intellectual Property, Patents and Trademarks of the Russian Federation Re. Application No. 2008120395 and Its Translation Into English.
English Summary of Examination Results Dated Dec. 28, 2012 From the National Office of Intellectual Property (NOIP) of Vietnam Re. Application No. 1-2009-02358.
European Search Report and the European Search Opinion Dated Nov. 2, 2011 From the European Patent Office Re. Application No. 10194223.3.
European Search Report and the European Search Opinion Dated Oct. 6, 2011 From the European Patent Office Re. Application No. 11172514.9.
European Search Report and the European Search Opinion Dated Aug. 9, 2010 From the European Patent Office Re.: Application No. 09163033.5.
European Search Report and the European Search Opinion Dated Jun. 14, 2011 From the European Patent Office Re. Application No. 11154193.4.
European Search Report and the European Search Opinion Dated Jun. 21, 2011 From the European Patent Office Re. Application No. 11154213.0.
Examination Report Dated Aug. 1, 2011 From the Government of India, Patent Office Re.: Application No. 158/CHENP/2007.
Examination Report Dated Nov. 3, 2010 From the Government of India, Patent Office Re.: Application No. 158/CHENP/2007.
Examination Report Dated Jun. 6, 2012 From the Federal Service of Intellectual Property, Federal State Budget Institute, Federal Institute of Industrial Property of the Russian Federation Re. Application No. 2011113420 and Its Translation Into English.
Examination Report Dated Dec. 7, 2012 From the Instituto Mexicano de la Propiedad Industrial Re. Application No. MX/a/2011/003575 and Its Translation Into English.
Examination Report Dated Jun. 11, 2012 From the Instituto Mexicano de la Propiedad Industrial Re. Application No. MX/a/2011/007294 and Its Translation Into English.
Examination Report Dated Jun. 11, 2012 From the Instituto Mexicano de la Propiedad Industrial Re. Application No. MX/a/2011/007294 and Summary in English.
Examination Report Dated Mar. 13, 2013 From the Instituto Mexicano de la Propiedad Industrial Re. Application No. PA/a/2005/009380 and Its Summary in English.
Examination Report Dated Nov. 13, 2007 From the Government of India, Patent Office Re.: Application No. 3482/CHENP/2005.
Examination Report Dated Sep. 14, 2012 From the Australian Government IP Australia Re. Application No. 2007335706.
Examination Report Dated Oct. 15, 2012 From the Instituto Mexicano de la Propiedad Industrial Re. Application No. MX/a/2009/006660 and Its Translation Into English.
Examination Report Dated Aug. 16, 2012 From the Instituto Mexicano de la Propiedad Industrial Re. Application No. MX/a/2010/014097 and Its Translation Into English.
Examination Report Dated Feb. 17, 2010 From the Instituto Mexicano de la Propiedad Industrial Re. Application No. PA/a/2005/012565 and Its Summary in English.
Examination Report Dated Apr. 19, 2011 From the Instituto Mexicano de la Propiedad Industrial Re. Application No. MX/a/2008/002262 and Its Summary Into English.
Examination Report Dated Dec. 19, 2011 From the Federal Service of Intellectual Property, Federal State Budget Institute, Federal Institute of Industrial Property of the Russian Federation Re. Application No. 2011113420 and Its Translation Into English.
Examination Report Dated Sep. 22, 2010 From the Instituto Mexicano de la Propiedad Industrial Re. Application No. MX/a/2008/005280 and Its Summary Into English.
Examination Report Dated Mar. 23, 2013 From the Government of India, Patent Office, Intellectual Property Building Re. Application No. 2570/CHENP/2008.

(56) References Cited

OTHER PUBLICATIONS

Examination Report Dated Jun. 25, 2012 From the Instituto Mexicano de la Propiedad Industrial Re. Application No. MX/a/2011/003575 and Its Translation Into English.
Examination Report Dated May 25, 2011 From the Government of India, Patent Office Re.: Application No. 158/CHENP/2007.
Examiner's Report Dated Aug. 1, 2011 From the Australian Government, IP Australia Re. Application No. 2005234725.
Examiner's Report Dated Jan. 10, 2012 From the Australian Government, IP Australia Re. Application No. 2005234725.
Examiner's Report Dated Jan. 13, 2011 From the Australian Government, IP Australia Re.: Application No. 2005252469.
Examiner's Report Dated Jan. 13, 2012 From the Australian Government, IP Australia Re. Application No. 2011239323.
Examiner's Report Dated Mar. 15, 2012 From the Australian Government, IP Australia Re. Application No. 2011239323.
Examiner's Report Dated Dec. 17, 2009 From the Australian Government, IP Australia Re.: Application No. 2005252469.
Examiner's Report Dated Oct. 19, 2011 From the Australian Government, IP Australia Re. Application No. 2006281018.
Examiner's Report Dated Dec. 20, 2010 From the Australian Government, IP Australia Re. Application No. 2005234725.
Examiner's Report Dated Jul. 21, 2011 From the Australian Government, IP Australia Re. Application No. 2005234725.
Examiner's Report Dated Jun. 24, 2011 From the Australian Government, IP Australia Re. Application No. 2006281018.
Examiner's Report Dated Oct. 28, 2011 From the Australian Government, IP Australia Re. Application No. 2006307457.
Examiner's Report Dated Jun. 30, 2011 From the Australian Government, IP Australia Re. Application No. 2006307457.
Examiner's Report Dated Jan. 31, 2012 From the Australian Government, IP Australia Re. Application No. 2006281018.
Examiner's Report Dated Mar. 31, 2011 From the Australian Government, IP Australia Re.: Application No. 2005252469.
International Preliminary Report on Patentability Dated Dec. 1, 2011 From the International Bureau of WIPO Re. Application No. PCT/IL2008/000489.
International Preliminary Report on Patentability Dated Dec. 2, 2010 From the International Bureau of WIPO Re. Application No. PCT/IL2009/000508.
International Preliminary Report on Patentability Dated Mar. 3, 2011 From the International Bureau of WIPO Re.: Application No. PCT/IB2009/053633.
International Preliminary Report on Patentability Dated Feb. 4, 2010 From the International Bureau of WIPO Re.: Application No. PCT/IL2008/001024.
International Preliminary Report on Patentability Dated Jul. 4, 2013 From the International Bureau of WIPO Re. Application No. PCT/IB2011/055854.
International Preliminary Report on Patentability Dated Jul. 8, 2010 From the International Bureau of WIPO Re.: Application No. PCT/IL2008/001657.
International Preliminary Report on Patentability Dated Apr. 12, 2012 From the Interarntional Bureau of WIPO Re. Application No. PCT/IB2010/052545.
International Preliminary Report on Patentability Dated Jul. 12, 2012 From the International Bureau of WIPO Re. Application No. PCT/IB2010/056023.
International Preliminary Report on Patentability Dated May 12, 2011 From the International Bureau of WIPO Re. Application No. PCT/IB2009/054774.
International Preliminary Report on Patentability Dated Jan. 14, 2010 From the International Bureau of WIPO Re.: Application No. PCT/IL2008/000489.
International Preliminary Report on Patentability Dated Mar. 14, 2013 From the International Bureau of WIPO Re. Application No. PCT/IB2011/053697.
International Preliminary Report on Patentability Dated Sep. 15, 2011 From the International Bureau of WIPO Re. Application No. PCT/IB2010/050871.
International Preliminary Report on Patentability Dated Feb. 21, 2013 From the International Bureau of WIPO Re. Application No. PCT/IB2011/051843.
International Preliminary Report on Patentability Dated Jan. 21, 2010 From the International Bureau of WIPO Re.: Application No. PCT/IL2007/001590.
International Preliminary Report on Patentability Dated Jan. 22, 2009 From the International Bureau of WIPO Re.: Application No. PCT/IL2006/000947.
International Preliminary Report on Patentability Dated Mar. 29, 2007 From the International Bureau of WIPO Re.: Application No. PCT/IL2005/000627.
International Preliminary Report on Patentability Dated Jan. 30, 2007 From the International Bureau of WIPO Re.: Application No. PCT/IL05/00627.
International Search Report and the Written Opinion Dated Jun. 2, 2010 From the International Searching Authority Re. Application No. PCT/IB09/53633.
International Search Report and the Written Opinion Dated Jun. 2, 2010 From the International Searching Authority Re.: Application No. PCT/IB09/54774.
International Search Report and the Written Opinion Dated Aug. 6, 2012 From the International Searching Authority Re. Application No. PCT/IB2011/053697.
International Search Report and the Written Opinion Dated Dec. 6, 2011 From the International Searching Authority Re. Application No. PCT/IB2011/051843.
International Search Report and the Written Opinion Dated Sep. 6, 2012 From the International Searching Authority Re. Application No. PCT/IB2011/055854.
International Search Report and the Written Opinion Dated Jan. 7, 2013 From the International Searching Authority Re. Application No. PCT/IL2012/050154.
International Search Report and the Written Opinion Dated Sep. 7, 2010 From the International Searching Authority Re. Application No. PCT/IB10/50871.
International Search Report and the Written Opinion Dated Apr. 10, 2013 From the International Searching Authority Re. Application No. PCT/IL2012/050327.
International Search Report and the Written Opinion Dated May 12, 2013 From the International Searching Authority Re. Application No. PCT/IL2013/050172.
International Search Report and the Written Opinion Dated Mar. 16, 2012 From the International Searching Authority Re. Application No. PCT/IB2010/052545.
International Search Report and the Written Opinion Dated Feb. 17, 2010 From the International Searching Authority Re.: Application No. PCT/IL09/00508.
International Search Report and the Written Opinion Dated Aug. 22, 2011 From the International Searching Authority Re. Application No. PCT/IB2010/056023.
International Search Report and the Written Opinion Dated Nov. 24, 2008 From the International Searching Authority Re.: Application No. PCT/IL08/00489.
International Search Report and the Written Opinion Dated Jul. 29, 2008 From the International Searching Authority Re.: Application No. PCT/IL06/001223.
International Search Report and the Written Opinion Dated Oct. 30, 2009 From the International Searching Authority Re.: Application No. PCT/IL2008/001657.
International Search Report and the Written Opinion Dated Oct. 31, 2011 From the International Searching Authority Re.: Application No. PCT/IL08/00489.
International Search Report Dated Jul. 2, 2009 From the International Searching Authority Re.: Application No. PCT/IL07/01590.
International Search Report Dated Jan. 3, 2007 From the International Searching Authority Re.: Application No. PCT/IL2005/000627.
International Search Report Dated Mar. 4, 2009 From the International Searching Authority Re.: Application No. PCT/IL08/01024.
International Search Report Dated Nov. 4, 2005 From the International Searching Authority Re.: Application No. PCT/IL04/00431.

(56) References Cited

OTHER PUBLICATIONS

International Search Report Dated Aug. 27, 2008 From the International Searching Authority Re.: Application No. PCT/IL06/00947.
Invitation to Pay Additional Fees Dated Mar. 2, 2010 From the International Searching Authority Re.: Application No. PCT/IB09/53633.
Invitation to Pay Additional Fees Dated Apr. 8, 2013 From the International Searching Authority Re. Application No. PCT/IL2013/050172.
Invitation to Pay Additional Fees Dated May 8, 2012 From the International Searching Authority Re. Application No. PCT/IB2011/053697.
Invitation to Pay Additional Fees Dated Sep. 8, 2006 From the International Searching Authority Re.: Application No. PCT/IL05/00627.
Invitation to Pay Additional Fees Dated Jun. 9, 2011 From the International Searching Authority Re. Application No. PCT/IB2010/056023.
Invitation to Pay Additional Fees Dated Jun. 15, 2012 From the International Searching Authority Re. Application No. PCT/IB2011/055854.
Invitation to Pay Additional Fees Dated Oct. 17, 2012 From the International Searching Authority Re. Application No. PCT/IL2012/050154.
Invitation to Pay Additional Fees Dated Aug. 18, 2011 From the International Searching Authority Re.: Application No. PCT/IL08/00489.
Invitation to Pay Additional Fees Dated Nov. 19, 2009 From the International Searching Authority Re.: Application No. PCT/IL09/00508.
Invitation to Pay Additional Fees Dated Aug. 23, 2005 From the International Search Authority Re. Application No. PCT/IL2004/000431.
Invitation to Pay Additional Fees Dated Dec. 27, 2011 From the International Searching Authority Re. Application No. PCT/IB2010/052545.
Invitation to Pay Additional Fees Dated Dec. 31, 2012 From the International Searching Authority Re. Application No. PCT/IL2012/050327.
Notice of Allowance Dated Dec. 5, 2011 From the US Patent and Trademark Office Re. U.S. Appl. No. 12/448,359.
Notice of Allowance Dated Jan. 7, 2013 From the US Patent and Trademark Office Re. U.S. Appl. No. 12/457,199.
Notice of Allowance Dated Apr. 8, 2013 From the US Patent and Trademark Office Re. U.S. Appl. No. 12/594,853.
Notice of Allowance Dated Aug. 11, 2010 From the Instituto Mexicano de la Propriedad Industrial Re. Application No. PA/a/2005/012565.
Notice of Allowance Dated Apr. 16, 2010 From the US Patent and Trademark Office Re.: U.S. Appl. No. 11/629,411.
Notice of Allowance Dated Oct. 18, 2010 From the US Patent and Trademark Office Re.: U.S. Appl. No. 11/990,386.
Notice of Allowance Dated Nov. 19, 2012 From the US Patent and Trademark Office Re. U.S. Appl. No. 13/450,547.
Notice of Grant Dated Jan. 14, 2011 From the Instituto Mexicano de la Propricdad Industrial Re. Application No. MX/a/2008/005280.
Office Action Dated Apr. 1, 2013 From the State Intellectual Property Office of the People's Republic of China Re. Application No. 200880127757.X and Its Translation Into English.
Office Action Dated Jan. 2, 2012 From the Israel Patent Office Re. Application No. 206118 and Its Translation Into English.
Office Action Dated Feb. 3, 2011 From the Israel Patent Office Re.: Application No. 172135 and Its Translation Into English.
Office Action Dated Aug. 4, 2010 From the Israel Patent Office Re.: Application No. 172135 and Its Translation Into English.
Office Action Dated Jan. 9, 2009 From the State Intellectual Property Office of the People's Republic of China Re.: Application No. 200480020597.0.
Office Action Dated Nov. 11, 2010 From the Israel Patent Office Re. Application No. 206118 and Its Translation Into English.
Office Action Dated May 13, 2010 From the Israel Patent Office Re. Application No. 180022 and Its Translation Into English.
Office Action Dated Jun. 17, 2010 From the Israel Patent Office Re. Application No. 190918 and Its Translation Into English.
Office Action Dated Oct. 18, 2010 From the Israel Patent Office Re. Application No. 180022 and Its Translation Into English.
Office Action Dated Jun. 19, 2011 From the Israel Patent Office Re. Application No. 199391 and Its Translation Into English.
Office Action Dated Jun. 20, 2011 From the Israel Patent Office Re. Application No. 190918 and Its Translation Into English.
Office Action Dated Jan. 22, 2010 From the State Intellectual Property Office of the People's Republic of China Re.: Application No. 200580027481.4 and Its Translation Into English.
Office Action Dated Sep. 22, 2011 From the Israeli Patent Office Re. Application No. 201242 and Its Translation Into English.
Office Action Dated Jun. 25, 2012 From the State Intellectual Property Office of the People's Republic of China Re.: Application No. 200880109464.9 and Its Translation Into English.
Office Action Dated Apr. 27, 2009 From the Israeli Patent Office Re.: Application No. 172135 and Its Translation Into English.
Office Action Dated Jan. 31, 2010 From the Israel Patent Office Re.: Application No. 172135 and Its Translation Into English.
Office Letter Dated Jul. 7, 2008 From the Government of India, Patent Office Re.: Application No. 3482/CHENP/2005.
Official Action Dated May 1, 2009 From the US Patent and Trademark Office Re.: U.S. Appl. No. 11/629,411.
Official Action Dated Sep. 2, 2009 From the US Patent and Trademark Office Re.: U.S. Appl. No. 11/629,411.
Official Action Dated Feb. 8, 2013 From the US Patent and Trademark Office Re. U.S. Appl. No. 12/594,853.
Official Action Dated Jul. 8, 2011 From the US Patent and Trademark Office Re. U.S. Appl. No. 12/083,978.
Official Action Dated Jun. 8, 2010 From the US Patent and Trademark Office Re.: U.S. Appl. No. 11/629,411.
Official Action Dated May 8, 2013 From the US Patent and Trademark Office Re. U.S. Appl. No. 13/125,047.
Official Action Dated Apr. 10, 2012 From the US Patent and Trademark Office Re. U.S. Appl. No. 12/669,975.
Official Action Dated May 10, 2011 From the US Patent and Trademark Office Re. U.S. Appl. No. 12/457,199.
Official Action Dated Jun. 13, 2012 From the US Patent and Trademark Office Re. U.S. Appl. No. 12/594,853.
Official Action Dated May 14, 2012 From the US Patent and Trademark Office Re. U.S. Appl. No. 12/457,199.
Official Action Dated Feb. 15, 2011 From the US Patent and Trademark Office Re. U.S. Appl. No. 12/448,359.
Official Action Dated May 15, 2009 From the US Patent and Trademark Office Re.: U.S. Appl. No. 11/990,386.
Official Action Dated Jul. 17, 2012 From the US Patent and Trademark Office Re. U.S. Appl. No. 12/834,106.
Official Action Dated Aug. 18, 2010 From the US Patent and Trademark Office Re. U.S. Appl. No. 12/083,978.
Official Action Dated Dec. 18, 2012 From the US Patent and Trademark Office Re. U.S. Appl. No. 12/834,106.
Official Action Dated Jan. 18, 2013 From the US Patent and Trademark Office Re. U.S. Appl. No. 12/669,975.
Official Action Dated Oct. 18, 2007 From the US Patent and Trademark Office Re.: U.S. Appl. No. 11/284,236.
Official Action Dated Jun. 19, 2012 From the US Patent and Trademark Office Re. U.S. Appl. No. 13/450,547.
Official Action Dated Sep. 19, 2011 From the US Patent and Trademark Office Re. U.S. Appl. No. 12/810,855.
Official Action Dated May 20, 2013 From the US Patent and Trademark Office Re. U.S. Appl. No. 13/059,231.
Official Action Dated Dec. 21, 2011 From the US Patent and Trademark Office Re. U.S. Appl. No. 12/810,855.
Official Action Dated Aug. 22, 2011 From the US Patent and Trademark Office Re. U.S. Appl. No. 12/457,199.
Official Action Dated Oct. 22, 2009 From the US Patent and Trademark Office Re.: U.S. Appl. No. 11/990,386.

(56) References Cited

OTHER PUBLICATIONS

Official Action Dated Nov. 23, 2010 From the US Patent and Trademark Office Re. U.S. Appl. No. 12/083,978.
Official Action Dated Jun. 24, 2013 From the US Patent and Trademark Office Re. U.S. Appl. No. 12/992,902.
Official Action Dated Jul. 28, 2008 From the US Patent and Trademark Office Re.: U.S. Appl. No. 11/284,236.
Official Action Dated Apr. 29, 2011 From the US Patent and Trademark Office Re. U.S. Appl. No. 12/448,359.
Partial European Search Report Dated Jul. 12, 2011 From the European Patent Office Re. Application No. 10194223.3.
Partial European Search Report Dated Apr. 19, 2010 From the European Patent Office Re.: Application No. 09163033.5.
Patent Examination Report Dated Jan. 4, 2013 From the Australian Government, IP Australia Re. Application No. 2008344935.
Patent Examination Report Dated Dec. 12, 2012 From the Australian Government, IP Australia Re. Application No. 2008236316.
Patent Examination Report Dated Jun. 21, 2013 From the Australian Government, IP Australia Re. Application No. 2012241091.
Patent Examination Report Dated Jun. 27, 2013 From the Australian Government, IP Australia Re. Application No. 2012216482.
Patent Examination Report Dated May 31, 2013 From the Australian Government, IP Australia Re. Application No. 2008278654.
Requisition—Sequence Listing Dated May 8, 2013 From the Canadian Intellectual Property Office Re. Application No. 2,753,616.
Requisition by the Examiner Dated Feb. 2, 2012 From the Canadian Intellectual Property Office Re. Application No. 2,570,195.
Requisition by the Examiner Dated Oct. 3, 2012 From the Canadian Intellectual Property Office Re. Application No. 2,526,440.
Requisition by the Examiner Dated Apr. 11, 2013 From the Canadian Intellectual Property Office Re. Application No. 2,626,592.
Requisition by the Examiner Dated Feb. 12, 2013 From the Canadian Intellectual Property Office Re. Application No. 2,570,195.
Requisition by the Examiner Dated Jun. 15, 2011 From the Canadian Intellectual Property Office Re. Application No. 2,526,440.
Requisition by the Examiner Dated Mar. 25, 2013 From the Canadian Intellectual Property Office Re. Application No. 2,619,114.
Response Dated Jun. 2, 2011 to Office Action of Feb. 3, 2011 From the Israel Patent Office Re.: Application No. 172135.
Response Dated Jul. 3, 2011 to Examination Report of Apr. 19, 2011 From the Instituto Mexicano de la Propriedad Industrial Re. Application No. MX/a/2008/002262 and Its Summary Into English.
Response Dated Oct. 3, 2011 to Examiner's Report of Jun. 24, 2011 From the Australian Government, IP Australia Re. Application No. 2006281018.
Response Dated Jan. 4, 2010 to Official Action of Sep. 2, 2009 From the US Patent and Trademark Office Re.: U.S. Appl. No. 11/629,411.
Response Dated Oct. 4, 2011 to Official Action of Jul. 8, 2011 From the US Patent and Trademark Office Re. U.S. Appl. No. 12/083,978.
Response Dated Dec. 5, 2010 to Office Action of Aug. 4, 2010 From the Israel Patent Office Re.: Application No. 172135.
Response Dated Jul. 6, 2011 to Examiner's Report of Dec. 20, 2010 From the Australian Government, IP Australia Re. Application No. 2005234725.
Response Dated Jun. 6, 2011 to Official Action of May 10, 2011 From the US Patent and Trademark Office Re. U.S. Appl. No. 12/457,199.
Response Dated Jan. 7, 2010 to Communication Pursuant to Article 94(3) EPC of Sep. 9, 2009 From the European Patent Office Re.: Application No. 04734072.4.
Response Dated Mar. 8, 2011 to Examiner's Report of Jan. 13, 2011 From the Australian Government, IP Australia Re.: Application No. 2005252469.
Response Dated Feb. 9, 2011 to Communication Pursuant to Article 94(3) EPC of Nov. 19, 2010 From the European Patent Office Re.: Application No. 06809784.9.
Response Dated Jun. 9, 2011 to Examiner's Report of Dec. 20, 2011 From the Australian Government, IP Australia Re. Application No. 2005234725.

Response Dated Mar. 9, 2011 to Office Action of Nov. 11, 2010 From the Israel Patent Office Re. Application No. 206118.
Response Dated Jan. 10, 2012 to European Search Report and the European Search Opinion of Jun. 14, 2011 From the European Patent Office Re. Application No. 11154193.4.
Response Dated Aug. 11, 2011 to Examination Report of Aug. 1, 2011 From the Government of India, Patent Office Re.: Application No. 158/CHENP/2007.
Response Dated Dec. 12, 2010 to Examiner's Report of Dec. 17, 2009 From the Australian Government, IP Australia Re.: Application No. 2005252469.
Response Dated Oct. 12, 2010 to Communication Pursuant to Article 94(3) EPC of May 12, 2010 From the European Patent Office Re.: Application No. 06766224.7.
Response Dated Sep. 13, 2010 to Office Action Dated May 13, 2010 From the Israel Patent Office Re. Application No. 180022.
Response Dated Dec. 14, 2010 to Examination Report of Sep. 22, 2010 From the Instituto Mexicano de la Propriedad Industrial Re. Application No. MX/a/2008/005280.
Response Dated Feb. 14, 2011 to Supplementary European Search Report and the European Search Opinion of Jul. 29, 2010 From the European Patent Office Re. Application No. 08776651.5.
Response Dated Mar. 14, 2011 to Official Action of Feb. 15, 2011 From the US Patent and Trademark Office Re. U.S. Appl. No. 12/448,359.
Response Dated Oct. 14, 2010 to Office Action of Jun. 17, 2010 From the Israel Patent Office Re. Application No. 190918.
Response Dated Sep. 14, 2010 to Official Action of Aug. 18, 2010 From the US Patent and Trademark Office Re. U.S. Appl. No. 12/083,978.
Response Dated Dec. 15, 2011 to Examiner's Report of Aug. 1, 2011 From the Australian Government, IP Australia Re. Application No. 2005234725.
Response Dated Jun. 15, 2011 to Examiner's Report of Mar. 31, 2011 From the Australian Government, IP Australia Re.: Application No. 2005252469.
Response Dated Jun. 17, 2011 to Examiner's Report of Mar. 31, 2011 From the Australian Government, IP Australia Re.: Application No. 2005252469.
Response Dated May 17, 2010 to Office Action of Jan. 22, 2010 From the State Intellectual Property Office of the People's Republic of China Re.: Application No. 200580027481.4.
Response Dated Oct. 17, 2011 to Requisition by the Examiner of Jun. 15, 2011 From the Canadian Intellectual Property Office Re. Application No. 2,526,440.
Response Dated Oct. 18, 2011 to Official Action of Sep. 19, 2011 From the US Patent and Trademark Office Re. U.S. Appl. No. 12/810,855.
Response Dated Dec. 19, 2011 to Examiner's Report of Oct. 19, 2011 From the Australian Government, IP Australia Re. Application No. 2006281018.
Response Dated Jan. 19, 2011 to Supplementary European Search Report and the European Search Opinion of Jul. 1, 2010 From the European Patent Office Re. Application No. 07849616.3.
Response Dated Oct. 19, 2011 to Official Action of Apr. 19, 2011 From the US Patent and Trademark Office Re. U.S. Appl. No. 12/448,359.
Response Dated Jul. 20, 2011 to Examination Report of May 25, 2011 From the Government of India, Patent Office Re.: Application No. 158/CHENP/2007.
Response Dated Apr. 21, 2011 to Communication Pursuant to Article 94(3) EPC of Nov. 8, 2010 From the European Patent Office Re.: Application No. 04734072.4.
Response Dated Sep. 21, 2010 to Notice of Allowance of Apr. 16, 2010 From the US Patent and Trademark Office Re.: U.S. Appl. No. 11/629,411.
Response Dated Dec. 22, 2011 to Official Action of Aug. 22, 2011 From the US Patent and Trademark Office Re. U.S. Appl. No. 12/457,199.
Response Dated Feb. 22, 2010 to Official Action of Oct. 22, 2009 From the US Patent and Trademark Office Re.: U.S. Appl. No. 11/990,386.

(56) References Cited

OTHER PUBLICATIONS

Response Dated Feb. 23, 2011 to Communication Pursuant to Rule 70(2) EPC and Reference to Rule 39(1) EPC of Sep. 13, 2010 From the European Patent Office Re.: Application No. 09163033.5.
Response Dated Mar. 23, 2011 to Official Action of Nov. 23, 2010 From the US Patent and Trademark Office Re. U.S. Appl. No. 12/083,978.
Response Dated Feb. 24, 2011 to Communciation Pursuant to Rules 70(2) and 70a(2) EPC of Aug. 30, 2010 From the European Patent Office Re. Application No. 08738191.9.
Response Dated Mar. 24, 2011 to Examination Report of Nov. 3, 2010 From the Government of India, Patent Office Re.: Application No. 158/CHENP/2007.
Response Dated Oct. 24, 2010 to Office Action of Sep. 2, 2010 From the Rospatent, Federal State Institution, Federal Institute for Industrial Property of the Federal Service for Intellectual Property, Patents and Trademarks of the Russian Federation Re. Application No. 2008120395.
Response Dated Jul. 25, 2011 to Examiner's Report of Jul. 21, 2011 From the Australian Government, IP Australia Re. Application No. 2005234725.
Response Dated Sep. 25, 2011 to Examiner's Report of Jun. 30, 2011 From the Australian Government, IP Australia Re. Application No. 2006307457.
Response Dated Oct. 27, 2011 to Communication Pursuant to Article 94(3) EPC of Jun. 29, 2011 From the European Patent Office Re. Application No. 08738191.9.
Response Dated Oct. 27, 2011 to Office Action of Jul. 1, 2011 From the State Intellectual Property Office of the People's Republic of China Re. Application No. 200880017707.6.
Response Dated Oct. 27, 2011 to Supplementary European Search Report and the European Search Opinion of May 6, 2011 From the European Patent Office Re. Application No. 09750276.9.
Response Dated Jun. 29, 2010 to Examination Report of Feb. 17, 2010 From the Instituto Mexicano de la Propriedad Industrial Re. Application No. PA/a/2005/012565.
Response Dated Jun. 29, 2011 to Communication Pursuant to Article 94(3) EPC of Mar. 8, 2011 From the European Patent Office Re.: Application No. 06809784.9.
Response Dated May 31, 2010 to Office Action of Jan. 31, 2010 From the Israel Patent Office Re.: Application No. 172135.
Response Dated Oct. 31, 2011 to Notification of the First Office Action of Jun. 30, 2011 From the State Intellectual Property Office of the People's Republic of China Re. Application No. 200680047610.0.
Restriction Official Action Dated Feb. 1, 2012 From the US Patent and Trademark Office Re. U.S. Appl. No. 12/669,975.
Restriction Official Action Dated Mar. 1, 2013 From the US Patent and Trademark Office Re. U.S. Appl. No. 13/254,183.
Restriction Official Action Dated Apr. 4, 2013 From the US Patent and Trademark Office Re. U.S. Appl. No. 13/125,047.
Restriction Official Action Dated Apr. 11, 2012 From the US Patent and Trademark Office Re. U.S. Appl. No. 12/834,106.
Restriction Official Action Dated Feb. 13, 2012 From the US Patent and Trademark Office Re. U.S. Appl. No. 12/594,853.
Restriction Official Action Dated Nov. 13, 2012 From the US Patent and Trademark Office Re. U.S. Appl. No. 12/992,902.
Summary of Office Action Dated Sep. 2, 2010 From the Rospatent, Federal State Institution, Federal Institute for Industrial Property of the Federal Service for Intellectual Property, Patents and Trademarks of the Russian Federation Re. Application No. 2008120395.
Supplementary European Search Report and the European Search Opinion Dated Feb. 1, 2010 From the European Patent Office Re.: Application No. 06766224.7.
Supplementary European Search Report and the European Search Opinion Dated Jul. 1, 2010 From the European Patent Office Re. Application No. 07849616.3.
Supplementary European Search Report and the European Search Opinion Dated Jan. 2, 2012 From the European Patent Office Re. Application No. 09807983.3.
Supplementary European Search Report and the European Search Opinion Dated Jul. 6, 2012 From the European Patent Office Re. Application No. 10748403.2.
Supplementary European Search Report and the European Search Opinion Dated May 6, 2011 From the European Patent Office Re. Application No. 09750276.9.
Supplementary European Search Report and the European Search Opinion Dated Aug. 11, 2010 From the European Patent Office Re. Application No. 08738191.9.
Supplementary European Search Report and the European Search Opinion Dated Feb. 14, 2013 From the European Patent Office Re. Application No. 10785834.2.
Supplementary European Search Report and the European Search Opinion Dated Sep. 14, 2009 From the European Patent Office Re.: Application No. 06809784.9.
Supplementary European Search Report and the European Search Opinion Dated Apr. 18, 2012 From the European Patent Office Re. Application No. 09823171.5.
Supplementary European Search Report and the European Search Opinion Dated Jul. 29, 2010 From the European Patent Office Re. Application No. 08776651.5.
Supplementary European Search Report Dated Apr. 23, 2008 From the European Patent Office Re.: Application No. 05750089.4.
Supplementary European Search Report Dated Oct. 31, 2007 From the European Patent Office Re.: Application No. 04734072.4.
Supplementary Partial European Search Report Dated Aug. 30, 2007 From the European Patent Office Re.: Application No. 04734072.4.
Translation of Decision of Rejection Dated Dec. 9, 2011 From the State Intellectual Property Office of the People's Republic of China Re.: Application No. 200580027481.4.
Translation of Examination Report Dated Sep. 6, 2010 From the Government of the People's Republic of Bangladesh, Department of Patents, Designs and Trademarks, Ministry of Industries Re. Application No. 275/2009.
Translation of Notice of Paying Restoration Fee for Unity of Invention Dated Oct. 29, 2012 From the State Intellectual Property Office of the People's Republic of China Re. Application No. 200880127757.X.
Translation of Notice of Payment of the Restoration Fee for Unity of Invention Dated Mar. 20, 2009 From the State Intellectual Property Office of the People's Republic of China Re.: Application No. 200580027481.4.
Translation of Notice to Amendment Dated Aug. 31, 2012 From the Thai Patent Office, Department of Intellectual Property Office Re. Application No. 0901000235.
Translation of Notification of the Office Action Dated Dec. 1, 2011 From the State Intellectual Property Office of the People's Republic of China Re. Application No. 200680047610.0.
Translation of Notification of the Office Action Dated Jun. 30, 2011 From the State Intellectual Property Office of the People's Republic of China Re. Application No. 200680047610.0.
Translation of Office Action Dated Jul. 1, 2011 From the State Intellectual Property Office of the People's Republic of China Re. Application No. 200880017707.6.
Translation of Office Action Dated Jan. 4, 2012 From the State Intellectual Property Office of the People's Republic of China Re. Application No. 200880109464.9.
Translation of Office Action Dated Apr. 9, 2012 From the State Intellectual Property Office of the People's Republic of China Re. Application No. 200880017707.6.
Translation of Office Action Dated Sep. 13, 2012 From the State Intellectual Property Office of the People's Republic of China Re. Application No. 200910217137.1.
Translation of Office Action Dated Jan. 17, 2012 From the State Intellectual Property Office of the People's Republic of China Re. Application No. 201110104274.1.
Translation of Office Action Dated Jan. 17, 2013 From the State Intellectual Property Office of the People's Republic of China Re. Application No. 201110104274.1.
Translation of Office Action Dated Oct. 19, 2010 From the State Intellectual Property Office of the People's Republic of China Re. Application No. 200680038391.X.

(56) References Cited

OTHER PUBLICATIONS

Translation of Office Action Dated Jun. 22, 2011 From the State Intellectual Property Office of the People's Republic of China Re. Application No. 200880127685.9.
Translation of Office Action Dated Mar. 22, 2013 From the State Intellectual Property Office of the People's Republic of China Re. Application No. 200880109464.9.
Translation of Office Action Dated Feb. 25, 2013 From the State Intellectual Property Office of the People's Republic of China Re. Application No. 200910217137.1.
Translation of Office Action Dated Dec. 31, 2011 From the State Intellectual Property Office of the People's Republic of China Re. Application No. 200910217137.1.
Translation of Search Report Dated Jan. 17, 2013 From the State Intellectual Property Office of the People's Republic of China Re. Application No. 201110104274.1.
Translation of the Office Action Dated Jan. 9, 2009 From the State Intellectual Property Office Re.: Application No. 2004800200597.0.
Written Opinion Dated Jul. 2, 2009 From the International Searching Authority Re.: Application No. PCT/IL07/01590.
Written Opinion Dated Jan. 3, 2007 From the International Searching Authority Re.: Application No. PCT/IL2005/000627.
Written Opinion Dated Mar. 4, 2009 From the International Searching Authority Re.: Application No. PCT/IL08/01024.
Written Opinion Dated Nov. 4, 2005 From the International Searching Authority Re.: Application No. PCT/Il04/00431.
Written Opinion Dated Aug. 27, 2008 From the International Searching Authority Re.: Application No. PCT/IL06/00947.
Adachi et al. "*Oryza sativa japonica* Group cDNA Clone:J023021L06, Full Insert Sequence", Database EMBASE [Online], XP002665608, Retrieved From EBI, Database Accession No. AK099270, Jul. 19, 2003.
Aharon et al. "Overexpression of a Plasma Membrane Aquaporin in Transgenic Tobacco Improves Plant Vigor Under Favorable Growth Conditions But Not Under Drought or Salt Stress", The Plant Cell, 15: 439-447, Feb. 2003.
Alcala et at "EST543159 Tomato Callus Solanum Lycopersicum cDNA Clone cLEC80A19 5-end, mRNA Sequence", GenBank: BI923254.1, GenBank Accession No. BI923254, Oct. 17, 2001.
Alcala et al. "Generation of ESTs From Tomato Fruit Tissue", Database GenBank on STIC, National Center for Biotechnology Information, Accession No. AW932839, 2001.
Apse et al. "Engineering Salt Tolerance in Plants", Current Opinion in Biotechnology, 13: 146-150, 2002.
Apse et al. "Engineering Salt Tolerance in Plants", Current Opinion in Biotechnology, XP003018468, 13(2): 146-150, Apr. 1, 2002.
*Arabidopsis* Genome Initiative "Analysis of the Genome Sequence of the Flowering Plant *Arabicopsis thaliana*" Nature, 408: 796-815, Dec. 14, 2000.
Backhaus et al. "Nucleotide Sequence of a cDNA for a P2 60S Acidic Ribosomal Protein From Parthenium Argentatum", Plant Physiology, 106: 395, 1994.
Bautista et al. "*Arabidopsis thaliana* At5g06690 mRNA, Complete Cds", Unpublished, The Salk Institute for Biological Studies, La Jolla, CA, USA, GenBank: BT029447, Nov. 15, 2006.
Benfey et al. "The CaMV 35S Enhancer Contains at Least Two Domains Which Can Confer Different Development and Tissue-Specific Expression Patterns", The EMBO Journal, 8(8): 2195-2202, 1989.
Benfey et al. "The Cauliflower Mosaic Virus 35S Promoter: Combinatorial Regulation of Transcription in Plants", Science, 250(4983): 959-966, Nov. 16, 1990.
Bernhardt et al. "The bHLH Genes GLABRA3 (GL3) and Enhancer of GLABRA3 (EGL3) Specify Epidermal Cell Fate in the *Arabidopsis* Root", Development, 130(26): 6431-6439, 2003.
Blast "BLAST Results", 1 P.
Blewitt et al. "BNLGHi10083 Six-Day Cotton Fiber Gossypium Hirsutum cDNA 5' Similar to (AC004521) Unknown Protein [*Arabidopsis thaliana*], mRNA Sequence", XP002576188, Retrieved Fron EBI Accession No. EMBL:AI728187, Database Accession No. AI728187, Jun. 12, 1999. Sequence.
Blewitt et al. "BNLGHi8081 Six-Day Cotton Fiber Gossypium Hirsutum cDNA 5' Similar to (AC004521) Unknown Protein [*Arabidopsis thaliana*], mRNA Sequence", XP002576189, Retrieved From EBI Accesion No. EMBL:AI730835, Database Accession No. AI730835, Jun. 12, 1999. Sequence.
Blewitt et al. "BNLGHi8396 Six-Day Cotton Fiber Gossypium Hirsutum cDNA 5' Similar to (AC004521) Unknown Protein [*Arabidopsis thaliana*], mRNA Sequence", XP002576190, Retrieved From EBI Accession No. EMBL:AI27553, Database Accession No. AI27553, Jun. 12, 1999. Sequence.
Blewitt et al. "Gossypium Hirsutum Strain Acala Maxxa BURP Domain-Containing Protein (BNL1924) mRNA, Complete CDS", GenBank Nucleotide, GenBank Accession No. AY343972, Aug. 16, 2003.
Bowie et al. "Deciphering the Message in Protein Sequences: Tolerance to Amino Acid Substitutions", Science, 247(4948): 1306-1310, Mar. 16, 1990.
Brandle et al. "Perspectives on the Production of Recombinant Proteins in Plants", AgBiotechNet, 3(ABN 070): 1-4, 2001. Abstract.
Castelli et al. "*Arabidopsis thaliana* Full-Length cDNA Complete Sequence From Clone GSLTFB52ZA10 of Flowers and Buds of Strain Col-0 of *Arabidopsis thaliana* (Thale Cress)", GeneBank Direct Submission BX829993, Accession No. BX829993, Feb. 6, 2004.
Cheuk et al. "*Arabidopsis thaliana* At2g40550 Gene, Complete CDS", Database EMBL [Online], XP002673499, Retrieved From EBI Accession No. EM_PL: BT022032.1, Database Accession No. BT022032, May 4, 2005.
Cheuk et al. "*Arabidopsis thaliana* At2g46960/F14M4.21 mRNA, Complete CDS", Database EMBL [Online], XP002593835, Retrieved From EBI Accession No. Embl:AY091688, Database Accession No. AY091688, Apr. 14, 2002.
Ciddi et al. "Elicitation of Taxus SP. Cell Cultures for Production of Taxol", Biotechnology Letters, 17(12): 1343-1346, Dec. 1995.
Daniell et al. "Solanum Bulbocastanum Chloroplast, Complete Genome", GenBank NCBI, Accession No. NC_007943, Mar. 26, 2010. p. 1, Source, p. 10-11, Nucleotides 46590-47195, Gene 'RPS4'.
Davletova et al. "The Zinc-Finger Protein Zat12 Plays a Central Role in Reactive Oxygen and Abiotic Stress Signaling in *Arabidopsis*", Plant Physiology, 139: 847-856, Oct. 2005.
Del Pozo et al. "F-Box Proteins and Protein Degradation: An Emerging Theme in Cellular Regulation", Plant Molecular Biology, 44(2): 123-128, Sep. 2000.
Desveaux et al. "Whirly Transcription Factors: Defense Gene Regulation and Beyond", Trends in Plant Science, TiPS, 10(2): 95-102, Feb. 2005.
Feng et al. "Probable Cinnamyl Alcohol Dehydrogenase 6", Darabase UniProt [Online], XP002665609, Retrieved From EBI, Database Accession No. Q7XWU3, Mar. 1, 2004.
Francois et al. "Overexpression of the VvLTP1 Gene Interferes With Somatic Embryo Development in Grapevine", Functional Plant Biology, 35(5): 394-402, 2008.
Fray et al. "Nucleotide Sequence and Expression of a Ripening and Water Stress-Related cDNA From Tomato With Homology to the MIP Class of Membrane Channel Proteins", Plant Molecular Biology, XP009117320, 24(3): 539-543, 1994. Figs.1, 2. & Database UniProt, REcName: Full=Probable Aquaporin PIP-Type pTOM75; AltName: Full=Ripening-Associated Membrane Protein; Short=RAMP, Oct. 1, 1994.
Friedberg "Automated Protein Function Prediction—The Genomic Challenge", Briefings in Bioinformatics, 7(3): 225-242, 2006.
Gardiner et al. "Zea Mays PCO131392 mRNA Sequence", Database EMBL/GenBank/DDBJ, EBI Database Accession No. AY107021, XP002542347, May 28, 2002. 96,5% Identity in 1118 nt Overlap of AY107021 (1118 nt) With SEQ ID No. 68 (1348 nt) of the Present Application, Abstract.
Gaxiola et al. "Drought- and Salt-Tolerant Plants Result From Overexpression of the AVP1 H+ -Pump", Proc. Natl. Acad. Sci. USA, PNAS, 98(20): 11444-11449, Sep. 25, 2001.

(56) References Cited

OTHER PUBLICATIONS

Good et al. "Can Less Yield More? Is Reducing Nutrient Input Into the Environment Compatible With Maintaining Crop Production?", Trends in Plant Science, 9(12): 597-605, Dec. 2004.
Good et al. "Engineering Nitrogen Use Efficiency With Alanine Aminotransferase", Canadian Journal of Botany, 85: 252-262, 2007.
Gowik et al. "Cis-Regulatory Elements for Mesophyll-Specific Gene Expression in the C4 Plant Flaveria Trinervia, the Promoter of the C4 Phosphoenolpyruvate Carboxylase Gene", The Plant Cell, 16: 1077-1090, 2004.
Grover et al. "Understanding Molecular Alphabets of the Plant Abiotic Stress Responses", Current Science, 80(2): 206-216, Jan. 25, 2001.
Guo et al. "Protein Tolerance to Random Amino Acid Change", Proc. Natl. Acad. Sci. USA, PNAS, 101(25): 9205-9210, 2004.
Hachez et al. "Modulating the Expression of Aquaporin Genes in Planta: A Key to Understand Their Physiological Functions?", Biochimica et Biophysica Acta, XP005655605, 1758(8): 1142-1156, Aug. 1, 2006. p. 1151, col. 1, § -p. 1153, col. 1, § 1, Table 1.
Harwood "Plant Fatty Acid Synthesis", The AOCS Lipid Library, 11 P., Apr. 12, 2010.
Hattori et al. "An Acetohydroxy Acid Synthase Mutant Reveals a Single Site Involved in Multiple Herbicide Resistance", Molecular and General Genetics, 246: 419-425, 1995. Abstract!
Hill et al. "Functional Analysis of Conserved Histidines in ADP-Glucose Pyrophosphorylase From *Escherichia coli*", Biochemical and Biophysical Research Communications, 244(2): 573-577, 1998.
Hirner et al. "*Arabidopsis* LHT1 Is a High-Affinity Transporter for Cellular Amino Acid Uptake in Both Root Epidermis and Leaf Mesophyll", The Plant Cell, 18: 1931-1946, Aug. 2006.
Holmstroem et al. "Drought Tolerance in Tobacco", Nature, 379: 683-684, 1996. Abstract.
In et al. "Panax Gingseng mRNA for Cytoplasmic Ribosomal Protein S13, Complete Cds", Database EMBL [Online], Retrieved From EBI Accession No. EMBL, Database Accession No. AB043974, 2000.
Invitrogen "SuperScript® Plasmid System With Gateway® Technology for cDNA Synthesis and Cloning", Invitrogen by Life Technologies, User Manual, Catalog No. 18248-013, Manual Part No. 11108, 44 P., Dec. 22, 2010.
Ishikawa et al. JP 2005-185101: Full Length cDNA of Plant and the Use Thereof, Database EMBL [Online], XP002678022, Retrieved From EBI Accession No. EM_PAT:IIV067703, Database Accession No. IIV067703, Jul. 15, 2011. Sequence.
Ji et al. "Gossypium Hirsutum Expansin mRNA, Complete CDs", Database EMBL [Online], XP002474936, Retrieved From EBI Accession No. EMBL: AY189969, Database Accession No. AY189969, May 20, 2003.
Ji et al. "Isolation and Analyses of Genes Preferentially Expressed During Early Cotton Fiber Development by Subtractive PCR and cDNA Array", Nucleic Acids Research, XP002474935, 31(10): 2534-2543, May 15, 2003.
Johansson et al. "The Role of Aquaporins in Cellular and Whole Plant Water Balance," Biochimica et Biophysica Acta 1465: 324-342, 2000.
Kandel et al. "Cloning, Functional Expression, and Characterization of CYP709C1, the First Sub-Terminal Hydroxylase of Long Chain Fatty Acid in Plants", Journal of Biological Chemistry, JBC, 280(43): 35881-35889, Oct. 28, 2005. p. 35887, col. 1, Para 2.
Kano-Murakami et al. "A Rice Homeotic Gene, OSH1, Causes Unusual Phenotypes in Transgenic Tobacco", FEBS Letters, 334(3): 365-368, Nov. 1993.
Katavic et al. "Utility of the *Arabidopsis* FAE1 and Yeast SLC1-1 Genes for Improvement in Erucic Acid and Oil Content in Rapeseed", Biochemical Society Transactions, 28(6): 935-937, Dec. 2000.
Katavic et al. "Utility of the *Arabidopsis* FAE1 and Yeast SLC1-1 Genes for Improvements in Erucic Acid and Oil Content in Rapeseed", Biochemical Society Transactions, 28: 935-7, 2000. Abstract!

Keskin et al. "A New, Structurally Nonredundant, Diverse Data Set of Protein-Protein Interfaces and Its Implications", Protein Science, 13: 1043-1055, 2004.
Kikuchi et al. "Oryza Sativa Japonica Group cDNA Clone:J023131O04, Full Insert Sequence", GenBank Database Accession No. AK072531, Jul. 2, 2013.
Kikuchi et al. "Rice cDNA-Encoded Protein SEQ ID No. 31047", Database Geneseq [Online], XP002678021, Retrieved From EBI Accession No. GSP:AQD37188, Database Accession No. AGD37188, Jun. 12, 2008. Shows 100% Identity to Present SEG ID No.246 (Protein) and Corresponding Polynucleotide Shows 100% Identity to SEQ ID No. 7 Over 458 Nucleotides. Abstract.
Kim et al. "*Arabidopsis thaliana* At2g46960/F14M4.21 mRNA, Complete CDS", Database EMBL [Online], XP002593834, Retrieved From EBI Accession No. EMBL:AF367329, Database Accession No. AF367329, Apr. 12, 2001.
Kim et al. "Molecular Cloning of Low-Temperature-Inducible Ribosomal Proteins From Soybean", Journal of Experimental Botany, 55(399): 1153-1155, 2004.
Kirkness et al. "Lycopersicon Esculentum Clone 133453R, mRNA Sequence", Database EMBL [Online], XP002529190, Retrieved From EBI Accession No. EMBL:BT014251, Database Accession No. BT014251, May 12, 2004.
Kirubakaran et al. "Characterization of a New Antifungal Lipid Transfer Protein From Wheat", Plant Physiology and Biochemistry, 46: 918-927, 2008.
La Rosa et al. "*Oryza sativa* Amino Acid Sequence SEQ ID No. 133688", Database Geneseq [Online], XP002678023, Retrieved From EBI Accession No. GSP:ANM19687, Database Accession No. ANM19687, Dec. 28, 2007. 100% Identity to Present SEQ IFD No. 246, Corresponding Polynucleotide Has 99,6% Identity to Present SEQ ID No. 7 Over 488 Nucleotides. Abstract, Sequence.
La Rosa et al. "*Oryza sativa* Nucleotide Sequence SEQ ID No. 31205", Database Geneseq [Online], XO002678024, Retrieved From EBI Accession No. GSN:ANL17203, Database Accession No. ANL17203, Dec. 28, 2007. Sequence.
Li et al. "Gossypium Hirsutum Dehydration-Induced Protein RD22-Like Protein (RDL) mRNA, Complete CDS", EBI Accession No. EMBL:AY072821, XP002639385, Database Accession No. AY072821, Dec. 4, 2002. Compound.
Li et al. "Isolation of Genes Preferntially Expressed in Cotton Fibers by cDNA Filter Arrays and RT-PCR", Plant Science, XP002639386, 163(6): 1113-1120, 2002.
Lin et al. "*Arabidopsis thaliana* Chromosome III BAC F7O18 Genomic Sequence, Complete Sequence", GenBank Accession No. ACO11437, Oct. 30, 2002.
Liu et al. "Root-Specific Expression of a Western White Pine PR10 Gene Is Mediated by Different Promoter Regions in Transgenic Tobacco", Plant Molecular Biology, 52: 103-120, 2003.
Lurin et al. "Genome-Wide Analysis of *Arabidopsis* Pentatricopeptide Repeat Proteins Reveals Their Essential Role in Organelle Biogenesis", The plant Cell, 16: 2089-2103, Aug. 2004.
Matsumoto et al. "Hordeum Vulgare Subsp. Vulgare, Full-Length cDNA", UniProtKB/TrEMBL, ID: F2DLE8-HORVD, UniProt Accession No. F2DLE8, May 31, 2011.
Matz et al. "Gossypium Hirsutum GHDEL65 (ghde165) mRNA, Complete CDS", GenBank Nucleotide, GenBank Accession No. AF336280, Mar. 15, 2001.
Maurel "Plant Aquaporins: Novel Functions and Regulation Properties", FEBS Letters, XP022078418, 581(12): 2227-2236, May 25, 2007. p. 2230, col. 2, Last §-p. 2231, col. 1, § 2, Fig. 1.
McConnell et al. "Role of Phabulosa and Phavoluta in Determining Radial Patterning in Shoots", Nature, 411(6338): 709-713, Jun. 7, 2001.
Merriam-Webster "Exogenous Definition", Merrian-Webster On-Line Dictionary, 2010.
NCBI "Protein Sequence (588 Letters)", NCBI BLAST Basic Local Alignment Search Tool, 3 P., Retrieved From the Internet on Nov. 24, 2009.
Ngo et al. "Computational Complexity, Protein Structure Prediction, and the Levinthal Paradox", The Protein Folding Problem and Tertiary Structure Prediction, p. 433, 492-495, 1994.

(56) References Cited

OTHER PUBLICATIONS

Nuccio et al. "Metabolic Engineering of Plants for Osmotic Stress Resistance", Current Opinion in Plant Biology, XP002216348, 2(2): 128-134, Apr. 1, 1999.
Orford et al. "Specific Expression of an Expansin Gene During Elongation of Cotton Fibres", Biochimica et Biophysica Acta, XP000866032, 1398(3): 342-346, Jul. 9, 1998. Abstract, p. 343, Fig. 1.
Orzaez et al. "Agroinjection of Tomato Fruits. A Tool for Rapid Functional Analysis of Transgenes Directly in Fruit", Plant Physiology, 140: 3-11, 2006.
Park et al. "Glycine Max Ribosomal Protein S13 (RPS13) mRNA, Complete Cds", Database EMBL [Online], Retreieved From EBI Accession No. EMBL, Database Accession No. AY453393, 2004.
Payne et al. "GL3 Encodes a bHLH Protein That Regulates Trichome Development in *Arabidopsis* Through Interaction With GL1 and TTG1", Genetics, 156: 1349-1362, Nov. 2000.
Payne et al. "Heterologous MYB Genes Distinct From GL1 Enhance Trichome Production When Overexpressed in Nicotiana Tabacum", Development, 126: 671-682, 1999.
Pilon-Smits et al. "Improved Performance of Transgenic Fructan-Accumulating Tobacco under Drought Stress", Plant Physiology, 107: 125-130, 1995.
Plant Energy Biology "Protein_Coding: Cationic Amino Acid Transporter 2 (TAIR10)", Plant Energy Biology: SUBA3 Flatfile for AT1G58030.1, Database, 1 P., 2007.
Purnelle et al. "*Arabidopsis thaliana* DNA Chromosome 3, BAC Clone F3C22", Database EMBL [Online], XP002640829, Retrieved From EBI Accession No. EMBL:AL353912, Database Accession No. AL 353912, Apr. 27, 2000. Compound.
Quesada et al. "Genetic Architecture of NaCl Tolerance in *Arabidopsis*", Plant Physiology, 130: 951-963, 2002. Abstract!
Rolletschek et al. "Ectopic Expression of an Amino Acid Transporter (VfAAP1) in Seeds of Vica Narbonensis and Pea Increases Storage Proteins", Plant Physiology, 137: 1236-1249, Apr. 2005.
Rounsley et al. "*Arabidopsis thaliana* Chromosome 2 Clone T2P4 Map CIC10A06, Complete Sequence", Database EMBL [Online], XP002673500, Retrieved From EBI Accession No. EMBL:AC002336, Database Accession No. AC002336, Jul. 18, 1997. Sequence.
Saez-Vasquez et al. "Accumulation and Nuclear Targeting of BnC24, a Brassica Napus Ribosomal Protein Corresponding to a mRNA Accumulating in Response to Cold Treatment", Plant Science, 156(1): 35-46, 2000.
Saijo et al. "Over-Expression of a Single Ca2+ -Dependent Protein Kinase Confers Both Cold and Salt/Drought Tolerance on Rice Plants", The Plant Journal 23(3): 319-327, 2000.
Skriver et al. "Cis-Acting DNA Elements Responsive to Gibberellin and Its Antagonist Abscisic Acid", Proceedings of the National Academy of Sciences USA 88: 7266-7270, 1991.
Smart et al. "MIP Genes Are Down-Regulated Under Drought Stress in Nicotiana Glauca", Plant and Cell Physiology, XP002455682, 42(7): 686-693, 2001. p. 686, Reference to Database Entry AF290618, p. 692, 1-h col., § 2.
Smart et al. "Nicotiana Glauca Putative Delta TIP (MIP2) mRNA, Complete Cds", Database EMBL [Online], Retrieved From EBI Accession No. EMBL: AF290618, XP002455682, Database Accession No. AF290618, Jan. 2, 2001.
Soderlund et al. "Sequencing, Mapping, and Analysis of 27,455 Maize Full-Length cDNAs", PLoS Genetics, 5(11): e1000740-1-e1000740-13, Nov. 2009.
Su et al. "Molecular and Functional Characterization of a Family of Amino Acid Transporter From *Arabidopsis*", Plant Physiology, 136: 3104-3113, Oct. 2004.
Sunkar et al. "Small RNAs as Big Players in Plant Abiotic Stress Responses and Nutrient Deprivation", Trends in Plant Science, XP022148764, 12(7): 301-309, Jul. 1, 2007.
TAIR "Encodes a Member of the Cationic Amino Acid Transporter (CAT) Subfamily of Amino Acid Polyamine Choline Transporters. Localized to the Tonoplast", TAIR, Locus: AT1G58030, TAIR Accession No. Locus:2196245, 4 P., 2013.
TAIR "Protein Kinase Superfamily Protein. Functions in: Protein Serine/Threonine Kinase Activity, Protein Kinase activity, Kinase Activity, ATP Binding ff.", TAIR, Locus: AT5G15080, TAIR Accession No. Locus:2147805, 4 P., 2013.
Takahashi et al. "The DNA Replication Checkpoint Aids Survival of Plants Deficient in the Novel Replisome Factor ETG1", The EMBO Journal, XP002537888, 27(13): 1840-1851, Jul. 9, 2008 & Supplementary Materials and Methods. Suppl. Fig. S6, p. 1844-1845.
Taliercio et al. "GH_TMIRS_129_G10_F Cooton Normalized Library dT Primed Gossypium Hirsutum cDNA, mRNA Sequence", EMBL-Bank, XP002659970, Retrieved From EBI Accession No. EM_EST:DW508992, Database Accession No. DW508992.
Taliercio et al. "GH_TMIRS_129_G10_R Cotton Normalized Library dT Primed Gossypium Hirsutum cDNA, mRNA Sequence", EMBL-Bank, XP002659971, Retrieved From EBI Accession No. EM_EST:DW508993, Database Accession No. DW508993.
Tamura et al. "Osmotic Stress Tolerance of Transgenic Tobacco Expressing a Gene Encoding a Membrane-Located Receptor-Like Protein From Tobacco Plants", Plant Physiology, 131(2): 454-462, 2003.
Tanaka et al. "Enhanced Tolerance Against Salt-Stress and Freezing-Stress of *Escherichia coli* Cells Expressing Algal BBC1 Gene", Current Microbiology, 42(3): 173-177, 2001.
Tarczynski et al. "Stress Protection of Transgenic Tobacco by Production of the Osmolyte Mannitol", Science, 259: 508-510, 1993. Abstract!.
Terminology "Frequently Asked Questions", Bioinformatics Website, Frequently Asked Questions, 2001.
Theologis et al. "Sequence and Analysis off Chromosome 1 of the Plant *Arabidopsis thaliana*", Nature, 408: 816-820, Dec. 14, 2000.
Thornton et al. "From Structure to Function: Approaches and Limitations", Nature Structural Biology. Structural Genomic Supplement, Nov. 2000, p. 991-994.
Udall et al. "A Global Assembly of Cotton ESTs", Genome Research, 16(3): 441-450, 2006.
Van der Hoeven et al. "EST301294 Tomato Root During/After Fruit Set, Cornell University Lycopersicon Esculentum cDNA Clone cLEX1K11 Similar to Vernicia Fordii Aquaporin, mRNA Sequence", Database EMBL [Online], Retrieved From EBI Accession No. EMBL: AW218814, XP002455680, Database Accession No. AW218814, Dec. 14, 1999. Abstract.
Van der Hoeven et al. "EST301295 Tomato Root During/After Fruit Set, Cornell University Lycopersicon Esculentum cDNA Clone cLEX1K11 Similar to Vernicia Fordii Aquaporin, mRNA Sequence", Database EMBL [Online], Retrieved From EBI Accession No. EMBL: AW218815, XP002455681, Database Accession No. AW218815, Dec. 14, 1999. Abstract.
Van der Hoeven et al. "EST312975 Tomato Root During/After Fruit Set, Cornell University Solanum Lycopersicum cDNA Clone cLEX14O20 5-, mRNA Sequence", GenBank, GenBank Accession No. AW622177.1.
Van der Hoeven et al. "EST428934 Tomato Nutrient Deficient Roots Lycopersicon Esculentum cDNA Clone cLEW26B2 5' Sequence, mRNA Sequence", Database EMBL, Retrieved From EBI Accession No. EMBL, Database Accession No. BF098413, 2000.
Van Haaren et al. "A Functional Map of the Fruit-Specific Promoter of the Tomato 2A11 Gene", Plant Molecular Biology, 21: 625-640, 1993. Abstract.
Vigeolas et al. "Increasing Seed Oil Content in Oil-Seed Rape (Brassica Napus L.) by Over-Expression of a Yeast Glycerol-3-Phosphate Dehydrogenase Under the Control of a Seed-Specific Promoter", Plant Biotechnology Journal, 5 Issue: 431 -441, 2007. Abstract.
Wallace et al. "Oligonucleotide Probes for the Screening of Recombinant DNA Libraries", Methods in Enzymology, XP002957829, 152: 432-442, Jan. 1, 1987.
Wang et al. "Control of Plant Trichome Development by a Cotton Fiber MYB Gene", The Plant Cell, 16: 2323-2334, Sep. 2004.

(56) References Cited

OTHER PUBLICATIONS

Wang et al. "Control of Plant Trichome Development by a Cotton Fiber MYB Gene", The Plant Cell, 16: 2323-2334, Sep. 2004. GenEmbl Database, Accession No. AY641990.
Wang et al. "The Soybean Dof-Type Transcription Factor Genes, GmDof4 and GmDof11, Enhance Lipid Content in the Seeds of Transgenic Arabidopsis Plants", The Plant Journal, 52: 716-729, 2007. Abstract!.
Wells "Additivity of Mutational Effects in Proteins", Biochemistry, 29 (37): 8509-8517, 1990.
Whisstock et al. "Prediction of Protein Function from Protein Sequence and Structure," Quarterly Reviews of Biophysics 36 (3): 307-340, Aug. 2003.
Wing et al. "An Integrated Analysis of the Genetics, Devlopment, and Evolution of Cotton Fiber", NBCI GenBank Accession No. BE052336, 2000.
Wing et al. "GA_Eb0023F09f Gossypium Arboreum 7-10 Dpa Fiber Library Gossypium Arboreum cDNA Clone GA_Eb0023F09f, mRNA Sequence", XP002576191, Retrieved From EBI Accession No. EMBL:BF275177, Database Accession No. BF275177, Nov. 20, 2000. Sequence.
Wing et al. "GA_Eb0026P18f Gossypium Arboreum 7-10 Dpa Fiber Library Gossypium Arboreum cDNA Clone GA_Eb0026P18f, mRNA Sequence", Database EMBL [Online], XP002640830, Retrieved From EBI Accession No. EMBL:BF277249, Database Accession No. BF277249, Nov. 20, 2000.
Wu et al. "SubName: Full—Major Intrinsic Protein", Database UniProt [Online], XP002529191, Retrieved From EBI Accession No. UNIPROT:AOFI89, Database Accession No. AOFI89, Nov. 28, 2006.
Xu et al. "Expression of a Late Embryogenesis Abundant Protein Gene, HVA1, From Barley Confers Tolerance to Water Deficit and Salt Stress in Transgenic Rice", Plant Physiology, 110: 249-257, 1996.
Yamada et al. "*Arabidopsis thaliana* Clone RAFL14-87-A16 (R20399) Unknown Protein (At1g60770) mRNA, Complete Cds", GenBank Accession No. BT002876, Retrieved From the Internet, Jan. 21, 2010.
Yamada et al. "*Arabidopsis thaliana* Unknown Proein (At3g51610) mRNA, Complete CDS", Database EMBL [Online], XP002640828, Retrieved Fom EBI Accession No. EMBL:AY034915, Database Accession No. AY034915, Jun. 13, 2001. Compound.
Yanagisawa et al. "Diversity and Similarity Among Recognition Sequences of Dof Transcription Factors", The Plant Journal, 17(2): 209-214, 1999.
Yanagisawa et al. "Metabolic Engineering With Dof1 Transcription Factor in Plants: Improved Nitrogen Assimilation and Growth Under Low-Nitrogen Conditions", Proc. Natl. Acad. Sci USA, PNAS, 101(20): 7833-7838, May 18, 2004.
Yanagisawa et al. "Metabolic Engineering With Dof1 Transcription Factor in Plants: Improved Nitrogen Assimilation and Growth Under Low-Nitrogen Conditions", Proc. Natl. Acad. Sci. USA, PNAS, 101(20): 7833-7838, May 18, 2004.
Young et al. "Hypothetical Protein MTR_7g116270 [Medicago Truncatula]", Database NCBI [Online], GenBank: AES82688.1, Database Accession No. AES82688, Nov. 21, 2011.
Zabrouskov et al. "Oxidative Metabolism and the Physiological Age of Seed Potatoes Are Affected by Increased Alpha-Linolenate Content", Physiologia Plantarum, 116: 172-185, 2002.
Zhang et al. "Phosphatidic Acid Regulates Microtubule Organization by Interaction With MAP65-1 in Response to Salt Stress in *Arabidopsis*", The Plant Cell, 24: 4555-4576, Nov. 2012.
Examination Report Dated Jul. 29, 2013 From the Instituto Mexicana de la Propiedad Industrial Re. Application No. MX/a/2010/012697 and Its Translation Into English.
Official Action Dated Sep. 20, 2013 From the US Patent and Trademark Office Re. U.S. Appl. No. 12/669,975.
Communication Pursuant to Article 94(3) EPC Dated Aug. 20, 2013 From the European Patent Office Re. Application No. 11172514.9.

International Search Report and the Written Opinion Dated Sep. 1, 2013 From the International Searching Authority Re. Application No. PCT/IB2013/054374.
Bennetzen et al. "Setaria Italica Strain Yugul SETITScaffold_2_Cont751, Whole Genome Shotgun Sequence", Database NCBI [Online], GenBank Accession No. AGNK01000751, May 11, 2012.
Briggs et al. "Poly(ADP-Ribosyl)ation in Plants", Trends in Plant Science, 16(7): 372-380, Jul. 31, 2011. p. 378.
NCBI "Predicted: Nudix IIydrolase 16, Mitochondrial-Like [Setaria Italica]", Database NCBI [Online], NCBI Reference Sequence: XP_004955808, Jun. 26, 2013.
Patent Examination Report Dated Feb. 9, 2015 From the Australian Government, IP Australia Re. Application No. 2012241058.
Requisition by the Examiner Dated Aug. 27, 2013 From the Canadian Intellectual Property Office Re. Application No. 2,526,440.
Examination Report Dated Dec. 16, 2013 From the Government of India, Patent Office, Intellectual Property Building Re. Application No. 2570/CHENP/2008.
Li et al. "Dehydration-Induced Protein RD22-Like Protein [Gossypium Hirsutum]", NCBI Database [Online], GenBank: AAL67991.1, GenBank Accession No. AAL67991, Dec. 4, 2002.
Official Action Dated Jul. 26, 2013 From the US Patent and Trademark Office Re. U.S. Appl. No. 13/254,183.
Matsumoto et al. "Os11g0162200 [*Oryza sativa japonica* Group]", Direct GenBank Sequence Submission, GenBank: BAF27672.1, GenBank Accession No. BAF27672, Aug. 11, 2012.
Examination Report Dated Jun. 7, 2013 From the Instituto Mexicano de la Propiedad Industrial Re. Application No. MX/a/2011/003575 and Its Translation Into English.
Examination Report Dated Jun. 20, 2013 From the Instituto Mexicano de la Propiedad Industrial Re. Application No. MX/a/2011/007294 and Its Translation Into English.
Office Action Dated Oct. 28, 2013 From the State Intellectual Property Office of the People's Republic of China Re. Application No. 201110104274.1 and Its Translation Into English.
Communication Pursuant to Rule 58 EPC or Rule 159 EPC, Invitation to Remedy Deficiencies in the Application Documents Dated Dec. 6, 2013 From the European Patent Office Re. Application No. 11190921.4.
Patent Examination Report Dated Jan. 3, 2014 From the Australian Government, IP Australia Re. Application No. 2008278654.
Patent Examination Report Dated Jul. 28, 2015 From the Australian Government, IP Australia Re. Application No. 2013211502.
Requisition by the Examiner Dated Aug. 5, 2015 From the Canadian Intellectual Property Office Re. Application No. 2,683,143.
Examination Report Dated Oct. 1, 2013 From the Instituto Mexican de la Propiedad Industrial Re. Application No. MX/a/2010/000975 and Its Translation Into English.
International Preliminary Report on Patentability Dated Nov. 14, 2013 From the International Bureau of WIPO Re. Application No. PCT/IL2012/050154.
Applicant-Initiated Interview Summary Dated Nov. 20, 2013 From the US Patent and Trademark Office Re. U.S. Appl. No. 13/125,047.
Requisition by the Examiner Dated Oct. 28, 2013 From the Canadian Intellectual Property Office Re. Application No. 2,570,195.
Lazar et al. "Transforming Growth Factor Alpha: Mutation of Aspartic Acid 47 and Leucine 48 Results in Different Biological Activities", Molecular and Cell Biology, 8(3): 1247-1252, Mar. 1988.
Examination Report Dated Feb. 29, 2016 From the Instituto Mexicano de la Propiedad Industrial, IMPI Re. Application No. MX/a/2013/008592 and Its Translation Into English.
Requisition by the Examiner Dated Apr. 11, 2016 From the Canadian Intellectual Property Office Re. Application No. 2,683,143.
Examination Report Dated Mar. 26, 2014 From the Government of India, Patent Office, Intellectual Property Building Re. Application No. 6582/CHENP/2009.
Examination Report Dated Nov. 26, 2015 From the Instituto Mexicano de la Propiedad Industrial, IMPI Re. Application No. MX/a/2013/008592.

(56) References Cited

OTHER PUBLICATIONS

Translation Dated Jan. 6, 2016 of Examination Report Dated Nov. 26, 2015 From the Instituto Mexicano de la Propiedad Industrial, IMPI Re. Application No. MX/a/2013/008592.
Examination Report Dated May 23, 2013 From the Instituto Mexican de la Propiedad Industrial Re. Application No. MX/a/2011/001741 and Its Translation Into English.
Invitation to Pay Additional Fees Dated Jul. 17, 2013 From the International Searching Authority Re. Application No. PCT/IB2013/054374.
Official Action Dated Sep. 16, 2013 From the US Patent and Trademark Office Re. U.S. Appl. No. 13/125,047.
Translation of Office Action Dated Aug. 28, 2013 From the State Intellectual Property Office of the People's Republic of China Re. Application No. 200880109464.9.
Clontech "Genome Walker™ Universal Kit User Manual", Clontech Laboratories Inc. Cat. No. 638904, PT3042-1 (PR742239), p. 1-30, Apr. 25, 2007.
Zhou et al. "Global Genome Expression Analysis of Rice in Response to Drought and High-Salinity Stresses in Shoot, Flag Leaf, and Panicle", Plant Molecular Biology, 63(5): 591-608, Mar. 2007.

* cited by examiner

POLYNUCLEOTIDES, POLYPEPTIDES AND METHODS FOR INCREASING OIL CONTENT, GROWTH RATE AND BIOMASS OF PLANTS

RELATED APPLICATIONS

This application is a continuation of U.S. patent application Ser. No. 12/594,853 filed on Feb. 25, 2010, which is a National Phase of PCT Patent Application No. PCT/IL2008/000489 having International filing date of Apr. 9, 2008, which claims the benefit of priority of U.S. Provisional Patent Application No. 60/907,568 filed on Apr. 9, 2007. The contents of the above applications are all incorporated herein by reference.

SEQUENCE LISTING STATEMENT

The ASCII file, entitled 56772SequenceListing.txt, created on Jun. 12, 2013, comprising 2,963,456 bytes, submitted concurrently with the filing of this application is incorporated herein by reference.

FIELD AND BACKGROUND OF THE INVENTION

The present invention, in some embodiments thereof, relates to polypeptides, polynucleotides encoding same, transgenic plants expressing same and methods of producing and using same, and, more particularly, but not exclusively, to methods of increasing oil content, seed yield, growth rate, biomass and/or yield of a plant.

Vegetable or seed oils are the major source of energy and nutrition in human and animal diet. They are also used for the production of industrial products, such as paints, inks and lubricants. In addition, plant oils represent renewable sources of long-chain hydrocarbons which can be used as fuel. Since the currently used fossil fuels are finite resources and are gradually being depleted, fast growing biomass crops may be used as alternative fuels or for energy feedstocks and may reduce the dependence on fossil energy supplies. However, the major bottleneck for increasing the consumption of plant oils as bio-fuel is the oil price, which is still higher than fossil fuel [Hypertext Transfer Protocol:// World Wide Web (dot) eia (dot) doe (dot) gov/oiaf/analy-sispaper/biodiesel/; Hypertext Transfer Protocol://World Wide Web (dot) njbiz (dot)com/weekly_article.asp?aID=19755147 (dot) 6122555 (dot) 957931 (dot) 7393254 (dot) 4337383 (dot) 561&aID2=73678]. In addition, the production rate of plant oil is limited by the availability of agricultural land and water. Thus, increasing plant oil yields from the same growing area can effectively overcome the shortage in production space and can decrease vegetable oil prices at the same time.

Studies aiming at increasing plant oil yields focus on the identification of genes involved in oil metabolism as well as in genes capable of increasing plant and seed yields in transgenic plants.

Genes known to be involved in increasing plant oil yields include those participating in fatty acid synthesis or sequestering such as desaturase [e.g., DELTA6, DELTA12 or acyl-ACP (Ssi2; *Arabidopsis* Information Resource (TAIR; Hypertext Transfer Protocol://World Wide Web (dot) *arabidopsis* (dot) org/), TAR No. AT2G43710)], OleosinA (TAR No. AT3G01570) or FAD3 (TAR No. AT2G29980), and various transcription factors and activators such as Lec 1 [TAIR No. AT1G21970, Lotan et al. 1998. *Cell.* 26; 93(7): 1195-205], Lec2 [TAIR No. AT1G28300, Santos Mendoza et al. 2005, FEBS Lett. 579(20:4666-70], Fus3 (TAIR No. AT3G26790), ABI3 [TAIR No. AT3G24650, Lara et al. 2003. J Biol. Chem. 278(23): 21003-11] and Wri1 [TAIR No. AT3G54320, Cernac and Benning, 2004. Plant J. 40(4): 575-85].

Zabrouskov V., et al., 2002 (Physiol Plant. 116:172-185) demonstrated that upregulation of endoplasmic reticulum (FAD3) and plastidal (FAD7) fatty acid desaturases in potato increases the total lipid fraction in transgenic clones.

Wang H W et al., 2007 (Plant J. 52:716-29. Epub 2007 Sep. 18) found that transgenic plant seeds over-expressing the GmD of4 and GmD of11 transcription factors exhibit increased content of total fatty acids and lipids.

Vigeolas H, et al. [Plant Biotechnol J. 2007, 5(3):431-41] and U.S. Pat. Appl. No. 20060168684 disclose increased seed oil content in oil-seed rape (*Brassica napus* L.) by over-expression of a yeast glycerol-3-phosphate dehydrogenase under the control of a seed-specific promoter.

Katavic V, et al., 2000 (Biochem Soc Trans. 28:935-7) describe the use of the *Arabidopsis* FAE1 and yeast SLC1-1 genes for improvements in erucic acid and oil content in rapeseed.

U.S. Pat. Appl. No. 20080076179 discloses an isolated moss nucleic acid encoding a lipid metabolism protein (LMP) and transgenic plants expressing same with increased lipid levels.

U.S. Pat. Appl. No. 20060206961 discloses a method of increasing oil content in plants (e.g., in plant seeds), by expressing in the plant the Ypr140w polypeptide.

U.S. Pat. Appl. No. 20060174373 discloses a method of increasing oil content in plants by expressing a nucleic acid encoding a triacylglycerols (TAG) synthesis enhancing protein (TEP) in the plant.

U.S. Pat. Appl. Nos. 20070169219, 20070006345, 20070006346 and 20060195943, disclose transgenic plants with improved nitrogen use efficiency which can be used for the conversion into fuel or chemical feedstocks.

SUMMARY OF THE INVENTION

According to an aspect of some embodiments of the present invention there is provided a method of increasing oil content, growth rate, biomass, yield and/or vigor of a plant, comprising introducing into the plant an exogenous polynucleotide encoding a polypeptide comprising an amino acid sequence at least 90% homologous to the amino acid sequence selected from the group consisting of SEQ ID NOs: 199, 166-198, 200-221, 229-307, 311-330, 351-353, 355-361, 363-364, 366-368, 218, 222-228, 308-310, 350, 354, 362, 365, 523-649, 786-920, 1047 and 1048, thereby increasing the oil content, growth rate, biomass, yield and/or vigor of the plant.

According to an aspect of some embodiments of the present invention there is provided a method of producing oil, comprising: (a) providing the plant according to the method of the invention, and (b) extracting the oil from the plant; thereby producing the oil.

According to an aspect of some embodiments of the present invention there is provided an isolated polynucleotide comprising a nucleic acid sequence at least 90% identical to SEQ ID NOs: 34, 1-33, 35-52, 54-56, 64-165, 332-334, 336-342, 344-345, 347-349, 53, 57-63, 143-145, 331, 335, 343, 346, 369-522, 650-785, 1016-1046.

According to an aspect of some embodiments of the present invention there is provided a nucleic acid construct, comprising the isolated polynucleotide of the invention and a promoter for directing transcription of the nucleic acid sequence.

According to an aspect of some embodiments of the present invention there is provided an isolated polypeptide, comprising an amino acid sequence at least 90% homologous to SEQ ID NO: 199, 166-198, 200-221, 229-307, 311-330, 351-353, 355-361, 363-364, 366-368, 218, 222-228, 308-310, 350, 354, 362, 365, 523-649, 786-920, 1047 and 1048.

According to an aspect of some embodiments of the present invention there is provided a plant cell exogenously expressing the polypeptide of the invention.

According to an aspect of some embodiments of the present invention there is provided a plant cell exogenously expressing the polynucleotide of the invention.

According to some embodiments of the invention, the polynucleotide comprises a nucleic acid sequence selected from the group consisting of SEQ ID NOs: 34, 1-33, 35-52, 54-56, 64-165, 332-334, 336-342, 344-345, 347-349, 53, 57-63, 143-145, 331, 335, 343, 346, 369-522, 650-785, 1016-1046.

According to some embodiments of the invention, the amino acid sequence is selected from the group consisting of SEQ ID NOs: 199, 166-198, 200-221, 229-307, 311-330, 351-353, 355-361, 363-364, 366-368, 218, 222-228, 308-310, 350, 354, 362, 365, 523-649, 786-920, 1047 and 1048.

According to some embodiments of the invention, the polynucleotide is selected from the group consisting of SEQ ID NOs: 34, 1-33, 35-52, 54-56, 64-165, 332-334, 336-342, 344-345, 347-349, 53, 57-63, 143-145, 331, 335, 343, 346, 369-522, 650-785, 1016-1046.

According to some embodiments of the invention, the polypeptide is selected from the group consisting of SEQ ID NOs: 199, 166-198, 200-221, 229-307, 311-330, 351-353, 355-361, 363-364, 366-368, 218, 222-228, 308-310, 350, 354, 362, 365, 523-649, 786-920, 1047 and 1048.

According to some embodiments of the invention, the oil comprises a seed oil.

According to some embodiments of the invention, the oil comprises a vegetative portion oil.

According to some embodiments of the invention, the plant cell forms a part of a plant.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to isolated polypeptides and polynucleotides encoding same, and more particularly, but not exclusively, to methods of using same for increasing oil content, growth rate, yield, biomass and/or vigor of a plant.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. While reducing the present invention to practice, the present inventors have identified novel polypeptides and polynucleotides which can be used to increase oil content, seed yield, growth rate, biomass, yield and/or vigor of a plant.

Figure 3:
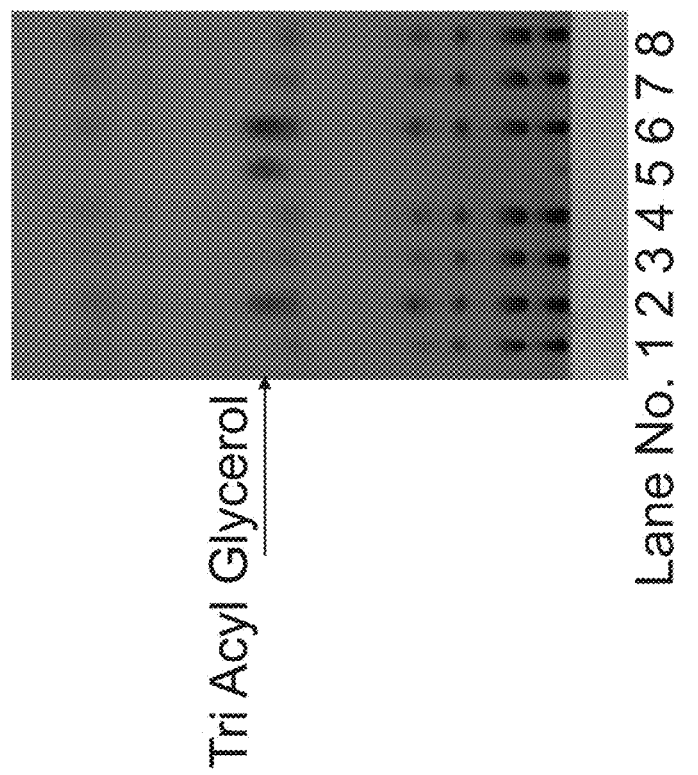
FIG. 3 is an image depicting iodine vapor staining of lipids isolated from the transgenic plants expressing the genes listed in Table 56, Example 7 of the Examples section which follows. The arrow points at the tri acyl glycerol bands.

Thus, as shown in the Examples section which follows, the present inventors have employed a bioinformatics approach which compares the expression pattern of *Arabidopsis*-derived genes in 79 tissues or developmental stages to that of the oil hook genes (OHGs) known to play a role in embryogenesis, seed development and oil synthesis and accumulation, and genes exhibiting a significant correlation were identified (Table 1, Example 1). In addition, using an oligonucleotide micro-array, the present inventors determined the expression profile of identified genes in tissues and developmental stages of various *Arabidopsis* ecotypes (Table 3; Example 2) and correlated the expression profile to selected yield or vigor related parameters (Tables 4, 5 and 6; Example 2). Genes exhibiting a significant correlation between the expression profile and the yield or vigor parameters of the ecotypes were identified (Table 7; Example 2). Of them, several genes were found to modulate seed yield (Table 8), oil yield (Table 9), growth rate (Table 10), organ shape/size/length (Table 11), harvest index (Table 12), oil content per seed (Table 13), plant dry matter (Table 14) and seed number per silique (Table 15). Additional genes which are predicted to increase oil content, seed yield, growth rate, yield and/or biomass of a plant were identified using bioinformatics tools (Table 2, Example 1). In addition, polypeptides and polynucleotides encoding same which are homologous to the predicted polypeptides of Tables 1 and 2 were also identified (Table 18, Example 5). Furthermore, as described in Examples 3, 4 and 6 of the Examples section which follows, transgenic plants expressing the identified polynucleotides exhibit increased seed yield, oil yield, dry matter, harvest index, growth rate, rosette area, oil percentage in seed and weight of 1000 seeds (Tables 19-55; Example 6). In addition, transgenic plants expressing the polynucleotides of the invention exhibited increased oil content as compared to control plants (FIG. 3, Example 7). Altogether, these results suggest the use of the novel polynucleotides and polypeptides of the invention for increasing oil content, yield (including seed yield), growth rate, biomass, and/or vigor of a plant.

It should be noted that since oil content is affected by intrinsic oil production, or mass/size of oil producing tissue per plant/per growth period, any gene which affects these aforementioned processes is contemplated in accordance with the teachings of the present invention.

Thus, according to one aspect of the invention there is provided a method of increasing oil content, yield, growth rate, biomass and/or vigor of a plant. The method is effected by introducing into the plant an exogenous polynucleotide encoding a polypeptide comprising an amino acid sequence at least 90% homologous to the amino acid sequence selected from the group consisting of SEQ ID NOs:166-221, 229-307, 311-330, 351-353, 355-361, 363-364, 366-368, 218, 222-228, 308-310, 350, 354, 362, 365, 523-649, 786-920, 1047 and 1048.

The phrase "oil content" as used herein refers to the amount of lipids in a given plant organ, either the seeds (seed oil content) or the vegetative portion of the plant (vegetative oil content) and typically expressed as percentage of dry weight (10% humidity of seeds) or wet weight (for vegetative portion).

As mentioned, in one embodiment, increase in oil content of the plant can be achieved by increasing the size/mass of a plant's tissue(s) which comprise oil per growth period. Thus, increased oil content of a plant can be achieved by increasing the yield, growth rate, biomass and vigor of the plant.

As used herein the phrase "plant yield" refers to the amount (as determined by weight/size) or quantity (numbers) of tissue (e.g., seed, referred to "seed yield" and vegetative portion) produced per plant or per growing season. Hence increased yield could affect the economic benefit one can obtain from the plant in a certain growing area and/or growing time.

As used herein the phrase "plant biomass" refers to the amount (measured in grams of air-dry tissue) of a tissue produced from the plant in a growing season, which could also determine or affect the plant yield or the yield per growing area.

As used herein the phrase "plant vigor" refers to the amount (measured by weight) of tissue produced by the plant in a given time. Hence increase vigor could determine or affect the plant yield or the yield per growing time or growing area.

As used herein the term "increasing" refers to at least about 2%, at least about 3%, at least about 4%, at least about 5%, at least about 10%, at least about 15%, at least about 20%, at least about 30%, at least about 40%, at least about 50%, at least about 60%, at least about 70%, at least about 80%, increase in plant oil content, seed yield (seed yield per plant and/or seed yield per growing area), plant yield, growth rate, biomass, and/or vigor as compared to a native plant [i.e., a plant not modified with the biomolecules (polynucleotide or polypeptides) of the invention, e.g., a non-transformed plant of the same species which is grown under the same growth conditions).

As used herein, the phrase "exogenous polynucleotide" refers to a heterologous nucleic acid sequence which may not be naturally expressed within the plant or which overexpression in the plant is desired. The exogenous polynucleotide may be introduced into the plant in a stable or transient manner, so as to produce a ribonucleic acid (RNA) molecule and/or a polypeptide molecule. It should be noted that the exogenous polynucleotide may comprise a nucleic acid sequence which is identical or partially homologous to an endogenous nucleic acid sequence of the plant.

According to some embodiments of the invention, the exogenous polynucleotide encodes a polypeptide comprising an amino acid sequence at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more say 100% homologous to the amino acid sequence selected from the group consisting of SEQ ID NOs:166-221, 229-307, 311-330, 351-353, 355-361, 363-364, 366-368, 218, 222-228, 308-310, 350, 354, 362, 365, 523-649, 786-920, 1047 and 1048.

Homology (e.g., percent homology) can be determined using any homology comparison software, including for example, the BlastP or TBLASTN softwares of the National Center of Biotechnology Information (NCBI) such as by using default parameters, when starting from a polypeptide sequence; or the tBLASTX algorithm (available via the NCBI) such as by using default parameters, which compares the six-frame conceptual translation products of a nucleotide query sequence (both strands) against a protein sequence database.

Homologous sequences include both orthologous and paralogous sequences. The term "paralogous" relates to gene-duplications within the genome of a species leading to paralogous genes. The term "orthologous" relates to homologous genes in different organisms due to ancestral relationship.

One option to identify orthologues in monocot plant species is by performing a reciprocal blast search. This may be done by a first blast involving blasting the sequence-of-interest against any sequence database, such as the publicly available NCBI database which may be found at: Hypertext Transfer Protocol://World Wide Web (dot) ncbi (dot) nlm (dot) nih (dot) gov. If orthologues in rice were sought, the sequence-of-interest would be blasted against, for example, the 28,469 full-length cDNA clones from Oryza sativa Nipponbare available at NCBI. The blast results may be filtered. The full-length sequences of either the filtered results or the non-filtered results are then blasted back (second blast) against the sequences of the organism from which the sequence-of-interest is derived. The results of the first and second blasts are then compared. An orthologue is identified when the sequence resulting in the highest score (best hit) in the first blast identifies in the second blast the query sequence (the original sequence-of-interest) as the best hit. Using the same rational a paralogue (homolog to a gene in the same organism) is found. In case of large sequence families, the ClustalW program may be used [Hypertext Transfer Protocol://World Wide Web (dot) ebi (dot) ac (dot) uk/Tools/clustalw2/index (dot) html], followed by a neighbor-joining tree (Hypertext Transfer Protocol://en (dot) wikipedia (dot) org/wiki/Neighbor-joining) which helps visualizing the clustering.

According to some embodiments of the invention, the exogenous polynucleotide encodes a polypeptide selected from the group consisting of SEQ ID NOs:166-221, 229-307, 311-330, 351-353, 355-361, 363-364, 366-368, 218, 222-228, 308-310, 350, 354, 362, 365, 523-649, 786-920, 1047 and 1048.

According to some embodiments of the invention the exogenous polynucleotide comprises a nucleic acid sequence which is at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to a nucleic acid sequence selected from the group consisting of SEQ ID NOs:1-52, 54-56, 64-165, 332-334, 336-342, 344-345, 347-349, 53, 57-63, 143-145, 331, 335, 343, 346, 369-522, 650-785, 1016-1046.

Identity (e.g., percent homology) can be determined using any homology comparison software, including for example, the BlastN software of the National Center of Biotechnology Information (NCBI) such as by using default parameters.

According to some embodiments of the invention the exogenous polynucleotide is set forth by SEQ ID NOs:1-52, 54-56, 64-165, 332-334, 336-342, 344-345, 347-349, 53, 57-63, 143-145, 331, 335, 343, 346, 369-522, 650-785, 1016-1046.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Nucleic acid sequences encoding the polypeptides of the present invention may be optimized for expression. Non-limiting examples of optimized nucleic acid sequences are provided in SEQ ID NOs:1040, 1041, 1042, 1043, 1044, 1045, and 1046 which encodes polypeptides comprising the amino acid sequences set forth by SEQ ID NOs: 167, 169, 1047, 181, 185, 189 and 196, respectively. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N [(Xn−Yn)/Yn]2/N, where Xn refers to the frequency of usage of codon n in highly expressed plant genes, where Yn to the frequency of usage of codon n in the gene of interest and N refers to the total number of codons in the gene of interest. A Table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiological Sciences) DNA bank in Japan (http://www.kazusa.or.jp/codon/). The Codon Usage Database contains codon usage tables for a number of different species, with each codon usage table having been statistically determined based on the data present in Genbank.

By using the above Tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

According to some embodiments of the invention, expression of the polynucleotide of the invention results in down-regulation of the expression level or activity of the corresponding endogenous polypeptide (e.g., homologue).

According to some embodiments of the invention, the exogenous polynucleotide is used for co-suppression or sense suppression of an endogenous polypeptide. Thus, introducing the exogenous polynucleotide to the plant cells results in transcription of an RNA molecule (in a sense direction with respect to the corresponding endogenous gene) which suppresses translation of the corresponding endogenous RNA molecule, such as described in U.S. Pat. No. 5,231,020 to Jorgensen, which is fully incorporated herein by reference. For co-suppression, the exogenous polynucleotide does not require the entire nucleic acid sequence of the corresponding endogenous gene, nor does it require that the introduced sequence be exactly identical to the endogenous gene. However, as with antisense suppression, the suppressive efficiency is enhanced as specificity of hybridization is increased, e.g., as the introduced sequence is lengthened, and/or as the sequence similarity between the introduced sequence and the endogenous gene is increased. For further details see U.S. Pat. Appl. No. 20050172364 which is fully incorporated herein by reference.

According to some embodiments of the invention, the exogenous polynucleotide comprises an untranslatable nucleic acid sequence, e.g., a sequence comprising one or more pre-mature stop codons, or nonsense mutations, such as described in U.S. Pat. No. 5,583,021.

Thus, the invention encompasses isolated polynucleotides described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

As mentioned, the present inventors have uncovered previously uncharacterized polypeptides.

Thus, the invention provides an isolated polypeptide having an amino acid sequence at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to an amino acid sequence selected from the group consisting of SEQ ID NOs:166-221, 229-307, 311-330, 351-353, 355-361, 363-364, 366-368, 218, 222-228, 308-310, 350, 354, 362, 365, 523-649, 786-920, 1047 and 1048.

According to some embodiments of the invention, there is provided an exogenous polypeptide selected from the group consisting of SEQ ID NOs:166-221, 229-307, 311-330, 351-353, 355-361, 363-364, 366-368, 218, 222-228, 308-310, 350, 354, 362, 365, 523-649, 786-920, 1047 and 1048.

The invention also encompasses fragments of the above described polypeptides and polypeptides having mutations, such as deletions, insertions or substitutions of one or more amino acids, either naturally occurring or man induced, either randomly or in a targeted fashion.

The term "plant" as used herein encompasses whole plants, ancestors and progeny of the plants and plant parts, including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising Acacia spp., Acer spp., Actinidia spp., Aesculus spp., Agathis australis, Albizia amara, Alsophila tricolor, Andropogon spp., Arachis spp, Areca catechu, Astelia fragrans, Astragalus cicer, Baikiaea plurijuga, Betula spp., Brassica spp., Bruguiera gymnorrhiza, Burkea africana, Butea frondosa, Cadaba farinosa, Calliandra spp, Camellia sinensis, Canna indica, Capsicum spp., Cassia spp., Centroema pubescens, Chacoomeles spp., Cinnamomum cassia, Coffea arabica, Colophospermum mopane, Coronillia varia, Cotoneaster serotina, Crataegus spp., Cucumis spp., Cupressus spp., Cyathea dealbata, Cydonia oblonga, Cryptomeria japonica, Cymbopogon spp., Cynthea dealbata, Cydonia oblonga, Dalbergia monetaria, Davallia divaricata, Desmodium spp., Dicksonia squarosa, Dibeteropogon amplectens, Dioclea spp, Dolichos spp., Dorycnium rectum, Echinochloa pyramidalis, Ehraffia spp., Eleusine coracana, Eragrestis spp., Erythrina spp., Eucalypfus spp., Euclea schimperi, Eulalia vi/losa, Pagopyrum spp., Feijoa sellowlana, Fragaria spp., Flemingia spp, Freycinetia banksli, Geranium thunbergii, GinAgo biloba, Glycine javanica, Gliricidia spp, Gossypium hirsutum, Grevillea spp., Guibourtia coleosperma, Hedysarum spp., Hemaffhia altissima, Heteropogon contoffus, Hordeum vulgare, Hyparrhenia rufa, Hypericum erectum, Hypeffhelia dissolute, Indigo incamata, Iris spp., Leptarrhena pyrolifolia, Lespediza spp., Lettuca spp., Leucaena leucocephala, Loudetia simplex, Lotonus bainesli, Lotus spp., Macrotyloma axillare, Malus spp., Manihot esculenta, Medicago saliva, Metasequoia glyptostroboides, Musa sapientum, Nicotianum spp., Onobrychis spp., Ornithopus spp., Oryza spp., Peltophorum africanum, Pennisetum spp., Persea gratissima, Petunia spp., Phaseolus spp., Phoenix canariensis, Phormium cookianum, Photinia spp., Picea glauca, Pinus spp., Pisum sativam, Podocarpus totara, Pogonarthria fleckii, Pogonaffhria squarrosa, Populus spp., Prosopis cineraria, Pseudotsuga menziesii, Pterolobium stellatum, Pyrus communis, Quercus spp., Rhaphiolepsis umbellata, Rhopalostylis sapida, Rhus natalensis, Ribes grossularia, Ribes spp., Robinia pseudoacacia, Rosa spp., Rubus spp., Salix spp., Schyzachyrium sanguineum, Sciadopitys vefficillata, Sequoia sempervirens, Sequoiadendron giganteum, Sorghum bicolor, Spinacia spp., Sporobolus fimbriatus, Stiburus alopecuroides, Stylosanthos humilis, Tadehagi spp, Taxodium distichum, Themeda triandra, Trifolium spp., Triticum spp., Tsuga heterophylla, Vaccinium spp., Vicia spp., Vitis vinifera, Watsonia pyramidata, Zantedeschia aethiopica, Zea mays, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barely, rye, oat, peanut, pea, lentil and alfalfa, cotton, rapeseed, canola, pepper, sunflower, tobacco, eggplant, eucalyptus, a tree, an ornamental plant, a perennial grass and a forage crop. Alternatively algae and other non-Viridiplantae can be used for the methods of the present invention.

According to some embodiments of the invention, the oil producing plant can be oilseed crops, soybeans, sunflower, *Brassica napus, Brassica Juncea, zea* maize, cotton, olive (*Olea europaea*), flax, *Brassica nigra, Jatropha curcas*, and Castorbean (*Ricinus communis*).

Introducing the exogenous polynucleotide of the invention into the plant can be effected by transforming one or more cells of the plant with the exogenous polynucleotide, followed by generating a mature plant from the transformed cells and cultivating the mature plant under conditions suitable for expressing the exogenous polynucleotide within the mature plant.

According to some embodiments of the invention, the transformation is effected by introducing to the plant cell a nucleic acid construct which includes the exogenous polynucleotide of some embodiments of the invention and at least one promoter capable of directing transcription of the exogenous polynucleotide in the plant cell. Further details of suitable transformation approaches are provided hereinbelow.

As used herein, the term "promoter" refers to a region of DNA which lies upstream of the transcriptional initiation site of a gene to which RNA polymerase binds to initiate transcription of RNA. The promoter controls where (e.g., which portion of a plant) and/or when (e.g., at which stage or condition in the lifetime of an organism) the gene is expressed.

Any suitable promoter sequence can be used by the nucleic acid construct of the present invention. According to some embodiments of the invention, the promoter is a constitutive promoter, a tissue-specific, or a developmental or embryonic-specific promoter.

Suitable constitutive promoters include, for example, CaMV 35S promoter (SEQ ID NO:921; Odell et al., Nature 313:810-812, 1985); *Arabidopsis* At6669 promoter (SEQ ID NO:1015; see PCT Publication No. WO2004/104162); maize Ubi 1 (Christensen et al., Plant Sol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al, Plant J November;2(6): 837-44, 1992); Rice cyclophilin (Bucholz et al, Plant Mol. Biol. 25(5):837-43, 1994); Maize H3 histone (Lepetit et al, Mol. Gen. Genet. 231: 276-285, 1992); Actin 2 (An et al, Plant J. 10(1); 107-121, 1996) and Synthetic Super MAS (Ni et al., The Plant Journal 7: 661-76, 1995). Other constitutive promoters include those in U.S. Pat. Nos. 5,659,026, 5,608, 149; 5,608,144; 5,604,121; 5,569,597: 5,466,785; 5,399, 680; 5,268,463; and 5,608,142.

Suitable tissue-specific promoters include, but not limited to, seed-preferred promoters [e.g., from seed specific genes (Simon, et al., Plant Mol. Biol. 5. 191, 1985; Scofield, et al., J. Biol. Chem. 262: 12202, 1987; Baszczynski, et al., Plant Mol. Biol. 14: 633, 1990), Brazil Nut albumin (Pearson' et al., Plant Mol. Biol. 18: 235-245, 1992), legumin (Ellis, et al. Plant Mol. Biol. 10: 203-214, 1988), Glutelin (rice) (Takaiwa, et al., Mol. Gen. Genet. 208: 15-22, 1986; Takaiwa, et al., FEBS Letts. 221: 43-47, 1987), Zein (Matzke et al Plant Mol Biol, 143: 323-32 1990), napA (Stalberg, et al, Planta 199: 515-519, 1996), Wheat SPA (Albanietal, Plant Cell, 9: 171-184, 1997), sunflower oleosin (Cummins, et al., Plant Mol. Biol. 19: 873-876, 1992)], leaf-specific promoters [such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993], endosperm specific promoters [e.g., wheat LMW and HMW, glutenin-1 (Mol Gen Genet. 216: 81-90, 1989; NAR 17:461-2), wheat a, b and g gliadins (EMB03:1409-15, 1984), Barley ltrl promoter, barley B1, C, D hordein (Theor Appl Gen 98:1253-62, 1999; Plant J 4:343-55, 1993; Mol Gen Genet. 250:750-60, 1996), Barley DOF (Mena et al, The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin Glb-1 (Wu et al, Plant Cell Physiology 39(8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorgum gamma-kafirin (PMB 32:1029-35, 1996)], embryo specific promoters [e.g., rice OSH1 (Sato et al, Proc. Natl. Acad. Sci. USA, 93: 8117-8122), KNOX (Postma-Haarsma of al, Plant Mol. Biol. 39:257-71, 1999), rice oleosin (Wu et at, J. Biochem., 123:386, 1998)], and flower-specific promoters [e.g., AtPRP4, chalene synthase (chsA) (Van der Meer, et al., Plant Mol. Biol. 15, 95-109, 1990), LAT52 (Twell et al Mol. Gen. Genet. 217:240-245; 1989), apetala-3].

The nucleic acid construct of some embodiments of the invention can further include an appropriate selectable marker and/or an origin of replication. According to some embodiments of the invention, the nucleic acid construct utilized is a shuttle vector, which can propagate both in *E. coli* (wherein the construct comprises an appropriate selectable marker and origin of replication) and be compatible with propagation in cells. The construct according to the present invention can be, for example, a plasmid, a bacmid, a phagemid, a cosmid, a phage, a virus or an artificial chromosome.

The nucleic acid construct of some embodiments of the invention can be utilized to stably or transiently transform plant cells. In stable transformation, the exogenous polynucleotide is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S, and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

According to some embodiments of the invention, the transgenic plants are generated by transient transformation of leaf cells, meristematic cells or the whole plant.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants are described in WO 87/06261.

According to some embodiments of the invention, the virus used for transient transformations is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous polynucleotide sequences such as those included in the construct of the present invention is demonstrated by the above references as well as in U.S. Pat. No. 5,316,931.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression.

A technique for introducing exogenous polynucleotide sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the exogenous polynucleotide includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Since increasing of the oil content, yield, biomass, growth rate and/or vigor in plants can involve multiple genes acting additively or in synergy (see, for example, in Quesda et al., Plant Physiol. 130:951-063, 2002), the invention also envisages expressing a plurality of exogenous polynucleotides in a single host plant to thereby achieve superior increase of oil content, yield, biomass, growth rate and/or vigor in plants.

Expressing a plurality of exogenous polynucleotides in a single host plant can be effected by co-introducing multiple nucleic acid constructs, each including a different exogenous polynucleotide, into a single plant cell. The transformed cell can then be regenerated into a mature plant using the methods described hereinabove.

Alternatively, expressing a plurality of exogenous polynucleotides in a single host plant can be effected by co-introducing into a single plant-cell a single nucleic-acid construct including a plurality of different exogenous polynucleotides. Such a construct can be designed with a single promoter sequence which can transcribe a polycistronic messager RNA including all the different exogenous polynucleotide sequences. To enable co-translation of the different polypeptides encoded by the polycistronic messenger RNA, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the different polypeptides described above will be translated from both the capped 5' end and the two internal IRES sequences of the polycistronic RNA molecule to thereby produce in the cell all different polypeptides. Alternatively, the construct can include several promoter sequences each linked to a different exogenous polynucleotide sequence. The plant cell transformed with the construct including a plurality of different exogenous polynucleotides, can be regenerated into a mature plant, using the methods described hereinabove.

Alternatively, expressing a plurality of exogenous polynucleotides in a single host plant can be effected by introducing different nucleic acid constructs, including different exogenous polynucleotides into a plurality of plants. The regenerated transformed plants can then be cross-bred and resultant progeny selected for superior oil content, growth rate, biomass, yield and/or vigor, using conventional plant breeding techniques.

Thus, the invention encompasses plants exogenously expressing (as described above) the polynucleotide(s) and/or polypeptide(s) of the invention. Once expressed within the plant cell or the entire plant, the level of the polypeptide encoded by the exogenous polynucleotide can be determined by methods well known in the art such as, activity assays, Western blots using antibodies capable of specifically binding the polypeptide, Enzyme-Linked ImmunoSorbent Assay (ELISA), radio-immuno-assays (RIA), immunohistochemistry, immunofluorescence and the like.

Methods of determining the level in the plant of the RNA transcribed from the exogenous polynucleotide are well known in the art and include, for example, Northern blot analysis, reverse transcription polymerase chain reaction (RT-PCR) analysis (including quantitative, semi-quantitative or real-time RT-PCR) and RNA-in situ hybridization.

The polynucleotides and polypeptides described hereinabove can be used in a wide range of economical plants, in a safe and cost effective manner.

The effect of the transgene (the exogenous polynucleotide encoding the polypeptide) on oil content, plant yield, seed yield, biomass, growth rate and/or vigor can be determined using known methods.

The oil content of a plant can be determined by extraction of the oil from the seed or the vegetative portion of the plant. Briefly, lipids (oil) can be removed from the plant (e.g., seed) by grinding the plant tissue in the presence of specific solvents (e.g., hexane or petroleum ether) and extracting the oil in a continuous extractor. Indirect oil content analysis can be carried out using various known methods such as Nuclear Magnetic Resonance (NMR) Spectroscopy, which measures the resonance energy absorbed by hydrogen atoms in the liquid state of the sample [See for example, Conway T F. and Earle F R., 1963, Journal of the American Oil Chemists' Society; Springer Berlin/Heidelberg, ISSN: 0003-021X (Print) 1558-9331 (Online)]; the Near Infrared (NI) Spectroscopy, which utilizes the absorption of near infrared energy (1100-2500 nm) by the sample; and a method described in WO/2001/023884, which is based on extracting oil a solvent, evaporating the solvent in a gas stream which forms oil particles, and directing a light into the gas stream and oil particles which forms a detectable reflected light. Another method of determining oil content is described in Example 7 of the Examples section which follows.

The plant vigor can be calculated by the increase in growth parameters such as leaf area, rosette diameter, plant fresh weight and the like per time.

The growth rate can be measured using digital analysis of growing plants. For example, images of plants growing in greenhouse on plot basis can be captured every 3 days and the rosette area can be calculated by digital analysis. Rosette area growth is calculated using the difference of rosette area between days of sampling divided by the difference in days between samples.

Measurements of seed yield can be done by collecting the total seeds from 8-16 plants together, weighting them using analytical balance and dividing the total weight by the number of plants. Seed per growing area can be calculated in the same manner while taking into account the growing area given to a single plant. Increase seed yield per growing area could be achieved by increasing seed yield per plant, and/or by increasing number of plants capable of growing in a given area.

Evaluation of the seed yield per plant can be done by measuring the amount (weight or size) or quantity (i.e., number) of dry seeds produced and harvested from 8-16 plants and divided by the number of plants.

Evaluation of growth rate can be done by measuring plant biomass produced, rosette area, leaf size or root length per time (can be measured in $cm^2$ per day of leaf area).

Thus, the present invention is of high agricultural value for promoting the yield of commercially desired crops (e.g., seeds).

Any of the transgenic plants described hereinabove or parts thereof may be processed to produce a feed, meal, protein or oil preparation, such as for ruminant animals.

The transgenic plants described hereinabove, which exhibit an increased oil content can be used to produce plant oil (by extracting the oil from the plant).

The plant oil (including the seed oil and/or the vegetative portion oil) produced according to the method of the invention may be combined with a variety of other ingredients. The specific ingredients included in a product are determined according to the intended use. Exemplary products include animal feed, raw material for chemical modification, biodegradable plastic, blended food product, edible oil, biofuel, cooking oil, lubricant, biodiesel, snack food, cosmetics, and fermentation process raw material. Exemplary products to be incorporated to the plant oil include animal feeds, human food products such as extruded snack foods, breads, as a food binding agent, aquaculture feeds, fermentable mixtures, food supplements, sport drinks, nutritional food bars, multi-vitamin supplements, diet drinks, and cereal foods.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Gene Identification and Gene Role Prediction Using Bioinformatics Tools

Genes encoding polypeptides, suitable for increasing seed oil and seed yield were identified by in-depth analysis of RNA expression profiles, sequence similarities, gene annotations, biochemical pathways, DNA, ESTs, protein and expression databases deposited in the internet.

Bioinformatics Tools

In-Silico gene identification—To identify novel genes which could greatly affect seed oil yield, *Arabidopsis* genes, already found to play key role in embryogenesis, seed development and oil synthesis and accumulation were identified in the literature ('oil hook genes'—OHGs). OHGs number is according to TAIR website [Hypertext Transfer Protocol://World Wide Web (dot) *arabidopsis* (dot) org/] and includes all information on the OHGs. OHGs include wild-type alleles of Ssi2 (AT2G43710), OleosinA (AT3G01570), Lec1 (AT1G21970), Lec2 (AT1G28300), Fus3 (AT3G26790), FAD3 (AT2G29980), ABI3 (AT3G24650) and Wri1 (AT3G54320). Comparison of gene expression profile in 79 different developmental stages of *Arabidopsis* was done on the OHGs genes and all other genes printed on the Nottingham *Arabidopsis* Stock Centre [(NASC), Hypertext Transfer Protocol://affymetrix (dot) *arabidopsis* (dot) info/)] micro-arrays describing anatomy, development and various stress experiments. Correlation was determined using the Pearson correlation statistic analysis [Hypertext Transfer Protocol://davidmlane (dot) com/hyperstat/A34739 (dot) html].

The criteria used for each of the genes are described in detail in Table 1 below and cover a variety of biological rationales that use various bioinformatics approaches. The genes were selected to cause changes in seed size and/or seed oil yield based on their highest expression correlation (given as Pearson R values between $0.7<R<1$) to one or more of the OHGs. The list of genes identified and their correlation (R value) to each of the OHGs are provided in Table 1, hereinbelow.

TABLE 1

| Serial No | Nucl. SEQ ID NO: | Prot. SEQ ID NO: | BDL No | TAIR-gene name | R wri1 | R abi3 | R fus3 | R oleosin A | R ssi2 | R fad3 | R lec1 | R lec2 |
|---|---|---|---|---|---|---|---|---|---|---|---|---|
| 1 | 1 | 166 | 3 | AT5G50770 | | 0.891 | 0.986 | 0.897 | 0.791 | 0.882 | | |
| 2 | 2 | 167 | 1 | AT1G65090 | | 0.995 | 0.921 | 0.997 | 0.715 | 0.902 | | |
| 3 | 3 | 168 | 2 | AT1G34580 | | | | | | | 0.955 | 0.915 |
| 4 | 4 | 169 | 4 | AT2G45420 | 0.933 | | 0.893 | 0.713 | 0.74 | 0.716 | 0.759 | 0.76 |
| 5 | 5 | 170 | 5 | AT3G14360 | | 0.969 | 0.96 | 0.97 | 0.731 | 0.914 | | |
| 6 | 6 | 171 | 6 | AT4G10490 | 0.912 | | 0.88 | 0.725 | 0.76 | 0.71 | 0.757 | 0.755 |
| 7 | 7 | 172 | 7 | AT5G51490 | 0.901 | 0.722 | 0.92 | 0.745 | 0.79 | 0.797 | | |
| 8 | 8 | 173 | 8 | AT3G03240 | | 0.947 | 0.982 | 0.956 | 0.775 | 0.912 | | |
| 9 | 9 | 174 | 9 | AT5G24130 | | 0.988 | 0.917 | 0.987 | | 0.91 | | |
| 10 | 10 | 175 | 10 | AT5G09640 | 0.719 | 0.905 | 0.98 | 0.91 | 0.8 | 0.908 | | |
| 11 | 11 | 176 | 11 | AT5G12460 | 0.815 | | | | | | 0.969 | 0.911 |
| 12 | 12 | 177 | 12 | AT4G08530 | | | | | | | 0.931 | 0.919 |
| 13 | 13 | 178 | 14 | AT1G53690 | 0.931 | | 0.792 | | 0.74 | | | |
| 14 | 14 | 179 | 15 | AT1G68510 | 0.905 | | | | | | 0.938 | 0.913 |
| 15 | 15 | 180 | 16 | AT5G03800 | 0.8 | 0.878 | 0.966 | 0.894 | 0.797 | 0.882 | | |
| 16 | 16 | 181 | 17 | AT5G36770 | | | | | | | 0.922 | 0.921 |
| 17 | 17 | 182 | 18 | AT5G40420 | | 0.997 | 0.894 | 0.9996 | | 0.886 | | |
| 18 | 18 | 183 | 19 | AT2G02080 | | 0.702 | 0.741 | 0.72 | 0.748 | | | |
| 19 | 19 | 184 | 20a | AT1G47540.1 | | 0.993 | 0.915 | 0.995 | 0.71 | 0.892 | | |
| 20 | 20 | 185 | 20b | AT1G47540.2 | | 0.993 | 0.915 | 0.995 | 0.71 | 0.892 | | |
| 21 | 21 | 186 | 21 | AT3G62730 | | 0.995 | 0.92 | 0.993 | 0.711 | 0.903 | | |
| 22 | 22 | 187 | 22 | AT2G27380 | | 0.995 | 0.873 | 0.997 | | 0.875 | | |
| 23 | 23 | 188 | 23 | AT3G27785 | 0.939 | | | | | | 0.867 | 0.81 |
| 24 | 24 | 189 | 2991 | AT5G15000 | | 0.955 | 0.959 | 0.957 | 0.739 | 0.902 | | |
| 25 | 25 | 190 | 25 | AT3G20910 | | 0.963 | 0.943 | 0.962 | | 0.883 | | |
| 26 | 26 | 191 | 26a | AT1G11170.1 | | 0.926 | 0.981 | 0.929 | 0.765 | 0.894 | | |
| 27 | 27 | 192 | 26b | AT1G11170.2 | | 0.926 | 0.981 | 0.929 | 0.765 | 0.894 | | |
| 28 | 28 | 193 | 27 | AT1G68380 | | 0.97 | 0.965 | 0.977 | 0.77 | 0.92 | | |
| 29 | 29 | 194 | 28 | AT1G09380 | 0.705 | 0.899 | 0.95 | 0.91 | 0.756 | 0.897 | | |
| 30 | 30 | 195 | 29 | AT1G60970 | 0.92 | 0.709 | 0.908 | 0.746 | 0.78 | 0.747 | 0.742 | 0.745 |
| 31 | 31 | 196 | 30 | AT1G72580 | | | | | | | 0.935 | 0.917 |
| 32 | 32 | 197 | 31 | AT2G28490 | | 0.998 | 0.871 | 0.995 | | 0.882 | | |
| 33 | 33 | 198 | 32a | AT2G46960.1 | 0.89 | | | | | | 0.937 | 0.9 |
| 34 | 34 | 199 | 32b | AT2G46960.2 | 0.89 | | | | | | 0.937 | 0.9 |
| 35 | 35 | 200 | 166 | AT1G71691 | 0.938 | | 0.71 | | | | 0.723 | 0.713 |
| 36 | 36 | 201 | 330 | AT1G73220 | | 0.761 | 0.755 | 0.759 | | 0.768 | 0.899 | 0.85 |
| 37 | 37 | 202 | 3004 | AT5G01790 | 0.792 | | | | | | 0.899 | 0.85 |
| 38 | 38 | 203 | 333 | AT1G71120 | 0.866 | | | | | | 0.925 | 0.856 |
| 39 | 39 | 204 | 334 | AT5G38170 | 0.937 | | 0.869 | | 0.744 | | 0.81 | 0.793 |
| 40 | 40 | 205 | 335 | AT3G25160 | 0.88 | | 0.874 | | 0.747 | 0.761 | | |
| 41 | 41 | 206 | 336 | AT1G18100 | 0.917 | | 0.851 | | 0.751 | 0.711 | | |
| 42 | 42 | 207 | 337 | AT2G22620 | 0.906 | | | | | | 0.927 | 0.888 |
| 43 | 43 | 208 | 339 | AT3G26480 | | 0.785 | 0.717 | 0.784 | | | | |
| 44 | 44 | 209 | 340 | AT1G64660 | | 0.872 | 0.854 | 0.882 | | 0.808 | | |
| 45 | 45 | 210 | 341 | AT5G52330 | 0.811 | | | | | | 0.796 | 0.774 |
| 46 | 46 | 211 | 341 | AT5G52330 | 0.811 | | | | | | 0.796 | 0.774 |
| 47 | 47 | 212 | 342 | AT1G52670 | 0.802 | | | | | | | |
| 48 | 48 | 213 | 343 | AT5G64080 | | 0.923 | 0.876 | 0.923 | | 0.92 | | |
| 49 | 49 | 214 | 343 | AT5G64080 | | 0.923 | 0.876 | 0.923 | | 0.92 | | |
| 50 | 50 | 215 | 344 | AT2G43060 | 0.726 | | | | | | 0.857 | 0.794 |
| 51 | 51 | 216 | 345 | AT1G27330 | | 0.839 | 0.856 | 0.837 | | 0.814 | | |
| 52 | 52 | 217 | 2999 | AT2G41340 | 0.816 | | 0.745 | | 0.744 | | | |
| 53 | 54 | 219 | 2810 | AT2G13290 | | 0.878 | 0.76 | 0.876 | | 0.74 | | |
| 54 | 55 | 220 | 349 | AT4G33670 | | 0.861 | | 0.855 | | 0.734 | | |
| 55 | 56 | 221 | 350 | AT5G04500 | | 0.899 | 0.702 | 0.894 | | 0.756 | | |
| 56 | 64 | 229 | 358 | AT3G01570 | | 0.996 | 0.904 | 1 | | 0.891 | | |
| 57 | 65 | 230 | 359 | AT2G15010 | | 0.944 | 0.955 | 0.942 | 0.763 | 0.924 | | |
| 58 | 66 | 231 | 362 | AT2G25940 | 0.791 | 0.873 | 0.977 | 0.885 | 0.777 | 0.873 | | |
| 59 | 67 | 232 | 364 | AT1G04660 | 0.94 | | 0.882 | | 0.763 | 0.715 | 0.777 | 0.768 |
| 60 | 68 | 233 | 365 | AT1G05160 | 0.945 | | | | | | 0.857 | 0.814 |
| 61 | 69 | 234 | 2992 | AT1G05280 | 0.939 | | 0.805 | | | | 0.859 | 0.84 |
| 62 | 70 | 235 | 2993 | AT1G19900 | | 0.975 | 0.909 | 0.962 | | 0.898 | | |
| 63 | 71 | 236 | 368 | AT1G23200 | 0.852 | | | | | | 0.957 | 0.906 |
| 64 | 72 | 237 | 369 | AT1G26680 | 0.93 | | | | | | 0.738 | 0.717 |
| 65 | 73 | 238 | 370 | AT1G28590 | 0.937 | | | | | | 0.855 | 0.813 |
| 66 | 74 | 239 | 371 | AT1G48910 | 0.877 | 0.753 | 0.912 | 0.77 | 0.808 | 0.807 | | |
| 67 | 75 | 240 | 2995 | AT1G51000 | 0.906 | | | | | | 0.785 | 0.77 |
| 68 | 76 | 241 | 373 | AT1G62340 | 0.712 | | | | | | 0.978 | 0.903 |
| 69 | 77 | 242 | 374 | AT1G62610 | | 0.946 | 0.909 | 0.938 | | 0.891 | | |
| 70 | 78 | 243 | 374 | AT1G62610 | | 0.946 | 0.909 | 0.938 | | 0.891 | | |
| 71 | 79 | 244 | 374 | AT1G62610 | | 0.946 | 0.909 | 0.938 | | 0.891 | | |
| 72 | 80 | 245 | 375 | AT1G76290 | 0.735 | 0.91 | 0.967 | 0.923 | 0.803 | 0.904 | | |
| 73 | 81 | 246 | 376 | AT1G68470 | 0.917 | | 0.814 | | | | | |
| 74 | 82 | 247 | 377 | AT1G71250 | 0.922 | | | | | | 0.93 | 0.881 |
| 75 | 83 | 248 | 379 | AT3G58200 | 0.719 | 0.897 | 0.973 | 0.907 | 0.771 | 0.914 | | |

TABLE 1-continued

| Serial No | Nucl. SEQ ID NO: | Prot. SEQ ID NO: | BDL No | TAIR-gene name | R wri1 | R abi3 | R fus3 | R oleosin A | R ssi2 | R fad3 | R lec1 | R lec2 |
|---|---|---|---|---|---|---|---|---|---|---|---|---|
| 76 | 84 | 249 | 380 | AT1G78500 | 0.731 | 0.844 | 0.964 | 0.843 | 0.788 | 0.879 | | |
| 77 | 85 | 250 | 381 | AT2G14690 | | | | | | | 0.972 | 0.916 |
| 78 | 86 | 251 | 382 | AT3G63040 | | 0.949 | 0.979 | 0.962 | 0.783 | 0.907 | | |
| 79 | 87 | 252 | 383 | AT2G15325 | | | | | | | 0.978 | 0.929 |
| 80 | 88 | 253 | 384 | AT2G23510 | 0.804 | 0.767 | 0.943 | 0.777 | 0.789 | 0.85 | | |
| 81 | 89 | 254 | 385 | AT2G26070 | 0.927 | | | | | | 0.827 | 0.762 |
| 82 | 90 | 255 | 2997 | AT2G28650 | 0.811 | | 0.711 | | | | 0.953 | 0.939 |
| 83 | 91 | 256 | 2998 | AT2G41290 | 0.827 | | 0.869 | | 0.779 | 0.786 | | |
| 84 | 92 | 257 | 389 | AT2G42860 | 0.903 | 0.829 | | 0.727 | | | 0.825 | 0.813 |
| 85 | 93 | 258 | 390 | AT2G47750 | 0.906 | | 0.744 | | | | 0.784 | 0.754 |
| 86 | 94 | 259 | 391 | AT3G03230 | 0.828 | 0.844 | 0.954 | 0.854 | 0.783 | 0.833 | | |
| 87 | 95 | 260 | 392 | AT3G04200 | 0.912 | | 0.827 | | 0.733 | | | |
| 88 | 96 | 261 | 393 | AT3G21840 | 0.702 | | | | | | 0.968 | 0.928 |
| 89 | 97 | 262 | 3000 | AT3G22640 | | 0.995 | 0.855 | 0.991 | | 0.873 | | |
| 90 | 98 | 263 | 395 | AT3G49380 | 0.919 | | 0.724 | | | | 0.843 | 0.784 |
| 91 | 99 | 264 | 3001 | AT4G03050 | 0.93 | | 0.847 | | 0.749 | | | |
| 92 | 100 | 265 | 3001 | AT4G03050 | 0.93 | | 0.847 | | 0.749 | | | |
| 93 | 101 | 266 | 3003 | AT4G19380 | 0.783 | 0.792 | 0.913 | 0.803 | 0.826 | 0.839 | | |
| 94 | 102 | 267 | 398 | AT4G27460 | | 0.992 | 0.896 | 0.985 | | 0.897 | | |
| 95 | 103 | 268 | 399 | AT4G33280 | 0.885 | 0.715 | 0.912 | 0.732 | 0.811 | 0.8 | | |
| 96 | 104 | 269 | 400 | AT4G33600 | 0.917 | | | | | | 0.908 | 0.851 |
| 97 | 105 | 270 | 401 | AT5G07260 | 0.956 | | 0.82 | | 0.73 | | | |
| 98 | 106 | 271 | 3007 | AT5G08460 | 0.955 | | 0.768 | | 0.702 | | 0.757 | 0.747 |
| 99 | 107 | 272 | 403 | AT2G34700 | 0.932 | | 0.903 | | 0.783 | 0.741 | | |
| 100 | 108 | 273 | 404 | AT5G15740 | 0.911 | | 0.712 | | | | 0.883 | 0.818 |
| 101 | 109 | 274 | 405 | AT5G16230 | 0.812 | 0.82 | 0.961 | 0.834 | 0.773 | 0.858 | | |
| 102 | 110 | 275 | 406 | AT5G18290 | 0.905 | | 0.722 | | | | 0.821 | 0.803 |
| 103 | 111 | 276 | 2814 | AT5G25470 | 0.901 | | | | | | 0.748 | 0.711 |
| 104 | 112 | 277 | 408 | AT5G39130 | 0.951 | | 0.726 | | | | 0.769 | 0.75 |
| 105 | 113 | 278 | 409 | AT5G39160 | 0.94 | | 0.729 | | | | 0.829 | 0.789 |
| 106 | 114 | 279 | 409 | AT5G39160 | 0.94 | | 0.729 | | | | 0.829 | 0.789 |
| 107 | 115 | 280 | 410 | AT5G39190 | 0.951 | | 0.795 | | 0.706 | | 0.754 | 0.737 |
| 108 | 116 | 281 | 411 | AT5G44360 | 0.828 | 0.833 | 0.975 | 0.855 | 0.804 | 0.849 | | |
| 109 | 117 | 282 | 412 | AT5G47670 | 0.957 | | | | | | 0.797 | 0.759 |
| 110 | 118 | 283 | 3008 | AT5G49820 | 0.905 | | | | 0.715 | | | |
| 111 | 119 | 284 | 414 | AT5G56300 | 0.936 | | 0.823 | | 0.717 | | 0.712 | |
| 112 | 120 | 285 | 416 | AT5G59170 | | 0.995 | 0.852 | 0.991 | | 0.87 | | |
| 113 | 121 | 286 | 418 | AT1G28640 | | 0.967 | 0.949 | 0.975 | 0.752 | 0.92 | | |
| 114 | 122 | 287 | 419 | AT1G22990 | | 0.789 | 0.889 | 0.794 | | 0.738 | | |
| 115 | 123 | 288 | 2816a | AT1G64110.1 | | 0.883 | | 0.869 | | 0.701 | | |
| 116 | 124 | 289 | 2816b | AT1G64110.2 | | 0.883 | | 0.869 | | 0.701 | | |
| 117 | 125 | 290 | 421 | AT1G04380 | 0.971 | | 0.798 | | 0.717 | | 0.772 | 0.749 |
| 118 | 126 | 291 | 2817 | AT1G08810 | | 0.888 | 0.948 | 0.885 | 0.831 | 0.862 | | |
| 119 | 127 | 292 | 2817 | AT1G08810 | | 0.888 | 0.948 | 0.885 | 0.831 | 0.862 | | |
| 120 | 128 | 293 | 423 | AT1G28170 | | | | | | | 0.962 | 0.903 |
| 121 | 129 | 294 | 424 | AT1G28650 | 0.821 | 0.843 | 0.974 | 0.853 | 0.801 | 0.844 | | |
| 122 | 130 | 295 | 425 | AT3G10590 | | | | | | | 0.969 | 0.944 |
| 123 | 131 | 296 | 426 | AT3G58740 | 0.948 | | 0.842 | | 0.745 | | | |
| 124 | 132 | 297 | 427 | AT4G02360 | | 0.941 | 0.941 | 0.937 | 0.731 | 0.915 | | |
| 125 | 133 | 298 | 428 | AT4G36700 | | 0.965 | 0.967 | 0.976 | 0.768 | 0.899 | | |
| 126 | 134 | 299 | 429 | AT5G07200 | 0.957 | | 0.851 | | 0.753 | | 0.725 | 0.71 |
| 127 | 135 | 300 | 430 | AT5G22810 | 0.958 | | 0.702 | | | | 0.86 | 0.834 |
| 128 | 136 | 301 | 431 | AT5G43860 | | 0.866 | 0.916 | 0.868 | 0.776 | 0.817 | | |
| 129 | 137 | 302 | 432 | AT5G57390 | | 0.989 | 0.914 | 0.987 | 0.713 | 0.916 | | |
| 130 | 138 | 303 | 433 | AT5G62800 | | 0.961 | 0.967 | 0.962 | 0.769 | 0.913 | | |
| 131 | 139 | 304 | 435 | AT5G52500 | | | | | | | 0.956 | 0.876 |
| 132 | 140 | 305 | 436 | AT5G24600 | | 0.956 | 0.902 | 0.954 | | 0.863 | | |
| 133 | 141 | 306 | 2818 | AT2G23550 | 0.829 | | | | | | 0.928 | 0.839 |
| 134 | 142 | 307 | 2818 | AT2G23550 | 0.829 | | | | | | 0.928 | 0.839 |
| 135 | 146 | 311 | 441 | AT5G48100 | 0.737 | 0.923 | 0.95 | 0.944 | 0.761 | 0.864 | | |
| 136 | 147 | 312 | 442 | AT1G14760 | 0.708 | 0.874 | 0.93 | 0.876 | 0.831 | 0.877 | | |
| 137 | 148 | 313 | 443 | AT1G15150 | 0.871 | | | | | | 0.971 | 0.92 |
| 138 | 149 | 314 | 444 | AT1G20500 | 0.92 | | 0.783 | | | | 0.904 | 0.874 |
| 139 | 150 | 315 | 445 | AT1G56170 | 0.966 | | 0.751 | | | | 0.782 | 0.751 |
| 140 | 151 | 316 | 2996 | AT1G62070 | 0.956 | | | | | | 0.847 | 0.797 |
| 141 | 152 | 317 | 447 | AT1G67100 | | 0.967 | 0.969 | 0.973 | 0.761 | 0.914 | | |
| 142 | 153 | 318 | 448 | AT3G21090 | 0.902 | | 0.724 | | | | | |
| 143 | 154 | 319 | 449 | AT3G24250 | 0.826 | | | | | | 0.986 | 0.931 |
| 144 | 155 | 320 | 450 | AT3G50990 | 0.715 | | | | | | 0.982 | 0.914 |
| 145 | 156 | 321 | 451 | AT4G00220 | 0.905 | 0.741 | 0.923 | 0.773 | 0.782 | 0.779 | 0.7 | 0.703 |
| 146 | 157 | 322 | 452 | AT4G10150 | 0.706 | 0.875 | 0.95 | 0.883 | 0.821 | 0.886 | | |
| 147 | 158 | 323 | 3006 | AT5G07190 | | 0.998 | 0.903 | 0.997 | | 0.901 | | |
| 148 | 159 | 324 | 3006 | AT5G07190 | | 0.998 | 0.903 | 0.997 | | 0.901 | | |
| 149 | 160 | 325 | 455 | AT5G10220 | 0.722 | | | | | | 0.984 | 0.917 |
| 150 | 161 | 326 | 456 | AT5G20940 | | 0.969 | 0.901 | 0.961 | | 0.901 | | |

TABLE 1-continued

| Serial No | Nucl. SEQ ID NO: | Prot. SEQ ID NO: | BDL No | TAIR-gene name | R wri1 | R abi3 | R fus3 | R oleosin A | R ssi2 | R fad3 | R lec1 | R lec2 |
|---|---|---|---|---|---|---|---|---|---|---|---|---|
| 151 | 162 | 327 | 457 | AT5G51210 | 0.907 | 0.7 | 0.925 | 0.734 | 0.788 | 0.752 | 0.702 | 0.7 |
| 152 | 163 | 328 | 458 | AT5G55620 | 0.704 | 0.769 | 0.898 | 0.776 | 0.871 | 0.8 | | |
| 153 | 164 | 329 | 459 | AT5G60460 | | 0.987 | 0.931 | 0.988 | | 0.902 | | |
| 154 | 165 | 330 | 460 | AT5G65590 | 0.793 | 0.725 | 0.882 | 0.754 | 0.783 | 0.77 | | |
| 155 | 332 | 351 | 2991 | AT5G15000 | | 0.955 | 0.959 | 0.957 | 0.739 | 0.902 | | |
| 156 | 333 | 352 | 2992 | AT1G05280 | 0.939 | | 0.805 | | | | 0.859 | 0.84 |
| 157 | 334 | 353 | 2993 | AT1G19900 | | 0.975 | 0.909 | 0.962 | | 0.898 | | |
| 158 | 336 | 355 | 2995 | AT1G51000 | 0.906 | | | | | | 0.785 | 0.77 |
| 159 | 337 | 356 | 2996 | AT1G62070 | 0.956 | | | | | | 0.847 | 0.797 |
| 160 | 338 | 357 | 2997 | AT2G28650 | 0.811 | | 0.711 | | | | 0.953 | 0.939 |
| 161 | 339 | 358 | 2998 | AT2G41290 | 0.827 | | 0.869 | | 0.779 | 0.786 | | |
| 162 | 340 | 359 | 2999 | AT2G41340 | 0.816 | | 0.745 | | 0.744 | | | |
| 163 | 341 | 360 | 3000 | AT3G22640 | | 0.995 | 0.855 | 0.991 | | 0.873 | | |
| 164 | 342 | 361 | 3001 | AT4G03050 | 0.93 | | 0.847 | | 0.749 | | | |
| 165 | 344 | 363 | 3003 | AT4G19380 | 0.783 | 0.792 | 0.913 | 0.803 | 0.826 | 0.839 | | |
| 166 | 345 | 364 | 3004 | AT5G01790 | 0.792 | | | | | | 0.899 | 0.85 |
| 167 | 347 | 366 | 3006 | AT5G07190 | | 0.998 | 0.903 | 0.997 | | 0.901 | | |
| 168 | 348 | 367 | 3007 | AT5G08460 | 0.955 | | 0.768 | | 0.702 | | 0.757 | 0.747 |
| 169 | 349 | 368 | 3008 | AT5G49820 | 0.905 | | | | 0.715 | | | |

Table 1

Additional genes which are predicted to affect seed oil synthesis and which were identified using bioinformatics tools are provided in Table 2, below.

TABLE 2

| Serial No | Polynucleotide SEQ ID NO: | Polypeptide SEQ ID NO: | BDL No. | TAIR- gene name |
|---|---|---|---|---|
| 1 | 53 | 218 | 3005 | AT5G03450.1 |
| 2 | 57 | 222 | 351 | AT1G27120.1 |
| 3 | 58 | 223 | 352 | AT5G01820.1 |
| 4 | 59 | 224 | 353 | AT2G32780.1 |
| 5 | 60 | 225 | 354 | AT3G16490.1 |
| 6 | 61 | 226 | 355 | AT5G23050.1 |
| 7 | 62 | 227 | 3002 | AT4G16050.1 |
| 8 | 63 | 228 | 2994 | AT1G44760.1 |
| 9 | 143 | 308 | 438 | AT1G72040 |
| 10 | 144 | 309 | 439 | AT1G53070 |
| 11 | 145 | 310 | 440 | AT1G50510 |
| 12 | 331 | 350 | 2990 | AT5G14995 |
| 13 | 335 | 354 | 2994 | AT1G44760 |
| 14 | 343 | 362 | 3002 | AT4G16050 |
| 15 | 346 | 365 | 3005 | AT5G03450 |

Table 2.

Example 2

Production of *Arabidopsis Transcriptom* and High Throughput Correlation Analysis Using 44K *Arabidopsis* Full Genome Oligonucleotide Micro-Array In order to produce a high throughput correlation analysis, the present inventors utilized an *Arabidopsis thaliana* oligonucleotide micro-array, produced by Agilent Technologies [Hypertext Transfer Protocol://World Wide Web (dot) chem. (dot) agilent (dot) com/Scripts/PDS (dot) asp?l-Page=50879]. The array oligonucleotide represents about 40,000 *A. thaliana* genes and transcripts designed based on data from the TIGR ATH1 v.5 database and *Arabidopsis* MPSS (University of Delaware) databases. In order to define correlations between the levels of RNA expression and yield components or vigor related parameters, various plant characteristics of 15 different *Arabidopsis* ecotypes were analyzed. Among them, nine ecotypes encompassing the observed variance were selected for RNA expression analysis. The correlation between the RNA levels and the characterized parameters was analyzed using Pearson correlation test [Hypertext Transfer Protocol://World Wide Web (dot) davidmlane (dot) com/hyperstat/A34739 (dot) html].
Experimental Procedures RNA extraction—Five tissues at different developmental stages [root, leaf, flower at anthesis, seed at 5 days after flowering (DAF) and seed at 12 DAF], representing different plant characteristics, were sampled and RNA was extracted using TRIzol Reagent from Invitrogen [Hypertext Transfer Protocol://World Wide Web (dot) invitrogen (dot) com/content (dot)cfm?pageid=469]. For convenience, each micro-array expression information tissue type has received a Set ID as summarized in Table 3 below.

TABLE 3

*Arabidopsis* transcriptom experimental sets

| Expression Set | Set ID |
|---|---|
| Root | A |
| Leaf | B |
| Flower | C |
| Seed 5 DAF | D |
| Seed 12 DAF | E |

Table 3

Approximately 30-50 mg of tissue was taken from samples. The weighed tissues were ground using pestle and mortar in liquid nitrogen and resuspended in 500 μl of TRIzol Reagent. To the homogenized lysate, 100 μl of chloroform was added followed by precipitation using isopropanol and two washes with 75% ethanol. The RNA was eluted in 30 μl of RNase-free water. RNA samples were cleaned up using Qiagen's RNeasy minikit clean-up protocol as per the manufacturer's protocol.

Yield component and vigor related parameters assessment—8 *Arabidopsis* ecotypes in 5 repetitive blocks (named A, B, C, D and E), each containing 20 plants per plot were grown at control conditions greenhouse 22° C., 20:20:20 (weight ratios) N:P:K [nitrogen (N), phosphorus (P) and potassium (K)] fertilizer was added. During this time data was collected documented and analyzed. Additional data was collected through the seedling stage of plants grown at tissue culture in vertical grown transparent agar plates. Data parameters collected are summarized in Table 4, below.

TABLE 4

Arabidopsis correlated parameters (vectors)

| Correlated parameter with | Correlation Id |
|---|---|
| Root length day 13 (cm) | 1 |
| Root length day 7 (cm) | 2 |
| Relative root growth (cm/day) day 13 | 3 |
| Fresh weight per plant (gr) at bolting stage | 4 |
| Dry matter per plant (gr) | 5 |
| Vegetative growth rate (cm$^2$/day) till 8 true leaves | 6 |
| Blade circularity | 7 |
| Lamina width (cm) | 8 |
| Lamina length (cm) | 9 |
| Total leaf area per plant (cm) | 10 |
| 1000 Seed weight (gr) | 11 |
| Oil % per seed | 12 |
| Seeds per silique | 13 |
| Silique length (cm) | 14 |
| Seed yield per plant (gr) | 15 |
| Oil yield per plant (mg) | 16 |
| Harvest Index | 17 |
| Leaf width/length | 18 |

Table 4.

Most of chosen parameters were analyzed by digital imaging.

Digital imaging—A laboratory image acquisition system, which consists of a digital reflex camera (Canon EOS 300D) attached with a 55 mm focal length lens (Canon EF-S series), mounted on a reproduction device (Kaiser RS), which included 4 light units (4×150 Watts light bulb) and located in a darkroom, was used for capturing images of plantlets sawn in square agar plates.

The image capturing process was repeated every 2 days starting at day 7 till day 14. The same camera attached with a 24 mm focal length lens (Canon EF series), placed in a custom made iron mount, was used for capturing images of larger plants sawn in white tubs in an environmental controlled greenhouse (as seen on FIG. 2b). The white tubs were square shape with measurements of 36×26.2 cm and 7.5 cm deep. During the capture process, the tubs were placed beneath the iron mount, while avoiding direct sun light and casting of shadows. This process was repeated every 3-4 days for up to 30 days.

An image analysis system was used, which consists of a personal desktop computer (Intel P4 3.0 GHz processor) and a public domain program—ImageJ 1.37 (Java based image processing program which was developed at the U.S National Institutes of Health and freely available on the internet at Hypertext Transfer Protocol://rsbweb (dot) nih (dot) gov/). Images were captured in resolution of 6 Mega Pixels (3072×2048 pixels) and stored in a low compression JPEG (Joint Photographic Experts Group standard) format. Next, analyzed data was saved to text files and processed using the JMP statistical analysis software (SAS institute).

Leaf analysis—Using the digital analysis leaves data was calculated, including leaf number, area, perimeter, length and width. On day 30, 3-4 representative plants were chosen from each plot of blocks A, B and C. The plants were dissected, each leaf was separated and was introduced between two glass trays, a photo of each plant was taken and the various parameters (such as leaf total area, laminar length etc.) were calculated from the images (FIGS. 1a-d). The blade circularity was calculated as laminar width divided by laminar length.

Figure 1A:
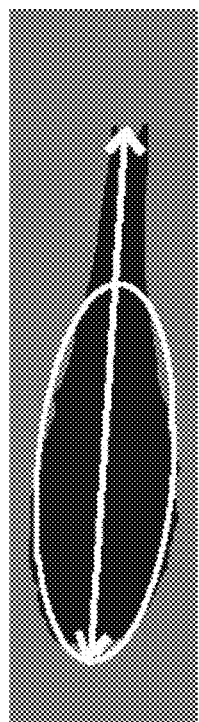
FIGS. 1a-d are digital images of leaves depicting leaf length (FIG. 1a, the leaf length is represented by the arrow), laminar length (FIG. 1b, the laminar length is represented by the arrow), laminar area (FIG. 1c, the laminar area is represented by the white ellipse) and laminar width (FIG. 1d, the laminar width is represented by the arrow). Blade circularity was calculated as laminar width divided by laminar length.
Figure 1B:
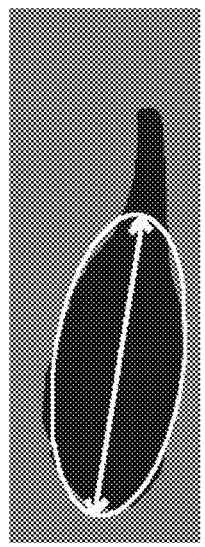
Figure 1C:
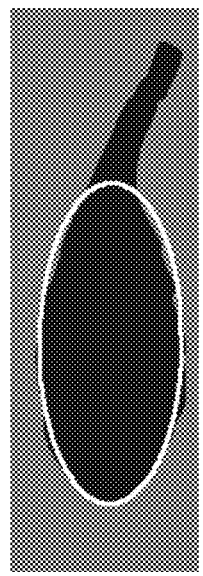
Figure 1D:
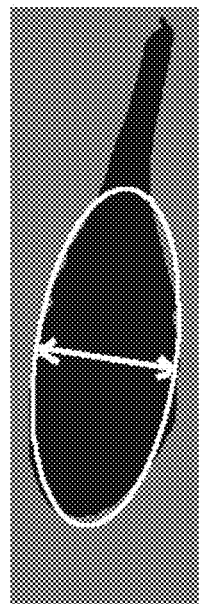
Figures 2A, 2B:
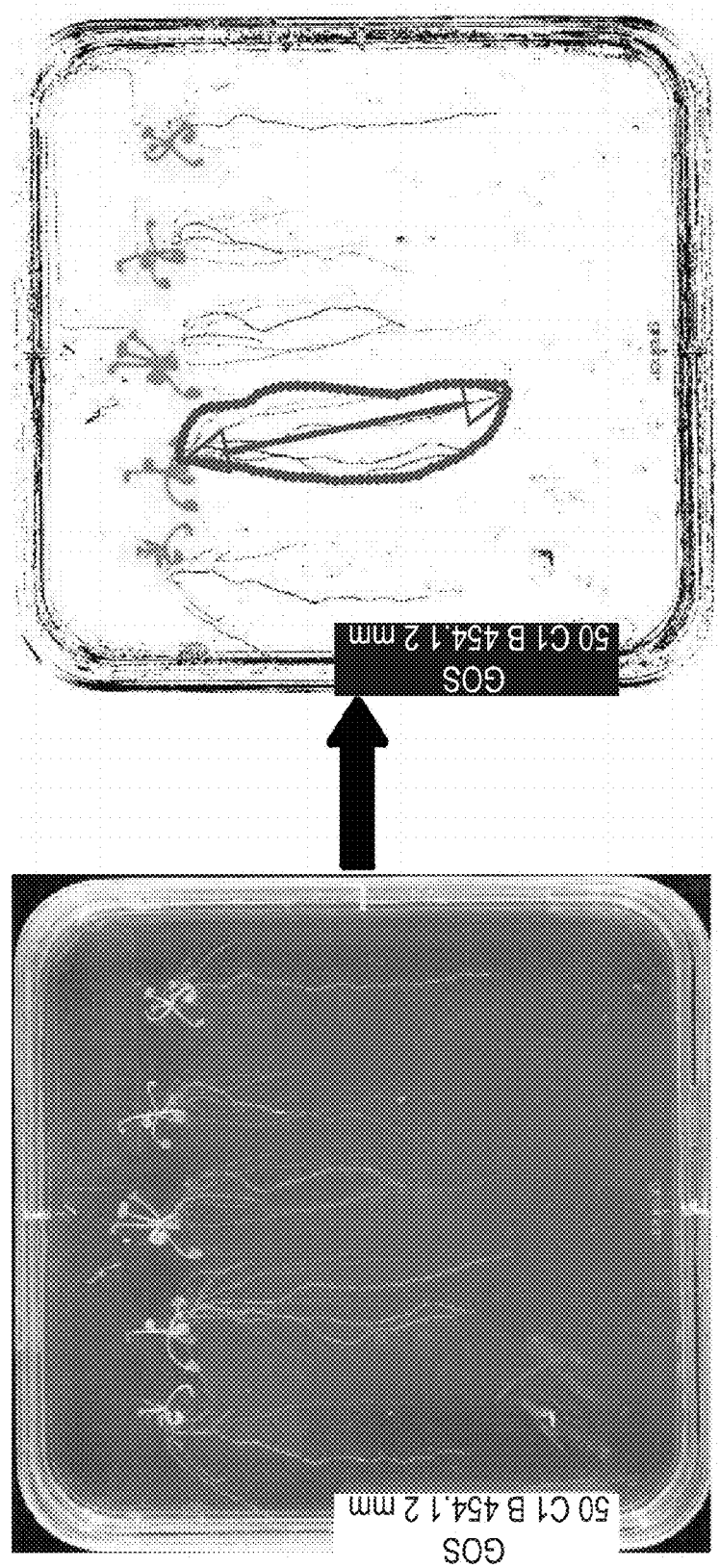
FIGS. 2a-b are images depicting root development of plants grown in transparent agar plates. The different ecotypes were grown in transparent agar plates for 17 days and the plates were photographed every 2 days starting at day 7. An exemplary image is shown in FIG. 2a (taken following 12 days on agar plates). The length of the root measured is represented by the red arrow (FIG. 2b).

Root analysis—During 17 days, the different ecotypes were grown in transparent agar plates. The plates were photographed every 2 days starting at day 7 in the photography room and the roots development was documented (FIGS. 2a-b).

The growth rate was calculated according to the following formula I.

Relative growth area rate=($\Delta$Area/$\Delta t$)*(1/Area t0)     Formula I $\Delta t$ is the current analyzed image day subtracted from the initial day (t40). 20 Thus, the relative growth area rate is in units of 1/day and length growth rate is in units of 1/day.

Vegetative growth rate analysis—The growth rate was calculated by dividing the area added ($\Delta$ Area) by the number of days for each interval ($\Delta t$). The analysis was ended with the appearance of overlapping plants.

The growth rate was calculated according to formula II.

Growth rate=$\Delta$Area/$\Delta t$.     Formula II

For comparison between ecotypes the calculated rate was normalized using plant developmental stage as represented by the number of true leaves. In cases where plants with 8 leaves had been sampled twice (for example at day 10 and day 13), only the largest sample was chosen and added to the Anova comparison.

Seeds in siliques analysis—On day 70, 15-17 siliques were collected from each plot in blocks D and E. The chosen siliques were light brown color but still intact. The siliques were opened in the photography room and the seeds were scatter on a glass tray, a high resolution digital picture was taken for each plot. Using the images the number of seeds per silique was determined.

Seeds average weight—At the end of the experiment all seeds from plots A-C were collected. An average weight of 0.02 grams was measured from each sample, the seeds were scattered on a glass tray and a picture was taken. Using the digital analysis, the number of seeds in each sample was calculated.

Oil percentage in seeds—At the end of the experiment all seeds from plots A-C were collected. Columbia seeds from 3 plots were mixed grounded and then mounted onto the extraction chamber. 210 ml of n-Hexane (Cat No. 080951 Biolab Ltd.) were used as the solvent. The extraction was performed for 30 hours at medium heat 50° C. Once the extraction has ended the n-Hexane was evaporated using the evaporator at 35° C. and vacuum conditions. The process was repeated twice. The information gained from the Soxhlet extractor (Soxhlet, F. Die gewichtsanalytische Bestimmung des Milchfettes, Polytechnisches J. (Dingier's) 1879, 232, 461) was used to create a calibration curve for the Low Resonance NMR. The content of oil of all seed samples was determined using the Low Resonance NMR (MARAN Ultra-Oxford Instrument) and its MultiQuant sowftware package.

Silique length analysis—On day 50 from sowing, 30 siliques from different plants in each plot were sampled in block A. The chosen siliques were green-yellow in color and were collected from the bottom parts of a grown plant's stem. A digital photograph was taken to determine silique's length.

Dry weight and seed yield—On day 80 from sowing, the plants from blocks A-C were harvested and left to dry at 30°

C. in a drying chamber. The biomass and seed weight of each plot was separated, measured and divided by the number of plants. Dry weight=total weight of the vegetetative portion above ground (excluding roots) after drying at 30° C. in a drying chamber; Seed yield per plant=total seed weight per plant (gr).

Oil yield—The oil yield was calculated using Formula III.

Seed Oil yield=Seed yield per plant (gr)*Oil % in seed     Formula III

Harvest index—The harvest index was calculated using Formula IV.

Harvest Index=Average seed yield per plant/Average dry weight     Formula IV

Experimental Results

Nine different *Arabidopsis* ecotypes were grown and characterized for 18 parameters (named as vectors). The characterized values are summarized in Tables 5 and 6 below.

TABLE 5

*Arabidopsis* ecotypes, measured parameters

| Ecotype | Seed yield per plant (gr) | Oil yield per plant (mg) | Oil % per seed | 1000 Seed weight (gr) | Dry matter per plant (gr) | Harvest Index | Total leaf area per plant (cm) | Seeds per silique | Silique length (cm) |
|---|---|---|---|---|---|---|---|---|---|
| An-1 | 0.34 | 118.63 | 34.42 | 0.0203 | 0.64 | 0.53 | 46.86 | 45.44 | 1.06 |
| Col-0 | 0.44 | 138.73 | 31.19 | 0.0230 | 1.27 | 0.35 | 109.89 | 53.47 | 1.26 |
| Ct-1 | 0.59 | 224.06 | 38.05 | 0.0252 | 1.05 | 0.56 | 58.36 | 58.47 | 1.31 |
| Cvi (N8580) | 0.42 | 116.26 | 27.76 | 0.0344 | 1.28 | 0.33 | 56.80 | 35.27 | 1.47 |
| Gr-6 | 0.61 | 218.27 | 35.49 | 0.0202 | 1.69 | 0.37 | 114.66 | 48.56 | 1.24 |
| Kondara | 0.43 | 142.11 | 32.91 | 0.0263 | 1.34 | 0.32 | 110.82 | 37.00 | 1.09 |
| Ler-1 | 0.36 | 114.15 | 31.56 | 0.0205 | 0.81 | 0.45 | 88.49 | 39.38 | 1.18 |
| Mt-0 | 0.62 | 190.06 | 30.79 | 0.0226 | 1.21 | 0.51 | 121.79 | 40.53 | 1.18 |
| Shakdara | 0.55 | 187.62 | 34.02 | 0.0235 | 1.35 | 0.41 | 93.04 | 25.53 | 1.00 |

Table 5

TABLE 6

*Arabidopsis* ecotypes, additional measured parameters

| Ecotype | Vegetative growth rate (cm²/day) till 8 true leaves | Relative root growth (cm/day) day 13 | Root length day 7 (cm) | Root length day 13 (cm) | Fresh weight per plant (gr) at bolting stage | Lamina length (cm) | Lamina width (cm) | Leaf width/ length | Blade circularity |
|---|---|---|---|---|---|---|---|---|---|
| An-1 | 0.313 | 0.631 | 0.937 | 4.419 | 1.510 | 2.767 | 1.385 | 0.353 | 0.509 |
| Col-0 | 0.378 | 0.664 | 1.759 | 8.530 | 3.607 | 3.544 | 1.697 | 0.288 | 0.481 |
| Ct-1 | 0.484 | 1.176 | 0.701 | 5.621 | 1.935 | 3.274 | 1.460 | 0.316 | 0.450 |
| Cvi (N8580) | 0.474 | 1.089 | 0.728 | 4.834 | 2.082 | 3.785 | 1.374 | 0.258 | 0.370 |
| Gr-6 | 0.425 | 0.907 | 0.991 | 5.957 | 3.556 | 3.690 | 1.828 | 0.356 | 0.501 |
| Kondara | 0.645 | 0.774 | 1.163 | 6.372 | 4.338 | 4.597 | 1.650 | 0.273 | 0.376 |
| Ler-1 | 0.430 | 0.606 | 1.284 | 5.649 | 3.467 | 3.877 | 1.510 | 0.305 | 0.394 |
| Mt-0 | 0.384 | 0.701 | 1.414 | 7.060 | 3.479 | 3.717 | 1.817 | 0.335 | 0.491 |
| Shakdara | 0.471 | 0.782 | 1.251 | 7.041 | 3.710 | 4.149 | 1.668 | 0.307 | 0.409 |

Table 6

The selected genes, their R (calculated using Pearson correlation), the characterized parameters used as x axis for correlation and the tissue transcriptom correlated with are summarized in Table 7, below.

TABLE 7

*Arabidopsis* selected genes and their correlation with yield components among different transcriptom sets

| | Nucleotide SEQ ID NO: | Polypeptide SEQ ID NO: | Gene Name | Cluster Name | Exp. Set | Correl. Vector | R |
|---|---|---|---|---|---|---|---|
| 1 | 3 | 168 | BDL2 | arabidopsis\|6\|AT1G34580 | B | 8 | 0.77 |
| 2 | 3 | 168 | BDL2 | arabidopsis\|6\|AT1G34580 | D | 15 | 0.75 |
| 3 | 3 | 168 | BDL2 | arabidopsis\|6\|AT1G34580 | D | 16 | 0.71 |
| 4 | 6 | 171 | BDL6 | arabidopsis\|6\|AT4G10490 | E | 12 | −0.7 |

TABLE 7-continued

*Arabidopsis* selected genes and their correlation with yield components among different transcriptom sets

| | Nucleotide SEQ ID NO: | Polypeptide SEQ ID NO: | Gene Name | Cluster Name | Exp. Set | Correl. Vector | R |
|---|---|---|---|---|---|---|---|
| 5 | 7 | 172 | BDL7 | arabidopsis\|6\|AT5G51490 | A | 15 | 0.76 |
| 6 | 7 | 172 | BDL7 | arabidopsis\|6\|AT5G51490 | A | 16 | 0.74 |
| 7 | 7 | 172 | BDL7 | arabidopsis\|6\|AT5G51490 | B | 4 | −0.78 |
| 8 | 7 | 172 | BDL7 | arabidopsis\|6\|AT5G51490 | B | 9 | −0.77 |
| 9 | 7 | 172 | BDL7 | arabidopsis\|6\|AT5G51490 | B | 10 | −0.73 |
| 10 | 7 | 172 | BDL7 | arabidopsis\|6\|AT5G51490 | B | 17 | 0.88 |
| 11 | 8 | 173 | BDL8 | arabidopsis\|6\|AT3G03240 | D | 15 | 0.87 |
| 12 | 8 | 173 | BDL8 | arabidopsis\|6\|AT3G03240 | D | 16 | 0.89 |
| 13 | 9 | 174 | BDL9 | arabidopsis\|6\|AT5G24130 | D | 15 | 0.75 |
| 14 | 9 | 174 | BDL9 | arabidopsis\|6\|AT5G24130 | D | 16 | 0.75 |
| 15 | 9 | 174 | BDL9 | arabidopsis\|6\|AT5G24130 | E | 13 | 0.75 |
| 16 | 10 | 175 | BDL10 | arabidopsis\|6\|AT5G09640 | E | 11 | 0.72 |
| 17 | 13 | 178 | BDL14 | arabidopsis\|6\|AT1G53690 | B | 11 | 0.87 |
| 18 | 13 | 178 | BDL14 | arabidopsis\|6\|AT1G53690 | B | 12 | −0.71 |
| 19 | 13 | 178 | BDL14 | arabidopsis\|6\|AT1G53690 | B | 14 | 0.71 |
| 20 | 13 | 178 | BDL14 | arabidopsis\|6\|AT1G53690 | E | 11 | 0.72 |
| 21 | 14 | 179 | BDL15 | arabidopsis\|6\|AT1G68510 | E | 15 | 0.72 |
| 22 | 16 | 181 | BDL17 | arabidopsis\|6\|AT5G36770 | D | 15 | 0.75 |
| 23 | 18 | 183 | BDL19 | arabidopsis\|6\|AT2G02080 | C | 16 | 0.7 |
| 24 | 18 | 183 | BDL19 | arabidopsis\|6\|AT2G02080 | D | 17 | 0.72 |
| 25 | 19 | 184 | BDL20a | arabidopsis\|6\|AT1G47540 | A | 11 | 0.85 |
| 26 | 20 | 185 | BDL20b | arabidopsis\|6\|AT1G47540 | A | 11 | 0.85 |
| 27 | 21 | 186 | BDL21 | arabidopsis\|6\|AT3G62730 | D | 17 | 0.8 |
| 28 | 21 | 186 | BDL21 | arabidopsis\|6\|AT3G62730 | E | 11 | 0.79 |
| 29 | 21 | 186 | BDL21 | arabidopsis\|6\|AT3G62730 | E | 14 | 0.79 |
| 30 | 22 | 187 | BDL22 | arabidopsis\|6\|AT2G27380 | A | 11 | 0.81 |
| 31 | 22 | 187 | BDL22 | arabidopsis\|6\|AT2G27380 | A | 12 | −0.75 |
| 32 | 23 | 188 | BDL23 | arabidopsis\|6\|AT3G27785 | E | 11 | 0.7 |
| 33 | 23 | 188 | BDL23 | arabidopsis\|6\|AT3G27785 | E | 12 | −0.86 |
| 34 | 23 | 188 | BDL23 | arabidopsis\|6\|AT3G27785 | E | 14 | 0.71 |
| 35 | 25 | 190 | BDL25 | arabidopsis\|6\|AT3G20910 | A | 5 | 0.77 |
| 36 | 25 | 190 | BDL25 | arabidopsis\|6\|AT3G20910 | A | 8 | 0.7 |
| 37 | 25 | 190 | BDL25 | arabidopsis\|6\|AT3G20910 | B | 12 | 0.72 |
| 38 | 25 | 190 | BDL25 | arabidopsis\|6\|AT3G20910 | B | 16 | 0.75 |
| 39 | 25 | 190 | BDL25 | arabidopsis\|6\|AT3G20910 | C | 15 | 0.77 |
| 40 | 25 | 190 | BDL25 | arabidopsis\|6\|AT3G20910 | C | 16 | 0.81 |
| 41 | 25 | 190 | BDL25 | arabidopsis\|6\|AT3G20910 | D | 12 | 0.77 |
| 42 | 25 | 190 | BDL25 | arabidopsis\|6\|AT3G20910 | D | 15 | 0.73 |
| 43 | 25 | 190 | BDL25 | arabidopsis\|6\|AT3G20910 | D | 16 | 0.8 |
| 44 | 26 | 191 | BDL26a | arabidopsis\|6\|AT1G11170 | C | 15 | −0.77 |
| 45 | 27 | 192 | BDL26b | arabidopsis\|6\|AT1G11170 | C | 15 | −0.77 |
| 46 | 28 | 193 | BDL27 | arabidopsis\|6\|AT1G68380 | A | 13 | −0.71 |
| 47 | 28 | 193 | BDL27 | arabidopsis\|6\|AT1G68380 | C | 13 | −0.75 |
| 48 | 28 | 193 | BDL27 | arabidopsis\|6\|AT1G68380 | E | 11 | 0.71 |
| 49 | 28 | 193 | BDL27 | arabidopsis\|6\|AT1G68380 | E | 14 | 0.74 |
| 50 | 29 | 194 | BDL28 | arabidopsis\|6\|AT1G09380 | C | 11 | 0.87 |
| 51 | 29 | 194 | BDL28 | arabidopsis\|6\|AT1G09380 | C | 12 | −0.79 |
| 52 | 29 | 194 | BDL28 | arabidopsis\|6\|AT1G09380 | C | 14 | 0.73 |
| 53 | 29 | 194 | BDL28 | arabidopsis\|6\|AT1G09380 | E | 15 | 0.83 |
| 54 | 29 | 194 | BDL28 | arabidopsis\|6\|AT1G09380 | E | 16 | 0.8 |
| 55 | 30 | 195 | BDL29 | arabidopsis\|6\|AT1G60970 | B | 9 | −0.74 |
| 56 | 30 | 195 | BDL29 | arabidopsis\|6\|AT1G60970 | C | 11 | 0.76 |
| 57 | 30 | 195 | BDL29 | arabidopsis\|6\|AT1G60970 | D | 12 | 0.87 |
| 58 | 30 | 195 | BDL29 | arabidopsis\|6\|AT1G60970 | D | 15 | 0.88 |
| 59 | 30 | 195 | BDL29 | arabidopsis\|6\|AT1G60970 | D | 16 | 0.93 |
| 60 | 30 | 195 | BDL29 | arabidopsis\|6\|AT1G60970 | E | 11 | 0.8 |
| 61 | 32 | 197 | BDL31 | arabidopsis\|6\|AT2G28490 | A | 11 | 0.85 |
| 62 | 32 | 197 | BDL31 | arabidopsis\|6\|AT2G28490 | A | 12 | −0.74 |
| 63 | 32 | 197 | BDL31 | arabidopsis\|6\|AT2G28490 | A | 14 | 0.71 |
| 64 | 35 | 200 | BDL166 | arabidopsis\|6\|AT1G71691 | D | 12 | 0.78 |
| 65 | 35 | 200 | BDL166 | arabidopsis\|6\|AT1G71691 | D | 17 | 0.72 |
| 66 | 36 | 201 | BDL_unnamed_330 | arabidopsis\|6\|AT1G73220 | B | 6 | 0.8 |
| 67 | 36 | 201 | BDL_unnamed_330 | arabidopsis\|6\|AT1G73220 | C | 12 | −0.78 |
| 68 | 36 | 201 | BDL_unnamed_330 | arabidopsis\|6\|AT1G73220 | C | 17 | −0.77 |
| 69 | 36 | 201 | BDL_unnamed_330 | arabidopsis\|6\|AT1G73220 | D | 17 | −0.76 |
| 70 | 37 | 202 | BDL_unnamed_331 | arabidopsis\|6\|AT5G01790 | B | 5 | 0.85 |
| 71 | 37 | 202 | BDL_unnamed_331 | arabidopsis\|6\|AT5G01790 | E | 14 | 0.72 |
| 72 | 38 | 203 | BDL_unnamed_333 | arabidopsis\|6\|AT1G71120 | B | 12 | −0.77 |
| 73 | 38 | 203 | BDL_unnamed_333 | arabidopsis\|6\|AT1G71120 | B | 14 | 0.77 |
| 74 | 38 | 203 | BDL_unnamed_333 | arabidopsis\|6\|AT1G71120 | E | 11 | 0.82 |
| 75 | 38 | 203 | BDL_unnamed_333 | arabidopsis\|6\|AT1G71120 | E | 14 | 0.88 |
| 76 | 39 | 204 | BDL_unnamed_334 | arabidopsis\|6\|AT5G38170 | D | 15 | 0.82 |
| 77 | 39 | 204 | BDL_unnamed_334 | arabidopsis\|6\|AT5G38170 | D | 16 | 0.81 |

TABLE 7-continued

*Arabidopsis* selected genes and their correlation with yield components among different transcriptom sets

| | Nucleotide SEQ ID NO: | Polypeptide SEQ ID NO: | Gene Name | Cluster Name | Exp. Set | Correl. Vector | R |
|---|---|---|---|---|---|---|---|
| 78 | 39 | 204 | BDL_unnamed_334 | arabidopsis\|6\|AT5G38170 | E | 11 | 0.87 |
| 79 | 39 | 204 | BDL_unnamed_334 | arabidopsis\|6\|AT5G38170 | E | 12 | −0.75 |
| 80 | 39 | 204 | BDL_unnamed_334 | arabidopsis\|6\|AT5G38170 | E | 14 | 0.79 |
| 81 | 40 | 205 | BDL_unnamed_335 | arabidopsis\|6\|AT3G25160 | A | 1 | −0.89 |
| 82 | 40 | 205 | BDL_unnamed_335 | arabidopsis\|6\|AT3G25160 | A | 2 | −0.76 |
| 83 | 40 | 205 | BDL_unnamed_335 | arabidopsis\|6\|AT3G25160 | E | 11 | 0.71 |
| 84 | 42 | 207 | BDL_unnamed_337 | arabidopsis\|6\|AT2G22620 | A | 13 | −0.76 |
| 85 | 42 | 207 | BDL_unnamed_337 | arabidopsis\|6\|AT2G22620 | E | 15 | 0.86 |
| 86 | 42 | 207 | BDL_unnamed_337 | arabidopsis\|6\|AT2G22620 | E | 16 | 0.79 |
| 87 | 43 | 208 | BDL_unnamed_339 | arabidopsis\|6\|AT3G26480 | A | 11 | 0.84 |
| 88 | 43 | 208 | BDL_unnamed_339 | arabidopsis\|6\|AT3G26480 | A | 14 | 0.73 |
| 89 | 43 | 208 | BDL_unnamed_339 | arabidopsis\|6\|AT3G26480 | C | 11 | 0.76 |
| 90 | 43 | 208 | BDL_unnamed_339 | arabidopsis\|6\|AT3G26480 | C | 14 | 0.88 |
| 91 | 44 | 209 | BDL_unnamed_340 | arabidopsis\|6\|AT1G64660 | A | 1 | 0.83 |
| 92 | 44 | 209 | BDL_unnamed_340 | arabidopsis\|6\|AT1G64660 | A | 2 | 0.7 |
| 93 | 46 | 211 | BDL_unnamed_341 | arabidopsis\|6\|AT5G52330 | E | 17 | 0.85 |
| 94 | 49 | 214 | BDL_unnamed_343 | arabidopsis\|6\|AT5G64080 | C | 12 | 0.74 |
| 95 | 49 | 214 | BDL_unnamed_343 | arabidopsis\|6\|AT5G64080 | C | 16 | 0.77 |
| 96 | 50 | 215 | BDL_unnamed_344 | arabidopsis\|6\|AT2G43060 | B | 11 | 0.89 |
| 97 | 50 | 215 | BDL_unnamed_344 | arabidopsis\|6\|AT2G43060 | B | 12 | −0.73 |
| 98 | 50 | 215 | BDL_unnamed_344 | arabidopsis\|6\|AT2G43060 | B | 18 | −0.81 |
| 99 | 50 | 215 | BDL_unnamed_344 | arabidopsis\|6\|AT2G43060 | E | 15 | 0.8 |
| 100 | 52 | 217 | BDL_unnamed_346 | arabidopsis\|6\|AT2G41340 | A | 13 | −0.72 |
| 101 | 52 | 217 | BDL_unnamed_346 | arabidopsis\|6\|AT2G41340 | B | 5 | 0.72 |
| 102 | 52 | 217 | BDL_unnamed_346 | arabidopsis\|6\|AT2G41340 | B | 8 | 0.81 |
| 103 | 53 | 218 | BDL_unnamed_347 | arabidopsis\|6\|AT5G03450 | A | 3 | 0.76 |
| 104 | 53 | 218 | BDL_unnamed_347 | arabidopsis\|6\|AT5G03450 | A | 5 | 0.74 |
| 105 | 53 | 218 | BDL_unnamed_347 | arabidopsis\|6\|AT5G03450 | A | 15 | 0.74 |
| 106 | 53 | 218 | BDL_unnamed_347 | arabidopsis\|6\|AT5G03450 | D | 15 | 0.78 |
| 107 | 53 | 218 | BDL_unnamed_347 | arabidopsis\|6\|AT5G03450 | D | 16 | 0.82 |
| 108 | 55 | 220 | BDL_unnamed_349 | arabidopsis\|6\|AT4G33670 | A | 5 | 0.74 |
| 109 | 55 | 220 | BDL_unnamed_349 | arabidopsis\|6\|AT4G33670 | A | 15 | 0.78 |
| 110 | 55 | 220 | BDL_unnamed_349 | arabidopsis\|6\|AT4G33670 | A | 16 | 0.73 |
| 111 | 55 | 220 | BDL_unnamed_349 | arabidopsis\|6\|AT4G33670 | B | 5 | 0.86 |
| 112 | 56 | 221 | BDL_unnamed_350 | arabidopsis\|6\|AT5G04500 | A | 13 | −0.72 |
| 113 | 56 | 221 | BDL_unnamed_350 | arabidopsis\|6\|AT5G04500 | C | 15 | 0.85 |
| 114 | 56 | 221 | BDL_unnamed_350 | arabidopsis\|6\|AT5G04500 | C | 16 | 0.83 |
| 115 | 56 | 221 | BDL_unnamed_350 | arabidopsis\|6\|AT5G04500 | E | 11 | −0.72 |
| 116 | 56 | 221 | BDL_unnamed_350 | arabidopsis\|6\|AT5G04500 | E | 12 | 0.73 |
| 117 | 56 | 221 | BDL_unnamed_350 | arabidopsis\|6\|AT5G04500 | E | 17 | 0.74 |
| 118 | 57 | 222 | BDL_unnamed_351 | arabidopsis\|6\|AT1G27120 | B | 7 | 0.78 |
| 119 | 57 | 222 | BDL_unnamed_351 | arabidopsis\|6\|AT1G27120 | B | 13 | 0.74 |
| 120 | 57 | 222 | BDL_unnamed_351 | arabidopsis\|6\|AT1G27120 | C | 15 | 0.79 |
| 121 | 57 | 222 | BDL_unnamed_351 | arabidopsis\|6\|AT1G27120 | C | 16 | 0.82 |
| 122 | 57 | 222 | BDL_unnamed_351 | arabidopsis\|6\|AT1G27120 | D | 17 | 0.74 |
| 123 | 58 | 223 | BDL_unnamed_352 | arabidopsis\|6\|AT5G01820 | B | 4 | −0.71 |
| 124 | 58 | 223 | BDL_unnamed_352 | arabidopsis\|6\|AT5G01820 | B | 8 | −0.7 |
| 125 | 58 | 223 | BDL_unnamed_352 | arabidopsis\|6\|AT5G01820 | C | 15 | −0.74 |
| 126 | 58 | 223 | BDL_unnamed_352 | arabidopsis\|6\|AT5G01820 | E | 16 | 0.71 |
| 127 | 60 | 225 | BDL_unnamed_354 | arabidopsis\|6\|AT3G16490 | C | 16 | 0.73 |
| 128 | 61 | 226 | BDL_unnamed_355 | arabidopsis\|6\|AT5G23050 | D | 12 | 0.72 |
| 129 | 62 | 227 | BDL_unnamed_356 | arabidopsis\|6\|AT4G16050 | E | 11 | 0.95 |
| 130 | 62 | 227 | BDL_unnamed_356 | arabidopsis\|6\|AT4G16050 | E | 14 | 0.77 |
| 131 | 63 | 228 | BDL_unnamed_357 | arabidopsis\|6\|AT1G44760 | B | 15 | 0.73 |
| 132 | 63 | 228 | BDL_unnamed_357 | arabidopsis\|6\|AT1G44760 | B | 16 | 0.7 |
| 133 | 64 | 229 | BDL_unnamed_358 | arabidopsis\|6\|AT3G01570 | C | 16 | 0.71 |
| 134 | 66 | 231 | BDL_unnamed_362 | arabidopsis\|6\|AT2G25940 | B | 15 | 0.83 |
| 135 | 66 | 231 | BDL_unnamed_362 | arabidopsis\|6\|AT2G25940 | B | 16 | 0.84 |
| 136 | 67 | 232 | BDL_unnamed_364 | arabidopsis\|6\|AT1G04660 | D | 12 | 0.88 |
| 137 | 67 | 232 | BDL_unnamed_364 | arabidopsis\|6\|AT1G04660 | D | 15 | 0.84 |
| 138 | 67 | 232 | BDL_unnamed_364 | arabidopsis\|6\|AT1G04660 | D | 16 | 0.91 |
| 139 | 68 | 233 | BDL_unnamed_365 | arabidopsis\|6\|AT1G05160 | C | 16 | 0.71 |
| 140 | 68 | 233 | BDL_unnamed_365 | arabidopsis\|6\|AT1G05160 | D | 15 | 0.72 |
| 141 | 68 | 233 | BDL_unnamed_365 | arabidopsis\|6\|AT1G05160 | D | 16 | 0.72 |
| 142 | 70 | 235 | BDL_unnamed_367 | arabidopsis\|6\|AT1G19900 | B | 6 | 0.8 |
| 143 | 70 | 235 | BDL_unnamed_367 | arabidopsis\|6\|AT1G19900 | C | 12 | −0.86 |
| 144 | 70 | 235 | BDL_unnamed_367 | arabidopsis\|6\|AT1G19900 | C | 14 | 0.73 |
| 145 | 70 | 235 | BDL_unnamed_367 | arabidopsis\|6\|AT1G19900 | E | 15 | 0.71 |
| 146 | 71 | 236 | BDL_unnamed_368 | arabidopsis\|6\|AT1G23200 | D | 13 | −0.78 |
| 147 | 71 | 236 | BDL_unnamed_368 | arabidopsis\|6\|AT1G23200 | E | 17 | −0.73 |
| 148 | 72 | 237 | BDL_unnamed_369 | arabidopsis\|6\|AT1G26680 | A | 1 | 0.84 |
| 149 | 72 | 237 | BDL_unnamed_369 | arabidopsis\|6\|AT1G26680 | A | 2 | 0.75 |
| 150 | 73 | 238 | BDL_unnamed_370 | arabidopsis\|6\|AT1G28590 | E | 11 | 0.9 |

TABLE 7-continued

*Arabidopsis* selected genes and their correlation with yield components among different transcriptom sets

| | Nucleotide SEQ ID NO: | Polypeptide SEQ ID NO: | Gene Name | Cluster Name | Exp. Set | Correl. Vector | R |
|---|---|---|---|---|---|---|---|
| 151 | 73 | 238 | BDL_unnamed_370 | arabidopsis\|6\|AT1G28590 | E | 12 | −0.72 |
| 152 | 74 | 239 | BDL_unnamed_371 | arabidopsis\|6\|AT1G48910 | B | 12 | 0.72 |
| 153 | 74 | 239 | BDL_unnamed_371 | arabidopsis\|6\|AT1G48910 | B | 15 | 0.79 |
| 154 | 74 | 239 | BDL_unnamed_371 | arabidopsis\|6\|AT1G48910 | B | 16 | 0.86 |
| 155 | 74 | 239 | BDL_unnamed_371 | arabidopsis\|6\|AT1G48910 | C | 17 | 0.79 |
| 156 | 79 | 244 | BDL_unnamed_374 | arabidopsis\|6\|AT1G62610 | D | 15 | −0.74 |
| 157 | 80 | 245 | BDL_unnamed_375 | arabidopsis\|6\|AT1G76290 | B | 16 | 0.72 |
| 158 | 80 | 245 | BDL_unnamed_375 | arabidopsis\|6\|AT1G76290 | C | 17 | 0.77 |
| 159 | 81 | 246 | BDL_unnamed_376 | arabidopsis\|6\|AT1G68470 | B | 4 | 0.76 |
| 160 | 81 | 246 | BDL_unnamed_376 | arabidopsis\|6\|AT1G68470 | B | 5 | 0.77 |
| 161 | 81 | 246 | BDL_unnamed_376 | arabidopsis\|6\|AT1G68470 | B | 8 | 0.96 |
| 162 | 81 | 246 | BDL_unnamed_376 | arabidopsis\|6\|AT1G68470 | B | 10 | 0.89 |
| 163 | 81 | 246 | BDL_unnamed_376 | arabidopsis\|6\|AT1G68470 | C | 15 | 0.83 |
| 164 | 81 | 246 | BDL_unnamed_376 | arabidopsis\|6\|AT1G68470 | C | 16 | 0.74 |
| 165 | 81 | 246 | BDL_unnamed_376 | arabidopsis\|6\|AT1G68470 | D | 13 | −0.81 |
| 166 | 81 | 246 | BDL_unnamed_376 | arabidopsis\|6\|AT1G68470 | D | 14 | −0.82 |
| 167 | 82 | 247 | BDL_unnamed_377 | arabidopsis\|6\|AT1G71250 | E | 11 | 0.72 |
| 168 | 82 | 247 | BDL_unnamed_377 | arabidopsis\|6\|AT1G71250 | E | 14 | 0.8 |
| 169 | 82 | 247 | BDL_unnamed_377 | arabidopsis\|6\|AT1G71250 | E | 17 | −0.7 |
| 170 | 83 | 248 | BDL_unnamed_379 | arabidopsis\|6\|AT3G58200 | B | 6 | 0.75 |
| 171 | 84 | 249 | BDL_unnamed_380 | arabidopsis\|6\|AT1G78500 | A | 1 | −0.74 |
| 172 | 84 | 249 | BDL_unnamed_380 | arabidopsis\|6\|AT1G78500 | B | 7 | 0.75 |
| 173 | 84 | 249 | BDL_unnamed_380 | arabidopsis\|6\|AT1G78500 | B | 18 | 0.84 |
| 174 | 85 | 250 | BDL_unnamed_381 | arabidopsis\|6\|AT2G14690 | E | 15 | −0.72 |
| 175 | 88 | 253 | BDL_unnamed_384 | arabidopsis\|6\|AT2G23510 | B | 12 | 0.74 |
| 176 | 88 | 253 | BDL_unnamed_384 | arabidopsis\|6\|AT2G23510 | B | 15 | 0.71 |
| 177 | 88 | 253 | BDL_unnamed_384 | arabidopsis\|6\|AT2G23510 | B | 16 | 0.8 |
| 178 | 89 | 254 | BDL_unnamed_385 | arabidopsis\|6\|AT2G26070 | B | 15 | 0.91 |
| 179 | 89 | 254 | BDL_unnamed_385 | arabidopsis\|6\|AT2G26070 | B | 16 | 0.88 |
| 180 | 90 | 255 | BDL_unnamed_386 | arabidopsis\|6\|AT2G28650 | D | 13 | −0.93 |
| 181 | 90 | 255 | BDL_unnamed_386 | arabidopsis\|6\|AT2G28650 | D | 14 | −0.87 |
| 182 | 90 | 255 | BDL_unnamed_386 | arabidopsis\|6\|AT2G28650 | E | 15 | 0.7 |
| 183 | 91 | 256 | BDL_unnamed_388 | arabidopsis\|6\|AT2G41290 | E | 11 | 0.78 |
| 184 | 93 | 258 | BDL_unnamed_390 | arabidopsis\|6\|AT2G47750 | B | 8 | 0.79 |
| 185 | 93 | 258 | BDL_unnamed_390 | arabidopsis\|6\|AT2G47750 | D | 14 | 0.84 |
| 186 | 93 | 258 | BDL_unnamed_390 | arabidopsis\|6\|AT2G47750 | E | 14 | 0.71 |
| 187 | 93 | 258 | BDL_unnamed_390 | arabidopsis\|6\|AT2G47750 | E | 17 | −0.79 |
| 188 | 94 | 259 | BDL_unnamed_391 | arabidopsis\|6\|AT3G03230 | D | 15 | 0.96 |
| 189 | 94 | 259 | BDL_unnamed_391 | arabidopsis\|6\|AT3G03230 | D | 16 | 0.95 |
| 190 | 94 | 259 | BDL_unnamed_391 | arabidopsis\|6\|AT3G03230 | E | 14 | −0.73 |
| 191 | 95 | 260 | BDL_unnamed_392 | arabidopsis\|6\|AT3G04200 | B | 7 | 0.85 |
| 192 | 95 | 260 | BDL_unnamed_392 | arabidopsis\|6\|AT3G04200 | B | 9 | −0.94 |
| 193 | 95 | 260 | BDL_unnamed_392 | arabidopsis\|6\|AT3G04200 | B | 13 | 0.78 |
| 194 | 98 | 263 | BDL_unnamed_395 | arabidopsis\|6\|AT3G49380 | B | 4 | −0.78 |
| 195 | 98 | 263 | BDL_unnamed_395 | arabidopsis\|6\|AT3G49380 | B | 9 | −0.77 |
| 196 | 98 | 263 | BDL_unnamed_395 | arabidopsis\|6\|AT3G49380 | B | 10 | −0.73 |
| 197 | 98 | 263 | BDL_unnamed_395 | arabidopsis\|6\|AT3G49380 | B | 17 | 0.88 |
| 198 | 98 | 263 | BDL_unnamed_395 | arabidopsis\|6\|AT3G49380 | C | 12 | 0.71 |
| 199 | 98 | 263 | BDL_unnamed_395 | arabidopsis\|6\|AT3G49380 | C | 15 | 0.75 |
| 200 | 98 | 263 | BDL_unnamed_395 | arabidopsis\|6\|AT3G49380 | C | 16 | 0.82 |
| 201 | 98 | 263 | BDL_unnamed_395 | arabidopsis\|6\|AT3G49380 | E | 11 | 0.82 |
| 202 | 104 | 269 | BDL_unnamed_400 | arabidopsis\|6\|AT4G33600 | B | 12 | 0.8 |
| 203 | 104 | 269 | BDL_unnamed_400 | arabidopsis\|6\|AT4G33600 | E | 11 | 0.84 |
| 204 | 104 | 269 | BDL_unnamed_400 | arabidopsis\|6\|AT4G33600 | E | 14 | 0.8 |
| 205 | 106 | 271 | BDL_unnamed_402 | arabidopsis\|6\|AT5G08460 | D | 15 | 0.77 |
| 206 | 106 | 271 | BDL_unnamed_402 | arabidopsis\|6\|AT5G08460 | D | 16 | 0.78 |
| 207 | 107 | 272 | BDL_unnamed_403 | arabidopsis\|6\|AT2G34700 | C | 11 | 0.89 |
| 208 | 107 | 272 | BDL_unnamed_403 | arabidopsis\|6\|AT2G34700 | C | 12 | −0.71 |
| 209 | 108 | 273 | BDL_unnamed_404 | arabidopsis\|6\|AT5G15740 | B | 5 | 0.74 |
| 210 | 108 | 273 | BDL_unnamed_404 | arabidopsis\|6\|AT5G15740 | B | 8 | 0.71 |
| 211 | 108 | 273 | BDL_unnamed_404 | arabidopsis\|6\|AT5G15740 | E | 15 | 0.8 |
| 212 | 109 | 274 | BDL_unnamed_405 | arabidopsis\|6\|AT5G16230 | A | 1 | −0.75 |
| 213 | 109 | 274 | BDL_unnamed_405 | arabidopsis\|6\|AT5G16230 | B | 8 | 0.83 |
| 214 | 109 | 274 | BDL_unnamed_405 | arabidopsis\|6\|AT5G16230 | C | 12 | −0.8 |
| 215 | 109 | 274 | BDL_unnamed_405 | arabidopsis\|6\|AT5G16230 | D | 12 | 0.73 |
| 216 | 109 | 274 | BDL_unnamed_405 | arabidopsis\|6\|AT5G16230 | D | 16 | 0.74 |
| 217 | 110 | 275 | BDL_unnamed_406 | arabidopsis\|6\|AT5G18290 | E | 11 | −0.76 |
| 218 | 112 | 277 | BDL_unnamed_408 | arabidopsis\|6\|AT5G39130 | B | 12 | 0.79 |
| 219 | 112 | 277 | BDL_unnamed_408 | arabidopsis\|6\|AT5G39130 | B | 13 | 0.76 |
| 220 | 112 | 277 | BDL_unnamed_408 | arabidopsis\|6\|AT5G39130 | B | 16 | 0.79 |
| 221 | 112 | 277 | BDL_unnamed_408 | arabidopsis\|6\|AT5G39130 | C | 14 | 0.79 |
| 222 | 112 | 277 | BDL_unnamed_408 | arabidopsis\|6\|AT5G39130 | D | 14 | 0.79 |
| 223 | 112 | 277 | BDL_unnamed_408 | arabidopsis\|6\|AT5G39130 | E | 12 | 0.73 |

TABLE 7-continued

Arabidopsis selected genes and their correlation with yield components among different transcriptom sets

| | Nucleotide SEQ ID NO: | Polypeptide SEQ ID NO: | Gene Name | Cluster Name | Exp. Set | Correl. Vector | R |
|---|---|---|---|---|---|---|---|
| 224 | 114 | 279 | BDL_unnamed_409 | arabidopsis\|6\|AT5G39160 | B | 12 | 0.79 |
| 225 | 114 | 279 | BDL_unnamed_409 | arabidopsis\|6\|AT5G39160 | B | 13 | 0.76 |
| 226 | 114 | 279 | BDL_unnamed_409 | arabidopsis\|6\|AT5G39160 | B | 16 | 0.79 |
| 227 | 114 | 279 | BDL_unnamed_409 | arabidopsis\|6\|AT5G39160 | C | 14 | 0.79 |
| 228 | 114 | 279 | BDL_unnamed_409 | arabidopsis\|6\|AT5G39160 | D | 14 | 0.79 |
| 229 | 114 | 279 | BDL_unnamed_409 | arabidopsis\|6\|AT5G39160 | E | 12 | 0.73 |
| 230 | 115 | 280 | BDL_unnamed_410 | arabidopsis\|6\|AT5G39190 | B | 12 | 0.79 |
| 231 | 115 | 280 | BDL_unnamed_410 | arabidopsis\|6\|AT5G39190 | B | 13 | 0.76 |
| 232 | 115 | 280 | BDL_unnamed_410 | arabidopsis\|6\|AT5G39190 | B | 16 | 0.79 |
| 233 | 115 | 280 | BDL_unnamed_410 | arabidopsis\|6\|AT5G39190 | C | 14 | 0.79 |
| 234 | 115 | 280 | BDL_unnamed_410 | arabidopsis\|6\|AT5G39190 | D | 14 | 0.79 |
| 235 | 115 | 280 | BDL_unnamed_410 | arabidopsis\|6\|AT5G39190 | E | 12 | 0.73 |
| 236 | 116 | 281 | BDL_unnamed_411 | arabidopsis\|6\|AT5G44360 | B | 10 | −0.74 |
| 237 | 117 | 282 | BDL_unnamed_412 | arabidopsis\|6\|AT5G47670 | E | 11 | 0.86 |
| 238 | 117 | 282 | BDL_unnamed_412 | arabidopsis\|6\|AT5G47670 | E | 14 | 0.72 |
| 239 | 119 | 284 | BDL_unnamed_414 | arabidopsis\|6\|AT5G56300 | C | 15 | 0.77 |
| 240 | 119 | 284 | BDL_unnamed_414 | arabidopsis\|6\|AT5G56300 | C | 16 | 0.78 |
| 241 | 119 | 284 | BDL_unnamed_414 | arabidopsis\|6\|AT5G56300 | D | 15 | 0.78 |
| 242 | 119 | 284 | BDL_unnamed_414 | arabidopsis\|6\|AT5G56300 | D | 16 | 0.82 |
| 243 | 121 | 286 | BDL_unnamed_418 | arabidopsis\|6\|AT1G28640 | B | 18 | 0.81 |
| 244 | 122 | 287 | BDL_unnamed_419 | arabidopsis\|6\|AT1G22990 | E | 11 | 0.95 |
| 245 | 122 | 287 | BDL_unnamed_419 | arabidopsis\|6\|AT1G22990 | E | 14 | 0.8 |
| 246 | 123 | 288 | BDL_unnamed_420 | arabidopsis\|6\|AT1G64110 | B | 6 | 0.78 |
| 247 | 125 | 290 | BDL_unnamed_421 | arabidopsis\|6\|AT1G04380 | D | 15 | 0.73 |
| 248 | 126 | 291 | BDL_unnamed_422 | arabidopsis\|6\|AT1G08810 | B | 8 | 0.8 |
| 249 | 126 | 291 | BDL_unnamed_422 | arabidopsis\|6\|AT1G08810 | D | 14 | −0.79 |
| 250 | 126 | 291 | BDL_unnamed_422 | arabidopsis\|6\|AT1G08810 | D | 15 | −0.82 |
| 251 | 126 | 291 | BDL_unnamed_422 | arabidopsis\|6\|AT1G08810 | D | 16 | −0.82 |
| 252 | 128 | 293 | BDL_unnamed_423 | arabidopsis\|6\|AT1G28170 | B | 16 | −0.71 |
| 253 | 128 | 293 | BDL_unnamed_423 | arabidopsis\|6\|AT1G28170 | C | 11 | 0.78 |
| 254 | 128 | 293 | BDL_unnamed_423 | arabidopsis\|6\|AT1G28170 | C | 12 | −0.79 |
| 255 | 128 | 293 | BDL_unnamed_423 | arabidopsis\|6\|AT1G28170 | C | 14 | 0.75 |
| 256 | 130 | 295 | BDL_unnamed_425 | arabidopsis\|6\|AT3G10590 | E | 13 | 0.72 |
| 257 | 131 | 296 | BDL_unnamed_426 | arabidopsis\|6\|AT3G58740 | E | 14 | 0.75 |
| 258 | 131 | 296 | BDL_unnamed_426 | arabidopsis\|6\|AT3G58740 | E | 17 | −0.72 |
| 259 | 132 | 297 | BDL_unnamed_427 | arabidopsis\|6\|AT4G02360 | A | 1 | 0.85 |
| 260 | 132 | 297 | BDL_unnamed_427 | arabidopsis\|6\|AT4G02360 | A | 2 | 0.76 |
| 261 | 134 | 299 | BDL_unnamed_429 | arabidopsis\|6\|AT5G07200 | C | 13 | −0.76 |
| 262 | 134 | 299 | BDL_unnamed_429 | arabidopsis\|6\|AT5G07200 | D | 15 | 0.73 |
| 263 | 134 | 299 | BDL_unnamed_429 | arabidopsis\|6\|AT5G07200 | D | 16 | 0.73 |
| 264 | 135 | 300 | BDL_unnamed_430 | arabidopsis\|6\|AT5G22810 | D | 12 | 0.86 |
| 265 | 135 | 300 | BDL_unnamed_430 | arabidopsis\|6\|AT5G22810 | D | 15 | 0.71 |
| 266 | 135 | 300 | BDL_unnamed_430 | arabidopsis\|6\|AT5G22810 | D | 16 | 0.8 |
| 267 | 136 | 301 | BDL_unnamed_431 | arabidopsis\|6\|AT5G43860 | A | 11 | 0.75 |
| 268 | 136 | 301 | BDL_unnamed_431 | arabidopsis\|6\|AT5G43860 | A | 13 | −0.77 |
| 269 | 136 | 301 | BDL_unnamed_431 | arabidopsis\|6\|AT5G43860 | C | 11 | 0.72 |
| 270 | 136 | 301 | BDL_unnamed_431 | arabidopsis\|6\|AT5G43860 | C | 17 | −0.7 |
| 271 | 136 | 301 | BDL_unnamed_431 | arabidopsis\|6\|AT5G43860 | D | 14 | 0.71 |
| 272 | 137 | 302 | BDL_unnamed_432 | arabidopsis\|6\|AT5G57390 | C | 15 | 0.72 |
| 273 | 137 | 302 | BDL_unnamed_432 | arabidopsis\|6\|AT5G57390 | C | 16 | 0.76 |
| 274 | 137 | 302 | BDL_unnamed_432 | arabidopsis\|6\|AT5G57390 | D | 17 | 0.71 |
| 275 | 138 | 303 | BDL_unnamed_433 | arabidopsis\|6\|AT5G62800 | D | 11 | 0.76 |
| 276 | 138 | 303 | BDL_unnamed_433 | arabidopsis\|6\|AT5G62800 | E | 17 | −0.73 |
| 277 | 139 | 304 | BDL_unnamed_435 | arabidopsis\|6\|AT5G52500 | B | 5 | −0.75 |
| 278 | 139 | 304 | BDL_unnamed_435 | arabidopsis\|6\|AT5G52500 | B | 8 | −0.73 |
| 279 | 140 | 305 | BDL_unnamed_436 | arabidopsis\|6\|AT5G24600 | A | 3 | −0.78 |
| 280 | 143 | 308 | BDL_unnamed_438 | arabidopsis\|6\|AT1G72040 | D | 13 | 0.71 |
| 281 | 145 | 310 | BDL_unnamed_440 | arabidopsis\|6\|AT1G50510 | B | 8 | 0.75 |
| 282 | 146 | 311 | BDL_unnamed_441 | arabidopsis\|6\|AT5G48100 | E | 17 | −0.77 |
| 283 | 147 | 312 | BDL_unnamed_442 | arabidopsis\|6\|AT1G14760 | B | 6 | 0.83 |
| 284 | 147 | 312 | BDL_unnamed_442 | arabidopsis\|6\|AT1G14760 | B | 7 | −0.76 |
| 285 | 147 | 312 | BDL_unnamed_442 | arabidopsis\|6\|AT1G14760 | B | 9 | 0.75 |
| 286 | 148 | 313 | BDL_unnamed_443 | arabidopsis\|6\|AT1G15150 | B | 11 | 0.9 |
| 287 | 148 | 313 | BDL_unnamed_443 | arabidopsis\|6\|AT1G15150 | E | 11 | 0.76 |
| 288 | 149 | 314 | BDL_unnamed_444 | arabidopsis\|6\|AT1G20500 | D | 13 | −0.78 |
| 289 | 150 | 315 | BDL_unnamed_445 | arabidopsis\|6\|AT1G56170 | B | 6 | 0.73 |
| 290 | 150 | 315 | BDL_unnamed_445 | arabidopsis\|6\|AT1G56170 | D | 15 | 0.94 |
| 291 | 150 | 315 | BDL_unnamed_445 | arabidopsis\|6\|AT1G56170 | D | 16 | 0.93 |
| 292 | 151 | 316 | BDL_unnamed_446 | arabidopsis\|6\|AT1G62070 | A | 1 | 0.77 |
| 293 | 151 | 316 | BDL_unnamed_446 | arabidopsis\|6\|AT1G62070 | A | 2 | 0.77 |
| 294 | 153 | 318 | BDL_unnamed_448 | arabidopsis\|6\|AT3G21090 | C | 13 | 0.9 |
| 295 | 154 | 319 | BDL_unnamed_449 | arabidopsis\|6\|AT3G24250 | B | 6 | 0.8 |
| 296 | 154 | 319 | BDL_unnamed_449 | arabidopsis\|6\|AT3G24250 | C | 11 | 0.73 |

TABLE 7-continued

Arabidopsis selected genes and their correlation with yield components among different transcriptom sets

| | Nucleotide SEQ ID NO: | Polypeptide SEQ ID NO: | Gene Name | Cluster Name | Exp. Set | Correl. Vector | R |
|---|---|---|---|---|---|---|---|
| 297 | 155 | 320 | BDL__unnamed__450 | arabidopsis\|6\|AT3G50990 | D | 13 | −0.85 |
| 298 | 157 | 322 | BDL__unnamed__452 | arabidopsis\|6\|AT4G10150 | B | 17 | −0.75 |
| 299 | 159 | 324 | BDL__unnamed__454 | arabidopsis\|6\|AT5G07190 | B | 17 | 0.77 |
| 300 | 159 | 324 | BDL__unnamed__454 | arabidopsis\|6\|AT5G07190 | B | 18 | 0.82 |
| 301 | 159 | 324 | BDL__unnamed__454 | arabidopsis\|6\|AT5G07190 | D | 15 | −0.92 |
| 302 | 159 | 324 | BDL__unnamed__454 | arabidopsis\|6\|AT5G07190 | D | 16 | −0.91 |
| 303 | 160 | 325 | BDL__unnamed__455 | arabidopsis\|6\|AT5G10220 | A | 10 | −0.72 |
| 304 | 160 | 325 | BDL__unnamed__455 | arabidopsis\|6\|AT5G10220 | E | 16 | −0.72 |
| 305 | 161 | 326 | BDL__unnamed__456 | arabidopsis\|6\|AT5G20940 | D | 15 | 0.76 |
| 306 | 161 | 326 | BDL__unnamed__456 | arabidopsis\|6\|AT5G20940 | D | 16 | 0.7 |
| 307 | 162 | 327 | BDL__unnamed__457 | arabidopsis\|6\|AT5G51210 | C | 17 | 0.81 |
| 308 | 163 | 328 | BDL__unnamed__458 | arabidopsis\|6\|AT5G55620 | A | 13 | −0.76 |
| 309 | 163 | 328 | BDL__unnamed__458 | arabidopsis\|6\|AT5G55620 | E | 11 | −0.81 |
| 310 | 163 | 328 | BDL__unnamed__458 | arabidopsis\|6\|AT5G55620 | E | 14 | −0.71 |
| 311 | 164 | 329 | BDL__unnamed__459 | arabidopsis\|6\|AT5G60460 | C | 14 | 0.84 |
| 312 | 164 | 329 | BDL__unnamed__459 | arabidopsis\|6\|AT5G60460 | E | 17 | −0.72 |
| 313 | 165 | 330 | BDL__unnamed__460 | arabidopsis\|6\|AT5G65590 | D | 16 | 0.72 |

Table 7. Correlation vector (correl. Vector).

The following Tables 8-15 present polynucleotides which are predicted based on the microarray correlation analysis to increase in a plant the seed yield (Table 8), oil yield (Table 9), growth rate (Table 10), organ shape/size/length (Table 11), harvest index (Table 12), oil content per seed (Table 13), plant dry matter (Table 14) and seed number per silique (Table 15). It should be noted that additional polynucleotides described in the instant application can be used to change the above characteristics in plants.

TABLE 8

Polynucleotides which impact seed yield

| Polynucleotide SEQ ID NO: | SEQ ID NO: of the polypeptide encoded by the polynucleotide | Gene Name |
|---|---|---|
| 1 | 3 | 168 | BDL2 |
| 2 | 8 | 173 | BDL8 |
| 3 | 9 | 174 | BDL9 |
| 4 | 14 | 179 | BDL15 |
| 5 | 16 | 181 | BDL17 |
| 6 | 26 | 191 | BDL26a |
| 7 | 27 | 192 | BDL26b |
| 8 | 29 | 194 | BDL28 |
| 9 | 30 | 195 | BDL29 |
| 10 | 39 | 204 | BDL__unnamed__334 |
| 11 | 42 | 207 | BDL__unnamed__337 |
| 12 | 50 | 215 | BDL__unnamed__344 |
| 13 | 53 | 218 | BDL__unnamed__347 |
| 14 | 55 | 220 | BDL__unnamed__349 |
| 15 | 56 | 221 | BDL__unnamed__350 |
| 16 | 57 | 222 | BDL__unnamed__351 |
| 17 | 63 | 228 | BDL__unnamed__357 |
| 18 | 66 | 231 | BDL__unnamed__362 |
| 19 | 68 | 233 | BDL__unnamed__365 |
| 20 | 70 | 235 | BDL__unnamed__367 |
| 21 | 74 | 239 | BDL__unnamed__371 |
| 22 | 79 | 244 | BDL__unnamed__374 |
| 23 | 81 | 246 | BDL__unnamed__376 |
| 24 | 88 | 253 | BDL__unnamed__384 |
| 25 | 89 | 254 | BDL__unnamed__385 |
| 26 | 94 | 259 | BDL__unnamed__391 |
| 27 | 98 | 263 | BDL__unnamed__395 |
| 28 | 106 | 271 | BDL__unnamed__402 |
| 29 | 108 | 273 | BDL__unnamed__404 |
| 30 | 119 | 284 | BDL__unnamed__414 |

TABLE 8-continued

Polynucleotides which impact seed yield

| Polynucleotide SEQ ID NO: | SEQ ID NO: of the polypeptide encoded by the polynucleotide | Gene Name |
|---|---|---|
| 31 | 125 | 290 | BDL__unnamed__421 |
| 32 | 126 | 291 | BDL__unnamed__422 |
| 33 | 134 | 299 | BDL__unnamed__429 |
| 34 | 137 | 302 | BDL__unnamed__432 |
| 35 | 150 | 315 | BDL__unnamed__445 |
| 36 | 159 | 324 | BDL__unnamed__454 |
| 37 | 161 | 326 | BDL__unnamed__456 |

Table 8.

TABLE 9

Polynucleotides which impact oil yield

| Polynucleotide SEQ ID NO: | SEQ ID NO: of the polypeptide encoded by the polynucleotide | Gene Name |
|---|---|---|
| 1 | 18 | 183 | BDL19 |
| 2 | 25 | 190 | BDL25 |
| 3 | 49 | 214 | BDL__unnamed__343 |
| 4 | 57 | 222 | BDL__unnamed__351 |
| 5 | 60 | 225 | BDL__unnamed__354 |
| 6 | 64 | 229 | BDL__unnamed__358 |
| 7 | 67 | 232 | BDL__unnamed__364 |
| 8 | 109 | 274 | BDL__unnamed__405 |
| 9 | 135 | 300 | BDL__unnamed__430 |
| 10 | 160 | 325 | BDL__unnamed__455 |
| 11 | 165 | 330 | BDL__unnamed__460 |

Table 9.

TABLE 10

Polynucleotides which impact growth rate

| | Polynucleotide SEQ ID NO: | SEQ ID NO: of the polypeptide encoded by the polynucleotide | Gene Name |
|---|---|---|---|
| 1 | 36 | 201 | BDL_unnamed_330 |
| 2 | 70 | 235 | BDL_unnamed_367 |
| 3 | 83 | 248 | BDL_unnamed_379 |
| 4 | 123 | 288 | BDL_unnamed_420 |
| 5 | 140 | 305 | BDL_unnamed_436 |
| 6 | 147 | 312 | BDL_unnamed_442 |
| 7 | 150 | 315 | BDL_unnamed_445 |
| 8 | 154 | 319 | BDL_unnamed_449 |

Table 10

TABLE 11

Polynucleotides which impact organ shape/size/length

| | Polynucleotide SEQ ID NO: | SEQ ID NO: of the polypeptide encoded by the polynucleotide | Gene Name |
|---|---|---|---|
| 1 | 10 | 175 | BDL10 |
| 2 | 13 | 178 | BDL14 |
| 3 | 19 | 184 | BDL20a |
| 4 | 20 | 185 | BDL20b |
| 5 | 21 | 186 | BDL21 |
| 6 | 22 | 187 | BDL22 |
| 7 | 28 | 193 | BDL27 |
| 8 | 38 | 203 | BDL_unnamed_333 |
| 9 | 40 | 205 | BDL_unnamed_335 |
| 10 | 40 | 205 | BDL_unnamed_335 |
| 11 | 43 | 208 | BDL_unnamed_339 |
| 12 | 44 | 209 | BDL_unnamed_340 |
| 13 | 62 | 227 | BDL_unnamed_356 |
| 14 | 72 | 237 | BDL_unnamed_369 |
| 15 | 73 | 238 | BDL_unnamed_370 |
| 16 | 81 | 246 | BDL_unnamed_376 |
| 17 | 82 | 247 | BDL_unnamed_377 |
| 18 | 84 | 249 | BDL_unnamed_380 |
| 19 | 91 | 256 | BDL_unnamed_388 |
| 20 | 93 | 258 | BDL_unnamed_390 |
| 21 | 95 | 260 | BDL_unnamed_392 |
| 22 | 104 | 269 | BDL_unnamed_400 |
| 23 | 109 | 274 | BDL_unnamed_405 |
| 24 | 110 | 275 | BDL_unnamed_406 |
| 25 | 116 | 281 | BDL_unnamed_411 |
| 26 | 117 | 282 | BDL_unnamed_412 |
| 27 | 121 | 286 | BDL_unnamed_418 |
| 28 | 122 | 287 | BDL_unnamed_419 |
| 29 | 126 | 291 | BDL_unnamed_422 |
| 30 | 128 | 293 | BDL_unnamed_423 |
| 31 | 132 | 297 | BDL_unnamed_427 |
| 32 | 136 | 301 | BDL_unnamed_431 |
| 33 | 138 | 303 | BDL_unnamed_433 |
| 34 | 145 | 310 | BDL_unnamed_440 |
| 35 | 148 | 313 | BDL_unnamed_443 |
| 36 | 151 | 316 | BDL_unnamed_446 |
| 37 | 154 | 319 | BDL_unnamed_449 |
| 38 | 163 | 328 | BDL_unnamed_458 |

Table 11. Organ shape/size/length include for example, leaf length, leaf width, leaf circularity, seed size, or root length.

TABLE 12

Polynucleotides which impact harvest index

| | Polynucleotide SEQ ID NO: | SEQ ID NO: of the polypeptide encoded by the polynucleotide | Gene Name |
|---|---|---|---|
| 1 | 7 | 172 | BDL7 |
| 2 | 18 | 183 | BDL19 |
| 3 | 36 | 201 | BDL_unnamed_330 |
| 4 | 46 | 211 | BDL_unnamed_341 |
| 5 | 56 | 221 | BDL_unnamed_350 |
| 6 | 80 | 245 | BDL_unnamed_375 |
| 7 | 93 | 258 | BDL_unnamed_390 |
| 8 | 98 | 263 | BDL_unnamed_395 |
| 9 | 131 | 296 | BDL_unnamed_426 |
| 10 | 136 | 301 | BDL_unnamed_431 |
| 11 | 138 | 303 | BDL_unnamed_433 |
| 12 | 146 | 311 | BDL_unnamed_441 |
| 13 | 157 | 322 | BDL_unnamed_452 |
| 14 | 162 | 327 | BDL_unnamed_457 |
| 15 | 164 | 329 | BDL_unnamed_459 |

Table 12

TABLE 13

Polynucleotides which impact oil content per seed

| | Polynucleotide SEQ ID NO: | SEQ ID NO: of the polypeptide encoded by the polynucleotide | Gene Name |
|---|---|---|---|
| 1 | 6 | 171 | BDL6 |
| 2 | 23 | 188 | BDL23 |
| 3 | 56 | 221 | BDL_unnamed_350 |
| 4 | 61 | 226 | BDL_unnamed_355 |
| 5 | 112 | 277 | BDL_unnamed_408 |
| 6 | 114 | 279 | BDL_unnamed_409 |
| 7 | 115 | 280 | BDL_unnamed_410 |
| 8 | 128 | 293 | BDL_unnamed_423 |
| 9 | 135 | 300 | BDL_unnamed_430 |

Table 13

TABLE 14

Polynucleotides which impact plant dry matter

| | Polynucleotide SEQ ID NO: | SEQ ID NO: of the polypeptide encoded by the polynucleotide | Gene Name |
|---|---|---|---|
| 1 | 37 | 202 | BDL_unnamed_331 |
| 2 | 52 | 217 | BDL_unnamed_346 |
| 3 | 55 | 220 | BDL_unnamed_349 |
| 4 | 139 | 304 | BDL_unnamed_435 |

Table 14

TABLE 15

Polynucleotides which impact seed number per silique

| | Polynucleotide SEQ ID NO: | SEQ ID NO: of the polypeptide encoded by the polynucleotide | Gene Name |
|---|---|---|---|
| 1 | 57 | 222 | BDL_unnamed_351 |
| 2 | 71 | 236 | BDL_unnamed_368 |
| 3 | 81 | 246 | BDL_unnamed_376 |
| 4 | 90 | 255 | BDL_unnamed_386 |
| 5 | 112 | 277 | BDL_unnamed_408 |

TABLE 15-continued

Polynucleotides which impact seed number per silique

| Polynucleotide SEQ ID NO: | SEQ ID NO: of the polypeptide encoded by the polynucleotide | Gene Name |
|---|---|---|
| 6 | 114 | 279 | BDL_unnamed_409 |
| 7 | 115 | 280 | BDL_unnamed_410 |
| 8 | 131 | 296 | BDL_unnamed_426 |
| 9 | 143 | 308 | BDL_unnamed_438 |
| 10 | 149 | 314 | BDL_unnamed_444 |
| 11 | 153 | 318 | BDL_unnamed_448 |
| 12 | 155 | 320 | BDL_unnamed_450 |

Table 15

Example 3

Gene Cloning and Creation of Binary Vectors for Plant Expression

Cloning Strategy

Selected genes from those listed in Examples 1 and 2 above were cloned into binary vectors for the generation of transgenic plants. For cloning, the full-length open reading frame (ORF) was first identified. In case of ORF-EST clusters and in some cases mRNA sequences were analyzed to identify the entire open reading frame by comparing the results of several translation algorithms to known proteins from other plant species. To clone the full-length cDNAs, Reverse Transcription followed by PCR (RT-PCR) was performed on total RNA extracted from *Arabidopsis* siliques collected 3 and 13 days after flowering (3 and 13 DAF). RNA was extracted using Hot Borate RNA Extraction protocol according to World Wide Web (dot) www (dot) eeob (dot) iastate (dot) edu/faculty/WendelJ/ultramicrorna (dot) html. Production of cDNA (using random hexamer and poly dT primers) and PCR amplification was performed using standard protocols described elsewhere (Sambrook J., E. F. Fritsch, and T. Maniatis. 1989. Molecular Cloning. A Laboratory Manual., 2nd Ed. Cold Spring Harbor Laboratory Press, New York.) and are routine for those skilled in the art.

To clone the full-length genomic region of a gene, genomic DNA was extracted from wild type (WT) *Arabidopsis thaliana* leaves (DNeasy plant mini kit, Qiagen, Germany). All genes were amplified by nested PCR. PCR products were purified using Mini Elute PCR purification kit (Qiagen) and sequencing of the amplified PCR products is performed, using ABI 377 sequencer (Applied Biosystems). To facilitate cloning of the cDNAs/genomic sequences, a 8-12 bp extension was added to the 5' prime end of each primer. The primer extension includes an endonuclease restriction site. The restriction sites are selected using two parameters: (a). The site does not exist in the cDNA sequence; and (b). The restriction sites in the forward and reverse primers are designed so the digested cDNA is inserted in the sense formation into the binary vector utilized for transformation.

PCR products were purified (Mini Elute PCR Purification Kit, Qiagen, Germany) and digested with the restriction sites according to the primers used (Roche, Switzerland). The digested PCR products were first subcloned into a high copy vector [(originated from the pBlue-script KS plasmid vector http://www.stratagene.com/manuals/212205.pdf)] with the 35S promoter (SEQ ID NO:921), and the NOS terminator (SEQ ID NO:922) originated from pBI 101.3 binary vector (GenBank Accession No. U12640, by 4417 to 4693)), followed by cloning the entire cassette into the binary vectors pGI or pMBArt (according to Table 16, hereinbelow). The digested PCR products and the linearized plasmid vector were ligated using T4 DNA ligase enzyme (Roche, Switzerland). The following polynucleotides were cloned from RNA extracted from the tissues described above or genomic DNA using the primers as provided in Table 17, below.

TABLE 16

Genes cloned into different binary vectors

| | Bioinf. identified Polynucleotide SEQ ID NO: | Bioinf. identified Polypeptide SEQ ID NO: | TAIR gene name | Internal name | Cloned polynucleotide SEQ ID NO: | Cloned In pGI | Cloned In pMBart |
|---|---|---|---|---|---|---|---|
| 1 | 1 | 166 | AT5G50770 | BDL3 | 1017 | | V |
| 2 | 4 | 169 | AT2G45420 | BDL4 | 1041 | | V |
| 3 | 5 | 170 | AT3G14360 | BDL5 | 1018 | | V |
| 4 | 6 | 171 | AT4G10490 | BDL6 | 1019 | V | |
| 5 | 7 | 172 | AT5G51490 | BDL7 | 1020 | V | |
| 6 | 8 | 173 | AT3G03240 | BDL8 | 1021 | | V |
| 7 | 9 | 174 | AT5G24130 | BDL9 | 1022 | | V |
| 8 | 3 | 168 | AT1G34580 | BDL2 | 1016 | | V |
| 9 | 11 | 176 | AT5G12460 | BDL11 | 1042 | | V |
| 10 | 12 | 177 | AT4G08530 | BDL12 | 1023 | V | |
| 11 | 2 | 167 | AT1G65090 | BDL1 | 1040 | V | |
| 12 | 13 | 178 | AT1G53690 | BDL14 | 1024 | V | |
| 13 | 14 | 179 | AT1G68510 | BDL15 | 1025 | V | |
| 14 | 15 | 180 | AT5G03800 | BDL16 | 1026 | | V |
| 15 | 16 | 181 | AT5G36770 | BDL17 | 1043 | | V |
| 16 | 17 | 182 | AT5G40420 | BDL18 | 1027 | V | |
| 17 | 19 | 184 | AT1G47540.1 | BDL20a | 1029 | V | |
| 18 | 20 | 185 | AT1G47540.2 | BDL20b | 1044 | V | |
| 19 | 21 | 186 | AT3G62730 | BDL21 | 1030 | | V |
| 20 | 23 | 188 | AT3G27785 | BDL23 | 1031 | | V |
| 21 | 24 | 189 | AT5G15000 | BDL24 | 1045 | V | |
| 22 | 25 | 190 | AT3G20910 | BDL25 | 1032 | | V |
| 23 | 26 | 191 | AT1G11170.1 | BDL26a | 1033 | V | |
| 24 | 27 | 192 | AT1G11170.2 | BDL26b | 1034 | V | |
| 25 | 28 | 193 | AT1G68380 | BDL27 | 1035 | | V |

TABLE 16-continued

Genes cloned into different binary vectors

| Bioinf. identified Polynucleotide SEQ ID NO: | Bioinf. identified Polypeptide SEQ ID NO: | TAIR gene name | Internal name | Cloned polynucleotide SEQ ID NO: | Cloned In pGI | Cloned In pMBart |
|---|---|---|---|---|---|---|
| 26 | 29 | 194 | AT1G09380 | BDL28 | 1036 | | V |
| 27 | 30 | 195 | AT1G60970 | BDL29 | 1037 | | V |
| 28 | 31 | 196 | AT1G72580 | BDL30 | 1046 | V | |
| 29 | 33 | 198 | AT2G46960.1 | BDL32a | 1038 | | V |
| 30 | 34 | 199 | AT2G46960.2 | BDL32b | 1039 | | V |
| 31 | 933 | 183 | AT2G02080.1 | BDL19gDNA | 1028 | | V |
| 32 | — | AY254038 | WRINKLED1 | WRI | 1050 | V | |

Table 16: Provided are the sequence identifiers of the polynucleotides and polypeptides identified bioinformatically (bioinf.), as well as the sequence identifiers of the cloned polynucleotides. In two cases, the translated polypeptide sequences of the cloned genes were different from the predicted bioinformatically identified polypeptides (SEQ ID NOs: 176 and 178) and new sequence identifiers were provided (i.e., SEQ ID NO: 1047 for the translated polypeptide of cloned gene SEQ ID NO: 1042 and SEQ ID NO: 1048 for the translated polypeptide of cloned gene SEQ ID NO: 1024).

TABLE 17

Polynucleotides cloned from cDNA libraries, genomic DNA or synthetically produced and the primers used for the cloning

| Gene Name | Restriction Enzymes used for cloning | Primers used for amplification (5'→3') | SEQ ID NO: |
|---|---|---|---|
| BDL3 | SalI, XbaI | Fwd Nested: BDL3_ORF_NF_SalI - AATGTCGACGATGCATGGATTCAATCAACA | 923 |
| | | Fwd External: BDL3_ORF_EF_SalI - TTTGTCGACCATTGTGAAGTATAGTCCTTGATG | 924 |
| | | Rev Nested: BDL3_ORF_NR_XbaI - TATCTAGAACATAAACGGGGAGACTCAAG | 925 |
| | | Rev External: BDL3_ORF_ER_XbaI - AATCTAGACTATGGTAACCCGAAGTTGTATAC | 926 |
| BDL4 | SacI, XbaI | synthetic product | 1041 |
| BDL5 | SalI, XbaI | Fwd Nested: BDL5_ORF_NF_Sal - ACTGTCGACAGACATGCACAAAGACAACG | 927 |
| | | Fwd External: BDL5_ORF_EF_SalI - ATAGTCGACCAAAACCCAGAGACATGCAC | 928 |
| | | Rev Nested: BDL5_ORF_NR_XbaI - AATCTAGACACTTTTCAAAGAGAGGACATCT | 929 |
| | | Rev External: BDL5_ORF_ER_XbaI - ACTCTAGACCGGTTCACTTAAGATTTATTC | 930 |
| BDL6 | SalI, XbaI | Fwd: BDL6_ORF_F1_SalI - AAAGTCGACCAATCATGGCAGCATCAAAAC | 931 |
| | | Rev Nested: BDL6_ORF_NR_XbaI - AGTCTAGACGGATGATTGATTCGATAGTACAC | 932 |
| | | *Phaseolus vulgaris* Rev External: BDL6_ORF_ER_SacI - TGAGCTCCCAATCAAGAACTAAGGACCG | 933 |
| BDL7 | SalI, XbaI | Fwd: BDL7_ORF_F1_Sal - AATGTCGACAACAATGAATATGATGATGCAAAAACTC | 934 |
| | | Rev Nested: BDL7_ORF_NR_XbaI - AATCTAGACGGTCTTTAGAGTCCAGAAGTG | 935 |
| | | Rev External: BDL7_ORF_ER_XbaI - AATCTAGAATCATTGCAACTTAAACACGA | 936 |
| BDL8 | XbaI, SalI | Fwd: BDL8_gDNA_F_Sal - AATGTCGACCCTCTGTCTTGTCTTTTGGTTAGTA | 937 |
| | | Rev: BDL8_gDNA_R_Xb - AATCTAGACCTTCAACTACAAGCGGCTT | 938 |
| BDL9 | SalI, XbaI | Fwd Nested: BDL9_ORF_NF_SalI - acggtcgacCTTACAATAAAATGGTGAAACTCG | 939 |
| | | Fwd External: BDL9_ORF_EF_SalI - aatgtcgacCTCTCTAAACGCATAATCTTACA | 940 |
| | | Rev Nested: BDL9_ORF_NR_XbaI - AATCTAGACAAAATATGTGGTCTCCGCAG | 941 |
| | | Rev External: BDL9_ORF_ER_XbaI - AGTCTAGACAAAAAGGAAACGAATCACA | 942 |

TABLE 17-continued

Polynucleotides cloned from cDNA libraries, genomic DNA or synthetically produced and the primers used for the cloning

| Gene Name | Restriction Enzymes used for cloning | Primers used for amplification (5'→3') | SEQ ID NO: |
|---|---|---|---|
| BDL2 | SalI, XbaI | Fwd Nested: BDL2_ORF_NF_SalI - CAAGTCGACCGTAAGACATAAGCAAAATGGC | 943 |
| | | Fwd External: BDL2_ORF_EF_SalI - TTAGTCGACCACTTCATGCGTAAGACATAAGC | 944 |
| | | Rev Nested: BDL2_ORF_NR_XbaI - GCTCTAGAGCATCTTTTAAGTTGACGTCG | 945 |
| | | Rev External: BDL2_ORF_ER_XbaI - AATCTAGATCCATTGAAAATGCGAACC | 946 |
| BDL11 | SacI, XbaI | synthetic product | |
| BDL12 | SalI, SacI | Fwd Nested: BDL12_gDNA_NF_SalI - AATGTCGACGTTCTATCCCCAACTCTAAATG | 947 |
| | | Fwd External: BDL12_gDNA_EF_XbaI - ATTCTAGATTGTTGTTTGTATCACTTTATTGG | 948 |
| | | Rev Nested: BDL12_gDNA_NR_SacI - AGAGCTCCTTAAAGTTCTATCGAGATAGTGC | 949 |
| | | Rev External: BDL12_gDNA_ER_SacI - AGAGCTCTCAATGAAATTTTACATAACCATC | 950 |
| BDL1 | XbaI, SacI | synthetic product | |
| BDL14 | SalI, XbaI | Fwd: BDL14_ORF_F1_SalI - AATGTCGACAACAATGGATCTACAACAGTCCGAAAC | 951 |
| | | Rev Nested: BDL14_ORF_NR_XbaI - AATCTAGACACTCAGACAGCTGGGTATTAAAC | 952 |
| | | Rev External: BDL14_ORF_ER_SacI - AGAGCTCGTTGTGGCACTCAGACAGCTG | 953 |
| BDL15 | SalI, XbaI | Fwd Nested: BDL15_ORF_NF_Sal - TTCGTCGACAAAGGAATATGAGAATCAGCTG | 954 |
| | | Fwd External: BDL15_ORF_EF_Sal - AACGTCGACCAAACACACATCATACGTATATTTG | 955 |
| | | Rev Nested: BDL15_ORF_NR_XbaI - ATTCTAGAGAGTTTATGATAACCTAATGATTGAC | 956 |
| | | Rev External: BDL15_ORF_ER_XbaI - GTTCTAGACAGAGTGAGTTTATGATAACCTAATG | 957 |
| BDL16 | SalI, XbaI | Fwd: BDL16_ORF_F1_SalI - AATGTCGACAACAATGTCCACCGTTAATCATCAC | 958 |
| | | Rev Nested: BDL16_ORF_NR_XbaI - AATCTAGACAGAACCAAAACTCTCGTATTAAC | 959 |
| | | Rev External: BDL16_ORF_ER_XbaI - AATCTAGAGAAACTTTGAATGGACTATGTAGC | 960 |
| BDL17 | SacI, XbaI | synthetic product | 1043 |
| BDL18 | XbaI, SacI | Fwd Nested: BDL18_ORF_NF_XbaI - AATCTAGATACAATGGCGGATACACACC | 961 |
| | | Fwd External: BDL18_ORF_EF_XbaI - ATTCTAGAGCTTACAATGGCGGATACACA | 962 |
| | | Rev Nested: BDL18_ORF_NR_SacI - AGAGCTCGTGAAAACACATATCTACCGTTC | 963 |
| | | Rev External: BDL18_ORF_ER_SacI - AGAGCTCCTTGCGATCTTTCATGCTTAC | 964 |
| BDL19 | SacI | Fwd Nested: BDL19_gDNA_NF_SacI - AGAGCTCAGAGAGAGATAGGGCTTTGAGG | 965 |
| | | Fwd External: BDL19_gDNA_EF_SacI - AGAGCTCGAAGAAGAACACAAAACAGTAGAG | 966 |
| | | Rev: BDL19_gDNA_R1_SacI - AGAGCTCGTGATTATGAAAACAACAAGCG | 967 |
| BDL20a | SalI, XbaI | Fwd: BDL20a_ORF_F1_SalI - AAAGTCGACAGAGACAAAGAAGTTGGCCA | 968 |
| | | Rev Nested: BDL20a_ORF_NR_XbaI - TTTCTAGATGCAAGATTCAAATACGACTTAG | 969 |
| | | Rev External: BDL20a_ORF_ER_SacI - AGAGCTCGGACCATTTACCTTGATTTGTTAC | 970 |

TABLE 17-continued

Polynucleotides cloned from cDNA libraries, genomic DNA or synthetically produced and the primers used for the cloning

| Gene Name | Restriction Enzymes used for cloning | Primers used for amplification (5'→3') | SEQ ID NO: |
|---|---|---|---|
| BDL20b | SmaI + SacI | synthetic product | 1044 |
| BDL21 | SalI, XbaI | Fwd Nested: BDL21-ORF-NF-Sal - AATGTCGACAAGCATGTTTAAACTCTGTCTCG | 971 |
| | | Fwd External: BDL21-ORF-EF-Sal - TTAGTCGACGAAAGGAAAAGCATGTTTAAAC | 972 |
| | | Rev Nested: BDL21-ORF-NR-XbaI - CCGTCTAGAGGAAACTTTTAATTGTCATGTGA | 973 |
| | | Rev External: BDL21-ORF-ER-XbaI - GGCTCTAGATTTTCTAGTGAATTGTATCAATGG | 974 |
| BDL23 | XbaI, SacI | Fwd Nested: BDL23_ORF_NF_XbaI - AATCTAGACATCATAATCATATGGAGTTCGA | 975 |
| | | Fwd External: BDL23_ORF_EF_XbaI - AATCTAGAGATCTAGGGTTTCATGCTTCAC | 976 |
| | | Rev: BDL23_ORF_R1_SacI - AGAGCTCGTTCGACTTGTTTATATTGCACG | 977 |
| BDL24 | SmaI, SacI | synthetic product | 1045 |
| BDL25 | XbaI | Fwd Nested: BDL25_ORF_NF_XbaI - ATTCTAGACTCCGAGACTGTCTCCGATTG | 978 |
| | | Fwd External: BDL25_ORF_EF_XbaI - ATTCTAGACAATCACCGTGGACACCTC | 979 |
| | | Rev: BDL25_ORF_R_XbaI - ATTCTAGAGTGGCAACATCTGAAGTATTCC | 980 |
| BDL26a | SacI | Fwd Nested: BDL26a_ORF_NF_SacI - AGAGCTCTCATTACAGTGACTCTGCATGC | 981 |
| | | Fwd External: BDL26a_ORF_EF_SacI - AGAGCTCTCTTGTCTACTTTCATTACAGTGAC | 982 |
| | | Rev Nested: BDL26a + b_ORF_NR_SacI - TAGAGCTCGAAAGTACATAATGGACATGAGC | 983 |
| | | Rev External: BDL26a + b_ORF_ER_SacI - TAGAGCTCGATTTTTAAAGTAGTTATAGTGATGAA | 984 |
| BDL26b | SacI | Fwd Nested: BDL26b_ORF_NF_SacI - AGAGCTCGTAATATTACCATAAGGTTCAGAAG | 985 |
| | | Fwd External: BDL26b_ORF_EF_SacI - AGAGCTCCATAATTTTTTCGTATTTAACTCTT | 986 |
| | | Rev Nested: BDL26a + b_ORF_NR_SacI - TAGAGCTCGAAAGTACATAATGGACATGAGC | 987 |
| | | Rev external: BDL26a + b_ORF_ER_SacI - TAGAGCTCGATTTTTAAAGTAGTTATAGTGATGAA | 988 |
| BDL27 | XbaI, SacI | Fwd Nested: BDL27_ORF_NF_XbaI - AATCTAGACTCTTACACATGTATCGGTAGTTG | 989 |
| | | Fwd External: BDL27_ORF_EF_XbaI - AATCTAGACTTAAAACATTGGAAACAAGAATTC | 990 |
| | | Rev Nested: BDL27_ORF_NR_SacI - AGAGCTCGATCAGAAATACATGACGATAGATG | 991 |
| | | Rev External: BDL27_ORF_ER_SacI - AGAGCTCGCATCTTTGTTTTGGACGA | 992 |
| BDL28 | SalI, xbaI | Fwd Nested: BDL28_ORF_NF_SalI - AAAGTCGACGAGAGATGGCTAAATCAGATATG | 993 |
| | | Fwd External: BDL28_ORF_EF_SalI - AATGTCGACGAGAGTGAGAGATGGCTAAATCAG | 994 |
| | | Rev Nested: BDL28_ORF_NR_XbaI - ATTCTAGAAGAAGCAATCACCATTTTAAGG | 995 |
| | | Rev External: BDL28_ORF_ER_XbaI - ATTCTAGACCGAAAATCCAATTTAGTTGC | 996 |
| BDL29 | SalI, XbaI | Fwd Nested: BDL29_ORF_NF_SalI - AATGTCGACGATTTCTTCTCCTTAAGCCATG | 997 |
| | | Fwd External: BDL29_ORF_EF_SalI - AATGTCGACGGAGAGTTTTCTTTATTACTAGGG | 998 |
| | | Rev Nested: BDL29_ORF_NR_XbaI - AATCTAGACACACATCATTTCATAAGTGACC | 999 |
| | | Rev External: BDL29_ORF_ER_XbaI - AATCTAGACAACCATTATTACCGAAGAGC | 1000 |

TABLE 17-continued

Polynucleotides cloned from cDNA libraries, genomic DNA or synthetically produced and the primers used for the cloning

| Gene Name | Restriction Enzymes used for cloning | Primers used for amplification (5'→3') | SEQ ID NO: |
|---|---|---|---|
| BDL30 | SmaI, SacI | synthetic product | 1046 |
| BDL32a | XbaI, SacI | Fwd Nested: BDL32a_ORF_NF_XbaI - AATCTAGAGAGGATAATGCGTAACACACAAG | 1001 |
|  |  | Fwd External: BDL32a_ORF_EF_XbaI - AATCTAGAGATTTTATTCGAGGATAATGCG | 1002 |
|  |  | Rev Nested: BDL32a + b_ORF_NR_SacI - AGAGCTCCATTAAGACATCCGATTTATTTG | 1003 |
|  |  | Rev External: BDL32a + b_ORF_ER_SacI - AGAGCTCGAGACTTGTCACACACGTGAGG | 1004 |
| BDL32b | XbaI, SacI | Fwd nested: BDL32b_ORF_NF_XbaI - AATCTAGACACACACACAAACATAAGGAAA | 1005 |
|  |  | Fwd External: BDL32b_ORF_EF_XbaI - AATCTAGAAACAATACACACACACAAACATAAG | 1006 |
|  |  | Rev Nested: BDL32a + b_ORF_NR_SacI - AGAGCTCCATTAAGACATCCGATTTATTTG | 1007 |
|  |  | Rev External: BDL32a + b_ORF_ER_SacI - AGAGCTCGAGACTTGTCACACACGTGAGG | 1008 |
| Wrinkled1 | SalI, XbaI | Fwd nested: WRI_NF_ORF_SalI AATGTCGACCAGAGTTTAATGAAGAAGCGCT | 1009 |
|  |  | Fwd External: WRI_EF_Art_SalI - AATGTCGACAAATCTAAACTTTCTCAGAG | 1010 |
|  |  | Rev Nested: WRI_NR_ORF_XbaI AATCTAGACTCTCTCAGACCAAATAGTTACAAG | 1011 |
|  |  | Rev External: WRI_ER_Art_XbaI - AATCTAGAGGCAAAGACATTGATTATTC | 1012 |
| Napin | HindIII, SalI | Fwd: Napin F HindIII - ATAAGCTTATTGATTCCTTTAAAGACTTATGTT | 1013 |
|  |  | Rev: Napin R SalI - TCGTCGACGGGTGTATGTTTTAATCTTGTTT | 1014 |

To optimize the coding sequence (in silico design), codon-usage Tables calculated from plant transcriptoms were used (example of such Tables can be found in the Codon Usage Database available online at Hypertext Transfer Protocol://World Wide Web (dot) kazusa (dot) or (dot) jp/codon/). The optimized coding sequences were designed in a way that no changes are introduced in the encoded amino acid sequence (of selected polypeptides from Table 1, Example 1) while using codons preferred for expression in dicotyledonous plants mainly Arabidopsis, Canola and Soya; and mono-cotyledonous plants such as maize. Such optimized sequences promote better translation rate and therefore higher protein expression levels. To the optimized sequences flanking additional unique restriction enzymes sites were added—SalI, XbaI, BamHI, SmaI at the 5' end and SacI at the 3' end (except one gene—BDL-1, in which the SmaI site was excluded). The genes for which codon optimized synthetic (artificial) sequences were prepared are: BDL-1 (SEQ ID NO:1040), BDL-4 (SEQ ID NO:1041), BDL-11 (SEQ ID NO:1042), BDL-17 (SEQ ID NO:1043), BDL-20b (SEQ ID NO:1044), BDL-24 (SEQ ID NO:1045), BDL-30 (SEQ ID NO:1046). The artificial optimized polynucleotide sequences were synthesized by a commercial supplier [GeneArt, GmbH, (Hypertext Transfer Protocol://World Wide Web (dot) geneart (dot) com/)].

Generation of binary vectors comprising BDL genes and plant functional promoters for driving expression of same— The plasmid pPI was constructed by inserting a synthetic poly-(A) signal sequence, originating from pGL3 basic plasmid vector (Promega, Acc No U47295; by 4658-4811) into the HindIII restriction site of the binary vector pBI101.3 (Clontech, GenBank Accession. No. U12640). In some cases the backbone binary plasmid used was pGI which is similar to pPI but the GUS gene was replaced by the GUS-Intron gene (Vancanneyt. G, et al MGG 220, 245-50, 1990). pGI was used to clone part of the polynucleotide sequences, initially under the control of 35S promoter [Odell, J T, et al. Nature 313, 810-812 (28 Feb. 1985); SEQ ID NO:921]. Additional sequences were cloned into pMBLArt under the control of 35S promoter.

Some polynucleotide sequences were cloned under other preferential promoter as described below. The promoter, named Napin originated from Brassica napus which is characterized by a seed specific promoter activity [Stuitje A. R. et. al. Plant Biotechnology Journal 1 (4): 301-309], was amplified by direct PCR on genomic DNA extracted from leaf tissue using the DNAeasy kit (Qiagen Cat. No. 69104) using the following primers:

(SEQ ID NO: 1013)
Napin F Hind III (Enzyme HindII)- 5'-ATAAGCTTATTGATTCCTTTAAAGACTTATGTT (SEQ ID NO: 1014)
Napin R Sal I (Enzyne Sal I)- 5'-TCGTCGACGGGTGTATGTTTTAATCTTGTTT.

The following genes were cloned downstream of the Napin promoter sequence: BDL-2, BDL-3, BDL-4, BDL-6, BDL-12, BDL-14, BDL-15, BDL-17, BDL-18, BDL-21, BDL-23, BDL-25, BDL-27, BDL-28, BDL-29, BDL-32b, Wrinkle1. For control purposes, the β-glucuronidase enzyme (GUS, SEQ ID NO:1051) encoded by the uid A gene (GUS-Intron, SEQ ID NO:1049).

Example 4

Producing Transgenic *Arabidopsis* Plants Expressing the Seed Oil Genes

Materials And Methods

Plant transformation was performed according to (Clough S J, Bent A F. 1998. Floral dip: a simplified method for *Agrobacterium*-mediated transformation of *Arabidopsis thaliana*. Plant J. 16(6): 735-43, Desfeux C, Clough S J, Bent A F. 2000. Female reproductive tissues are the primary targets of *Agrobacterium*-mediated transformation by the *Arabidopsis* floral-dip method. Plant Physiol. 123(3): 895-904.).

The *Arabidopsis thaliana* var *Columbia* ($T_0$ plants) were transformed according to the Floral Dip procedure described by Clough S J, Bent A F. (1998) Floral dip: a simplified method for *Agrobacterium*-mediated transformation of *Arabidopsis thaliana*. Plant J. 16(6): 735-43; and Desfeux C, Clough S J, Bent A F. (20000 Female reproductive tissues are the primary targets of *Agrobacterium*-mediated transformation by the *Arabidopsis* floral-dip method. Plant Physiol. 123(3): 895-904) with minor modifications. Briefly, *Arabidopsis thaliana* Columbia (Co10) $T_0$ Plants were sown in 250 ml pots filled with wet peat-based growth mix. The pots were covered with aluminum foil and a plastic dome, kept at 4° C. for 3-4 days, then uncovered and incubated in a growth chamber at 18-24° C. under 16/8 hours light/dark cycles. The $T_0$ plants were ready for transformation six days before anthesis.

Single colonies of *Agrobacterium* carrying the binary vectors harboring the seed oil genes were cultured in LB medium supplemented with kanamycin (50 mg/L) and gentamycin (50 mg/L). The cultures were incubated at 28° C. for 48 hours under vigorous shaking and centrifuged at 4000 rpm for 5 minutes. The pellets comprising *Agrobacterium* cells were resuspended in a transformation medium which contained half-strength (2.15 g/L) Murashige-Skoog (Duchefa); 0.044 µM benzylamino purine (Sigma); 112 µg/L B5 Gambourg vitamins (Sigma); 5% sucrose; and 0.2 ml/L Silwet L-77 (OSI Specialists, CT) in double-distilled water, at pH of 5.7.

Transformation of $T_0$ plants was performed by inverting each plant into an *Agrobacterium* suspension such that the above ground plant tissue was submerged for 3-5 seconds. Each inoculated $T_0$ plant was immediately placed in a plastic tray, then covered with clear plastic dome to maintain humidity and kept in the dark at room temperature for 18 hours to facilitate infection and transformation. Transformed (transgenic) plants were then uncovered and transferred to a greenhouse for recovery and maturation. The transgenic $T_0$ plants were grown in the greenhouse for 3-5 weeks until siliques were brown and dry, then seeds were harvested from plants and kept at room temperature until sowing For generating $T_1$ and $T_2$ transgenic plants harboring the genes, seeds collected from transgenic $T_0$ plants were surface-sterilized by soaking in 70% ethanol for 1 minute, followed by soaking in 5% sodium hypochlorite and 0.05% triton for 5 minutes. The surface-sterilized seeds were thoroughly washed in sterile distilled water then placed on culture plates containing half-strength Murashig-Skoog (Duchefa); 2% sucrose; 0.8% plant agar; 50 mM kanamycin; and 200 mM carbenicylin (Duchefa). The culture plates were incubated at 4° C. for 48 hours then transferred to a growth room at 25° C. for an additional week of incubation. Vital $T_1$ *Arabidopsis* plants were transferred to a fresh culture plates for another week of incubation. Following incubation the $T_1$ plants were removed from culture plates and planted in growth mix contained in 250 ml pots. The transgenic plants were allowed to grow in a greenhouse to maturity. Seeds harvested from $T_1$ plants were cultured and grown to maturity as $T_2$ plants under the same conditions as used for culturing and growing the $T_1$ plants.

Example 5

Identification of Additional Sequences with Highest Probability to Confer Similar Favorable Effects in the Transgenic Plants Methods for the search and identification of homologues of seed yield polypeptide or polynucleotide would be well within the realm of a person skilled in the art. The search and identification of homologous genes involves the screening of sequence information available, for example, in public databases, that include but are not limited to the DNA Database of Japan (DDBJ), Genbank, and the European Molecular Biology Laboratory Nucleic Acid Sequence Database (EMBL) or versions thereof or the MIPS database. A number of different search algorithms have been developed, including but not limited to the suite of programs referred to as BLAST programs. There are five implementations of BLAST, three designed for nucleotide sequence queries (BLASTN, BLASTX, and TBLASTX) and two designed for protein sequence queries (BLASTP and TBLASTN) (Coulson, Trends in Biotechnology: 76-80, 1994; Birren et al., Genome Analysis, I: 543, 1997). Such methods involve alignment and comparison of sequences. The BLAST algorithm calculates percent sequence identity and performs a statistical analysis of the similarity between the two sequences. The software for performing BLAST analysis is publicly available through the National Centre for Biotechnology Information. Other such software or algorithms are GAP, BESTFIT, FASTA and TFASTA. GAP uses the algorithm of Needleman and Wunsch (J. Mol. Biol. 48: 443-453, 1970) to find the alignment of two complete sequences that maximizes the number of matches and minimizes the number of gaps.

The homologous genes may belong to the same gene family. The analysis of a gene family may be carried out using sequence similarity analysis. To perform this analysis one may use standard programs for multiple alignments e.g. Clustal W. A neighbour-joining tree of the proteins homologous to the genes in this invention may be used to provide an overview of structural and ancestral relationships. Sequence identity may be calculated using an alignment program as described above. It is expected that other plants will carry a similar functional gene (orthologue) or a family of similar genes and those genes will provide the same preferred phenotype as the genes presented here. Advantageously, these family members may be useful in the methods of the invention. Example of other plants are included here but not limited to, barley (*Hordeum vulgare*), *Arabidopsis* (*Arabidopsis thaliana*), maize (*Zea mays*), cotton (*Gossypium*), Oilseed rape (*Brassica napus*), Rice (*Oryza sativa*), Sugar cane (*Saccharum officinarum*), Sorghum (*Sorghum* bicolor), Soybean (*Glycine max*), Sunflower (*Helianthus annuus*), Tomato (*Lycopersicon esculentum*), Wheat (*Triticum aestivum*)

The above-mentioned analyses for sequence homology is preferably carried out on a full-length sequence, but may also be based on a comparison of certain regions such as conserved domains. The identification of such domains, would also be well within the realm of the person skilled in the art and would involve, for example, a computer readable format of the nucleic acids of the present invention, the use of alignment software programs and the use of publicly available information on protein domains, conserved motifs and boxes. This information is available in the PRODOM (Hypertext Transfer Protocol://World Wide Web (dot) biochem (dot) ucl (dot) ac (dot) uk/bsm/dbbrowser/protocol/prodomqry (dot) html), PIR (Hypertext Transfer Protocol:// pir (dot) Georgetown (dot) edu/) or Pfam (Hypertext Transfer Protocol://World Wide Web (dot) sanger (dot) ac (dot) uk/Software/Pfam/) database. Sequence analysis programs designed for motif searching may be used for identification of fragments, regions and conserved domains as mentioned above. Preferred computer programs include, but are not limited to, MEME, SIGNALSCAN, and GENESCAN.

A person skilled in the art may use the homologous sequences provided herein to find similar sequences in other species and other organisms. Homologues of a protein encompass, peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (conservative changes, such as similar hydrophobicity, hydrophilicity, antigenicity, propensity to form or break a-helical structures or 3-sheet structures). Conservative substitution tables are well known in the art (see for example Creighton (1984) Proteins. W.H. Freeman and Company). Homologues of a nucleic acid encompass nucleic acids having nucleotide substitutions, deletions and/or insertions relative to the unmodified nucleic acid in question and having similar biological and functional activity as the unmodified nucleic acid from which they are derived.

Genes identified in publicly available sequence databases as sharing high sequence homology to the *arabidopsis* genes identified herein are summarized in Table 18 below. Those genes are expected to possess similar functions when exogenously introduced into plants, as the *arabidopsis* genes identified. Homolog genes sequences are also provided.

TABLE 18

Polypeptides and polynucleotides encoding same which share high sequence homology to the identified arabidopsis polypeptides of the invention

| | Polynucleotide SEQ_ID_NO: | Polypeptide SEQ_ID_NO: | Organism | Homology to SEQ_ID_NO: | % identity | % query coverage | Algorithm |
|---|---|---|---|---|---|---|---|
| 1 | 369 | 523 | peanut | 51 | 83 | 48.4 | tblastx |
| 2 | 370 | | oil_palm | 126 | 78 | 19.0 | tblastx |
| 3 | 371 | 524 | tobacco | 51 | 88 | 45.1 | tblastx |
| 4 | 372 | 525 | tobacco | 18 | 85 | 22.0 | tblastx |
| 5 | 373 | 526 | tobacco | 165 | 85 | 13.2 | tblastx |
| 6 | 374 | 527 | tobacco | 165 | 77 | 14.7 | tblastx |
| 7 | 375 | 528 | barley | 51 | 85 | 45.1 | tblastx |
| 8 | 376 | 529 | barley | 117 | 85 | 27.6 | tblastx |
| 9 | 377 | 530 | barley | 126 | 85 | 31.5 | tblastx |
| 10 | 378 | 531 | barley | 137 | 92 | 25.4 | tblastx |
| 11 | 379 | 532 | barley | 150 | 65 | 41.0 | tblastx |
| 12 | 380 | 533 | peach | 51 | 90 | 46.4 | tblastx |
| 13 | 381 | | *thellungiella* | 42 | 86 | 18.9 | tblastx |
| 14 | 382 | | *thellungiella* | 61 | 88 | 13.1 | tblastx |
| 15 | 383 | 534 | *thellungiella* | 66 | 91 | 14.7 | tblastx |
| 16 | 384 | | *thellungiella* | 70 | 86 | 20.5 | tblastx |
| 17 | 385 | 535 | *thellungiella* | 18 | 95 | 26.4 | tblastx |
| 18 | 386 | 536 | *thellungiella* | 163 | 92 | 27.7 | tblastx |
| 19 | 387 | 537 | strawberry | 51 | 83 | 47.1 | tblastx |
| 20 | 388 | 538 | canola | 36 | 90 | 28.5 | tblastx |
| 21 | 389 | | canola | 36 | 88 | 17.0 | tblastx |
| 22 | 390 | 539 | canola | 9 | 89 | 64.7 | tblastx |
| 23 | 391 | 540 | canola | 29 | 88 | 49.9 | tblastx |
| 24 | 392 | 541 | canola | 40 | 87 | 82.0 | tblastx |
| 25 | 393 | 542 | canola | 40 | 87 | 79.4 | tblastx |
| 26 | 394 | 543 | canola | 40 | 87 | 82.0 | tblastx |
| 27 | 395 | | canola | 40 | 86 | 46.5 | tblastx |
| 28 | 396 | 544 | canola | 41 | 95 | 36.5 | tblastx |
| 29 | 397 | 545 | canola | 41 | 93 | 36.5 | tblastx |
| 30 | 398 | 546 | canola | 44 | 87 | 41.1 | tblastx |
| 31 | 399 | 547 | canola | 51 | 93 | 49.0 | tblastx |
| 32 | 400 | 548 | canola | 51 | 97 | 51.0 | tblastx |
| 33 | 401 | 549 | canola | 51 | 77 | 64.7 | tblastx |
| 34 | 402 | 550 | canola | 54 | 94 | 22.3 | tblastx |
| 35 | 403 | 551 | canola | 55 | 93 | 59.3 | tblastx |
| 36 | 404 | | canola | 56 | 85 | 26.0 | tblastx |
| 37 | 405 | 552 | canola | 57 | 94 | 19.1 | tblastx |
| 38 | 406 | 553 | canola | 60 | 90 | 23.6 | tblastx |
| 39 | 407 | 554 | canola | 61 | 88 | 27.7 | tblastx |
| 40 | 408 | 555 | canola | 63 | 92 | 47.5 | tblastx |
| 41 | 409 | 556 | canola | 10 | 87 | 49.7 | tblastx |
| 42 | 410 | 557 | canola | 66 | 91 | 24.9 | tblastx |

TABLE 18-continued

Polypeptides and polynucleotides encoding same which share high sequence homology to the identified arabidopsis polypeptides of the invention

| Polynucleotide SEQ_ID_NO: | Polypeptide SEQ_ID_NO: | Organism | Homology to SEQ_ID_NO: | % identity | % query coverage | Algorithm |
|---|---|---|---|---|---|---|
| 43 | 411 |  | canola | 7 | 87 | 31.6 | tblastx |
| 44 | 412 |  | canola | 14 | 92 | 44.1 | tblastx |
| 45 | 413 |  | canola | 14 | 92 | 44.1 | tblastx |
| 46 | 414 |  | canola | 81 | 85 | 36.3 | tblastx |
| 47 | 415 | 558 | canola | 35 | 90 | 32.4 | tblastx |
| 48 | 416 | 559 | canola | 35 | 88 | 45.3 | tblastx |
| 49 | 417 | 560 | canola | 35 | 91 | 45.3 | tblastx |
| 50 | 418 | 561 | canola | 91 | 88 | 28.9 | tblastx |
| 51 | 419 | 562 | canola | 93 | 95 | 14.5 | tblastx |
| 52 | 420 |  | canola | 101 | 95 | 11.3 | tblastx |
| 53 | 421 | 563 | canola | 106 | 84 | 32.1 | tblastx |
| 54 | 422 |  | canola | 107 | 83 | 62.3 | tblastx |
| 55 | 423 | 564 | canola | 108 | 94 | 14.4 | tblastx |
| 56 | 424 | 565 | canola | 118 | 90 | 20.6 | tblastx |
| 57 | 425 | 566 | canola | 118 | 95 | 34.4 | tblastx |
| 58 | 426 | 567 | canola | 118 | 95 | 34.4 | tblastx |
| 59 | 427 | 568 | canola | 119 | 83 | 57.2 | tblastx |
| 60 | 428 |  | canola | 125 | 84 | 28.1 | tblastx |
| 61 | 429 |  | canola | 135 | 96 | 24.6 | tblastx |
| 62 | 430 | 569 | canola | 137 | 90 | 32.7 | tblastx |
| 63 | 431 |  | canola | 18 | 93 | 33.4 | tblastx |
| 64 | 432 | 570 | canola | 21 | 84 | 83.9 | tblastx |
| 65 | 433 |  | canola | 140 | 92 | 52.2 | tblastx |
| 66 | 434 | 571 | canola | 143 | 92 | 41.7 | tblastx |
| 67 | 435 | 572 | canola | 143 | 93 | 41.0 | tblastx |
| 68 | 436 | 573 | canola | 145 | 89 | 49.1 | tblastx |
| 69 | 437 | 574 | canola | 145 | 91 | 39.8 | tblastx |
| 70 | 438 |  | canola | 153 | 94 | 26.4 | tblastx |
| 71 | 439 | 575 | canola | 160 | 89 | 79.6 | tblastx |
| 72 | 440 | 576 | canola | 163 | 91 | 27.7 | tblastx |
| 73 | 441 | 577 | canola | 164 | 80 | 76.6 | tblastx |
| 74 | 442 | 578 | canola | 165 | 85 | 11.9 | tblastx |
| 75 | 443 | 579 | melon | 51 | 84 | 47.1 | tblastx |
| 76 | 444 | 580 | sugarcane | 137 | 90 | 25.7 | tblastx |
| 77 | 445 | 581 | sugarcane | 137 | 88 | 28.4 | tblastx |
| 78 | 446 | 582 | b_rapa | 41 | 95 | 36.1 | tblastx |
| 79 | 447 | 583 | b_rapa | 57 | 92 | 9.5 | tblastx |
| 80 | 448 |  | b_rapa | 64 | 86 | 45.7 | tblastx |
| 81 | 449 | 584 | b_rapa | 10 | 84 | 39.0 | tblastx |
| 82 | 450 |  | b_rapa | 4 | 86 | 40.5 | tblastx |
| 83 | 451 | 585 | b_rapa | 35 | 86 | 17.2 | tblastx |
| 84 | 452 | 586 | b_rapa | 106 | 78 | 36.8 | tblastx |
| 85 | 453 | 587 | b_rapa | 122 | 94 | 71.4 | tblastx |
| 86 | 454 | 588 | b_rapa | 126 | 87 | 32.6 | tblastx |
| 87 | 455 | 589 | b_rapa | 135 | 86 | 41.7 | tblastx |
| 88 | 456 | 590 | b_rapa | 137 | 85 | 17.8 | tblastx |
| 89 | 457 | 591 | b_rapa | 18 | 94 | 26.0 | tblastx |
| 90 | 458 | 592 | b_rapa | 150 | 82 | 42.9 | tblastx |
| 91 | 459 |  | b_rapa | 152 | 88 | 32.6 | tblastx |
| 92 | 460 | 593 | b_rapa | 165 | 85 | 11.9 | tblastx |
| 93 | 461 | 594 | maize | 137 | 86 | 24.1 | tblastx |
| 94 | 462 | 595 | maize | 137 | 89 | 14.0 | tblastx |
| 95 | 463 | 596 | maize | 137 | 86 | 24.1 | tblastx |
| 96 | 464 | 597 | maize | 165 | 72 | 15.5 | tblastx |
| 97 | 465 | 598 | almond | 18 | 89 | 20.8 | tblastx |
| 98 | 466 | 599 | *sorghum* | 123 | 87 | 20.6 | tblastx |
| 99 | 466 | 599 | *sorghum* | 124 | 87 | 20.5 | tblastx |
| 100 | 467 | 600 | *sorghum* | 123 | 89 | 19.8 | tblastx |
| 101 | 467 | 600 | *sorghum* | 124 | 89 | 19.6 | tblastx |
| 102 | 468 | 601 | *sorghum* | 137 | 85 | 12.6 | tblastx |
| 103 | 469 |  | soybean | 126 | 97 | 22.4 | tblastx |
| 104 | 470 | 602 | soybean | 137 | 92 | 20.1 | tblastx |
| 105 | 471 | 603 | soybean | 137 | 92 | 11.2 | tblastx |
| 106 | 472 | 604 | soybean | 137 | 92 | 20.1 | tblastx |
| 107 | 473 | 605 | soybean | 137 | 85 | 13.1 | tblastx |
| 108 | 474 | 606 | soybean | 137 | 87 | 17.0 | tblastx |
| 109 | 475 | 607 | soybean | 137 | 92 | 11.2 | tblastx |
| 110 | 476 | 608 | soybean | 137 | 85 | 32.3 | tblastx |
| 111 | 477 | 609 | soybean | 18 | 85 | 28.0 | tblastx |
| 112 | 478 | 610 | soybean | 18 | 86 | 28.0 | tblastx |
| 113 | 479 | 611 | soybean | 150 | 86 | 52.8 | tblastx |
| 114 | 480 | 612 | soybean | 150 | 86 | 52.8 | tblastx |
| 115 | 481 | 613 | soybean | 150 | 86 | 52.8 | tblastx |
| 116 | 482 | 614 | rice | 137 | 92 | 23.6 | tblastx |

TABLE 18-continued

Polypeptides and polynucleotides encoding same which share high sequence homology to the identified arabidopsis polypeptides of the invention

| Polynucleotide SEQ_ID_NO: | Polypeptide SEQ_ID_NO: | Organism | Homology to SEQ_ID_NO: | % identity | % query coverage | Algorithm |
|---|---|---|---|---|---|---|
| 117 | 483 | 615 | rice | 137 | 93 | 20.6 | tblastx |
| 118 | 484 | 616 | rice | 137 | 95 | 23.6 | tblastx |
| 119 | 485 | 617 | sunflower | 150 | 83 | 44.0 | tblastx |
| 120 | 486 | | sunflower | 161 | 90 | 7.8 | tblastx |
| 121 | 487 | 618 | poplar | 51 | 85 | 45.1 | tblastx |
| 122 | 488 | 619 | poplar | 123 | 89 | 22.6 | tblastx |
| 123 | 488 | 619 | poplar | 124 | 89 | 22.5 | tblastx |
| 124 | 489 | 620 | poplar | 137 | 87 | 8.3 | tblastx |
| 125 | 490 | 621 | poplar | 18 | 86 | 15.8 | tblastx |
| 126 | 491 | 622 | poplar | 165 | 85 | 13.2 | tblastx |
| 127 | 492 | | b_oleracea | 29 | 92 | 23.3 | tblastx |
| 128 | 493 | | b_oleracea | 50 | 90 | 20.7 | tblastx |
| 129 | 494 | 623 | b_oleracea | 51 | 93 | 51.6 | tblastx |
| 130 | 495 | 624 | b_oleracea | 55 | 91 | 43.7 | tblastx |
| 131 | 496 | | b_oleracea | 107 | 84 | 62.3 | tblastx |
| 132 | 497 | 625 | b_oleracea | 126 | 88 | 32.6 | tblastx |
| 133 | 498 | 626 | b_oleracea | 136 | 85 | 45.0 | tblastx |
| 134 | 499 | 627 | b_oleracea | 136 | 87 | 75.3 | tblastx |
| 135 | 500 | 628 | grape | 51 | 87 | 46.4 | tblastx |
| 136 | 501 | | grape | 4 | 84 | 23.5 | tblastx |
| 137 | 502 | 629 | grape | 143 | 90 | 21.9 | tblastx |
| 138 | 503 | 630 | grape | 150 | 93 | 21.4 | tblastx |
| 139 | 504 | 631 | grape | 150 | 84 | 39.5 | tblastx |
| 140 | 505 | 632 | wheat | 123 | 92 | 14.9 | tblastx |
| 141 | 505 | 632 | wheat | 124 | 92 | 14.8 | tblastx |
| 142 | 506 | 633 | wheat | 126 | 82 | 32.9 | tblastx |
| 143 | 507 | 634 | wheat | 126 | 87 | 28.0 | tblastx |
| 144 | 508 | 635 | wheat | 126 | 83 | 32.1 | tblastx |
| 145 | 509 | 636 | wheat | 137 | 91 | 24.1 | tblastx |
| 146 | 510 | 637 | wheat | 137 | 89 | 32.3 | tblastx |
| 147 | 511 | 638 | wheat | 137 | 95 | 11.2 | tblastx |
| 148 | 512 | 639 | wheat | 150 | 73 | 53.9 | tblastx |
| 149 | 513 | 640 | wheat | 161 | 86 | 8.8 | tblastx |
| 150 | 514 | 641 | wheat | 161 | 88 | 7.8 | tblastx |
| 151 | 515 | 642 | wheat | 161 | 92 | 7.2 | tblastx |
| 152 | 516 | 643 | flax | 18 | 74 | 15.3 | tblastx |
| 153 | 517 | 644 | tomato | 51 | 85 | 45.8 | tblastx |
| 154 | 518 | 645 | tomato | 123 | 92 | 15.9 | tblastx |
| 155 | 518 | 645 | tomato | 124 | 92 | 15.8 | tblastx |
| 156 | 519 | 646 | tomato | 126 | 94 | 25.1 | tblastx |
| 157 | 520 | 647 | cotton | 51 | 87 | 45.8 | tblastx |
| 158 | 521 | 648 | cotton | 51 | 88 | 46.4 | tblastx |
| 159 | 522 | 649 | cotton | 123 | 91 | 18.8 | tblastx |
| 160 | 522 | 649 | cotton | 124 | 91 | 18.7 | tblastx |
| 161 | 650 | 786 | b_rapa | 169 | 88 | 73.7 | blastp |
| 162 | 651 | 787 | canola | 169 | 93 | 62.6 | blastp |
| 163 | 652 | 788 | radish | 169 | 88 | 77.1 | blastp |
| 164 | 653 | 789 | b_oleracea | 174 | 93 | 55.7 | blastp |
| 165 | 654 | 790 | b_rapa | 179 | 94 | 70.4 | blastp |
| 166 | 655 | 791 | canola | 179 | 88 | 100.0 | blastp |
| 167 | 656 | 792 | canola | 183 | 85 | 84.9 | blastp |
| 168 | 657 | 793 | canola | 186 | 89 | 96.8 | blastp |
| 169 | 658 | 794 | canola | 191 | 89 | 51.4 | blastp |
| 170 | 659 | 795 | b_oleracea | 192 | 88 | 56.4 | blastp |
| 171 | 660 | 796 | canola | 194 | 85 | 96.0 | blastp |
| 172 | 661 | 797 | b_rapa | 195 | 90 | 100.0 | blastp |
| 173 | 662 | 798 | canola | 195 | 91 | 100.0 | blastp |
| 174 | 663 | 799 | canola | 200 | 90 | 94.7 | blastp |
| 175 | 664 | 800 | canola | 200 | 90 | 98.9 | blastp |
| 176 | 665 | 801 | b_oleracea | 205 | 87 | 100.0 | blastp |
| 177 | 666 | 802 | b_rapa | 205 | 87 | 69.1 | blastp |
| 178 | 667 | 803 | b_rapa | 205 | 86 | 73.5 | blastp |
| 179 | 668 | 804 | canola | 205 | 86 | 61.4 | blastp |
| 180 | 669 | 805 | radish | 205 | 87 | 76.5 | blastp |
| 181 | 670 | 806 | canola | 206 | 93 | 100.0 | blastp |
| 182 | 671 | 807 | radish | 206 | 93 | 100.0 | blastp |
| 183 | 672 | 808 | b_oleracea | 209 | 87 | 52.6 | blastp |
| 184 | 673 | 809 | b_rapa | 209 | 86 | 51.9 | blastp |
| 185 | 674 | 810 | canola | 209 | 88 | 100.0 | blastp |
| 186 | 675 | 811 | apple | 216 | 89 | 100.0 | blastp |
| 187 | 676 | 812 | apple | 216 | 89 | 100.0 | blastp |
| 188 | 677 | 813 | avocado | 216 | 85 | 100.0 | blastp |
| 189 | 678 | 814 | b_juncea | 216 | 97 | 69.1 | blastp |
| 190 | 679 | 815 | b_juncea | 216 | 98 | 91.2 | blastp |

TABLE 18-continued

Polypeptides and polynucleotides encoding same which share high sequence homology to the identified arabidopsis polypeptides of the invention

| Polynucleotide SEQ_ID_NO: | Polypeptide SEQ_ID_NO: | Organism | Homology to SEQ_ID_NO: | % identity | % query coverage | Algorithm |
|---|---|---|---|---|---|---|
| 191 | 680 | 816 | b_juncea | 216 | 97 | 100.0 | blastp |
| 192 | 681 | 817 | b_rapa | 216 | 97 | 100.0 | blastp |
| 193 | 682 | 818 | bean | 216 | 88 | 100.0 | blastp |
| 194 | 683 | 819 | brachypodium | 216 | 85 | 100.0 | blastp |
| 195 | 684 | 820 | cassava | 216 | 91 | 100.0 | blastp |
| 196 | 685 | 821 | cassava | 216 | 86 | 100.0 | blastp |
| 197 | 686 | 822 | castorbean | 216 | 88 | 100.0 | blastp |
| 198 | 687 | 823 | centaurea | 216 | 86 | 100.0 | blastp |
| 199 | 688 | 824 | centaurea | 216 | 86 | 100.0 | blastp |
| 200 | 689 | 825 | citrus | 216 | 89 | 100.0 | blastp |
| 201 | 690 | 826 | citrus | 216 | 89 | 100.0 | blastp |
| 202 | 691 | 827 | coffea | 216 | 85 | 100.0 | blastp |
| 203 | 692 | 828 | cotton | 216 | 88 | 100.0 | blastp |
| 204 | 693 | 829 | iceplant | 216 | 86 | 100.0 | blastp |
| 205 | 694 | 830 | ipomoea | 216 | 88 | 100.0 | blastp |
| 206 | 695 | 831 | lettuce | 216 | 85 | 100.0 | blastp |
| 207 | 696 | 832 | lettuce | 216 | 85 | 100.0 | blastp |
| 208 | 697 | 833 | lettuce | 216 | 85 | 100.0 | blastp |
| 209 | 698 | 834 | lettuce | 216 | 85 | 100.0 | blastp |
| 210 | 699 | 835 | lotus | 216 | 89 | 100.0 | blastp |
| 211 | 700 | 836 | medicago | 216 | 88 | 100.0 | blastp |
| 212 | 701 | 837 | pepper | 216 | 86 | 100.0 | blastp |
| 213 | 702 | 838 | periwinkle | 216 | 88 | 100.0 | blastp |
| 214 | 703 | 839 | petunia | 216 | 88 | 100.0 | blastp |
| 215 | 704 | 840 | potato | 216 | 86 | 97.1 | blastp |
| 216 | 705 | 841 | radish | 216 | 95 | 100.0 | blastp |
| 217 | 706 | 842 | radish | 216 | 95 | 100.0 | blastp |
| 218 | 707 | 843 | radish | 216 | 97 | 100.0 | blastp |
| 219 | 708 | 844 | rose | 216 | 85 | 100.0 | blastp |
| 220 | 709 | 845 | safflower | 216 | 85 | 100.0 | blastp |
| 221 | 710 | 846 | safflower | 216 | 85 | 100.0 | blastp |
| 222 | 711 | 847 | safflower | 216 | 86 | 100.0 | blastp |
| 223 | 712 | 848 | soybean | 216 | 91 | 100.0 | blastp |
| 224 | 713 | 849 | soybean | 216 | 91 | 100.0 | blastp |
| 225 | 714 | 850 | spurge | 216 | 89 | 97.1 | blastp |
| 226 | 715 | 851 | strawberry | 216 | 86 | 100.0 | blastp |
| 227 | 716 | | thellungiella | 216 | 90 | 92.6 | tblastn |
| 228 | 717 | 852 | tobacco | 216 | 88 | 100.0 | blastp |
| 229 | 718 | 853 | radish | 219 | 87 | 100.0 | blastp |
| 230 | 719 | 854 | radish | 219 | 92 | 54.8 | blastp |
| 231 | 720 | 855 | b_oleracea | 220 | 93 | 70.8 | blastp |
| 232 | 721 | 856 | b_rapa | 220 | 93 | 99.1 | blastp |
| 233 | 722 | 857 | canola | 220 | 93 | 81.5 | blastp |
| 234 | 723 | 858 | radish | 220 | 93 | 99.1 | blastp |
| 235 | 724 | 859 | radish | 220 | 93 | 99.4 | blastp |
| 236 | 725 | 860 | arabidopsis | 244 | 96 | 99.6 | blastp |
| 237 | 726 | 861 | arabidopsis | 244 | 96 | 99.3 | tblastn |
| 238 | 727 | 862 | b_rapa | 246 | 86 | 52.1 | blastp |
| 239 | 728 | 863 | canola | 246 | 85 | 53.4 | blastp |
| 240 | 729 | 864 | canola | 258 | 87 | 100.0 | blastp |
| 241 | 730 | 865 | canola | 266 | 86 | 51.5 | blastp |
| 242 | 731 | 866 | b_oleracea | 272 | 85 | 97.1 | blastp |
| 243 | 732 | 867 | canola | 272 | 85 | 97.1 | blastp |
| 244 | 733 | 868 | arabidopsis | 273 | 87 | 99.0 | blastp |
| 245 | 734 | 869 | b_rapa | 273 | 94 | 81.1 | blastp |
| 246 | 735 | 870 | b_rapa | 273 | 88 | 60.8 | blastp |
| 247 | 736 | 871 | b_rapa | 273 | 94 | 65.2 | blastp |
| 248 | 737 | 872 | radish | 273 | 89 | 75.4 | blastp |
| 249 | 738 | 873 | b_rapa | 274 | 86 | 81.0 | blastp |
| 250 | 739 | 874 | canola | 274 | 90 | 100.0 | blastp |
| 251 | 740 | 875 | arabidopsis | 277 | 85 | 57.7 | blastp |
| 252 | 741 | 876 | canola | 277 | 90 | 92.8 | blastp |
| 253 | 742 | 877 | radish | 277 | 88 | 99.1 | blastp |
| 254 | 743 | 878 | b_oleracea | 282 | 87 | 75.2 | blastp |
| 255 | 744 | 879 | b_rapa | 283 | 94 | 74.6 | blastp |
| 256 | 745 | 880 | basilicum | 283 | 85 | 51.7 | blastp |
| 257 | 746 | 881 | canola | 283 | 90 | 58.1 | blastp |
| 258 | 747 | 882 | canola | 284 | 85 | 100.0 | blastp |
| 259 | 748 | 883 | arabidopsis | 286 | 88 | 54.1 | blastp |
| 260 | 749 | 884 | arabidopsis | 286 | 86 | 98.2 | blastp |
| 261 | 750 | 885 | b_rapa | 286 | 85 | 59.2 | blastp |
| 262 | 751 | 886 | radish | 287 | 91 | 100.0 | blastp |
| 263 | 752 | 887 | thellungiella | 287 | 93 | 94.7 | blastp |
| 264 | 753 | 888 | canola | 288 | 92 | 60.4 | blastp |

TABLE 18-continued

Polypeptides and polynucleotides encoding same which share high sequence homology to the identified arabidopsis polypeptides of the invention

| Polynucleotide SEQ_ID_NO: | Polypeptide SEQ_ID_NO: | Organism | Homology to SEQ_ID_NO: | % identity | % query coverage | Algorithm |
|---|---|---|---|---|---|---|
| 265 | 754 | 889 | b_oleracea | 297 | 86 | 96.1 | blastp |
| 266 | 755 | 890 | canola | 297 | 85 | 96.1 | blastp |
| 267 | 756 | 891 | canola | 297 | 86 | 96.1 | blastp |
| 268 | 757 | 892 | b_oleracea | 299 | 85 | 53.2 | blastp |
| 269 | 758 | 893 | canola | 299 | 85 | 100.0 | blastp |
| 270 | 759 | 894 | canola | 299 | 85 | 58.2 | blastp |
| 271 | 760 | 895 | canola | 300 | 94 | 51.9 | blastp |
| 272 | 761 | 896 | b_rapa | 301 | 85 | 98.1 | blastp |
| 273 | 762 | 897 | radish | 301 | 86 | 99.4 | blastp |
| 274 | 763 | 898 | b_rapa | 302 | 85 | 100.0 | blastp |
| 275 | 764 | 899 | canola | 305 | 92 | 87.5 | blastp |
| 276 | 765 | 900 | canola | 305 | 92 | 94.8 | blastp |
| 277 | 766 | 901 | radish | 305 | 92 | 100.0 | blastp |
| 278 | 767 | 902 | b_rapa | 308 | 91 | 62.4 | blastp |
| 279 | 768 | 903 | radish | 308 | 91 | 51.4 | blastp |
| 280 | 769 | 904 | b_rapa | 310 | 94 | 89.1 | blastp |
| 281 | 770 | 905 | canola | 310 | 93 | 99.4 | blastp |
| 282 | 771 | 906 | radish | 310 | 92 | 99.7 | blastp |
| 283 | 772 | 907 | arabidopsis | 313 | 91 | 99.8 | blastp |
| 284 | 773 | 908 | b_oleracea | 317 | 93 | 63.9 | blastp |
| 285 | 774 | 909 | canola | 317 | 85 | 100.0 | blastp |
| 286 | 775 | 910 | arabidopsis | 318 | 85 | 99.9 | blastp |
| 287 | 776 | 911 | canola | 328 | 85 | 100.0 | blastp |
| 288 | 777 | 912 | b_oleracea | 329 | 93 | 100.0 | blastp |
| 289 | 778 | 913 | b_rapa | 329 | 88 | 100.0 | blastp |
| 290 | 779 | 914 | b_rapa | 329 | 94 | 100.0 | blastp |
| 291 | 780 | 915 | canola | 329 | 88 | 100.0 | blastp |
| 292 | 781 | 916 | canola | 329 | 94 | 100.0 | blastp |
| 293 | 782 | 917 | radish | 329 | 88 | 54.1 | blastp |
| 294 | 783 | 918 | thellungiella | 329 | 93 | 88.1 | blastp |
| 295 | 784 | 919 | b_rapa | 354 | 91 | 100.0 | blastp |
| 296 | 785 | 920 | canola | 354 | 89 | 67.7 | blastp |

Table 18.

Example 6

Improved Transgenic Plant Performance

To analyze whether the transgenic plants has performed better, plants were grown in pots with an adequate amount of nutrient and water. The plants were analyzed for their overall size, growth rate, time to inflorescence emergence (bolting) and flowering, seed yield, oil content of seed, weight of 1,000 seeds, dry matter and harvest index (HI—seed yield/dry matter). Transgenic plants performance was compared to control plants grown in parallel under the same conditions. Mock-transgenic plants expressing the uidA reporter gene (GUS-Intron) under the same promoter were used as control.

Parameters were measured as described in Examples 1 and 2.

Statistical analyses—To identify genes conferring significantly improved plant performance, the results obtained from the transgenic plants were compared to those obtained from control plants. Plant growth rate, plant area, time to bolt, time to flower, weight of 1,000 seeds, seed yield, oil yield, dry matter, and harvest index area data were analyzed using one-way ANOVA. To identify outperforming genes and constructs, results from mix of transformation events or independent events tested were analyzed. For gene versus control analysis T-test was applied, using significance of $p<0.05$. The JMP statistics software package was used (Version 5.2.1, SAS Institute Inc., Cary, N.C., USA).

Experimental Results

The polynucleotide sequences of the invention were assayed for a number of commercially desired traits.

Tables 19-24 depict analyses of seed yield in plants overexpressing the polynucleotides of the invention under the regulation of a constitutive (35S) or seed specific (napin) promoter. Each Table represents an independent experiment, using at least 5 independent events per gene. Genes not connected by same letter as the control (A, B,) are significantly different from the control.

TABLE 19

Genes showing improved plant performance: Seed yield

| | | | Seed yield per plant (gr) | | |
|---|---|---|---|---|---|
| Gene Id | SEQ ID NO: of overexpressed polynucleotide | Under regulation of | Least Sq Mean | Significance (t-Test compare to control) | % improvement |
| BDL8 | 1021 | 35S | 0.264 | A | 15.9 |
| BDL25 | 1032 | 35S | 0.239 | B | 5.2 |
| BDL27 | 1035 | 35S | 0.238 | B | 4.8 |
| BDL29 | 1037 | 35S | 0.235 | B | 3.4 |
| BDL32a | 1038 | 35S | 0.228 | B | 0.4 |
| CONTROL (GUS_Intron) | 1049 | 35S | 0.228 | B | 0.0 |

Table 19.

TABLE 20

Genes showing improved plant performance: Seed yield

| Gene Id | SEQ ID NO: of over-expressed polynucleotide | Under regulation of | Seed yield per plant (gr) | | |
|---|---|---|---|---|---|
| | | | Least Sq Mean | Significance (t-Test compare to control) | % improvement |
| BDL3 | 1017 | 35S | 0.447 | A | 10.9 |
| BDL11 | 1042 | 35S | 0.420 | A | 4.2 |
| BDL17 | 1043 | 35S | 0.426 | A | 5.8 |
| CONTROL (GUS_Intron) | 1049 | 35S | 0.403 | A | 0.0 |

Table 20.

TABLE 21

Genes showing improved plant performance: Seed yield

| Gene Id | SEQ ID NO: of over-expressed polynucleotide | Under regulation of | Seed yield per plant (gr) | | |
|---|---|---|---|---|---|
| | | | Least Sq Mean | Significance (t-Test compare to control) | % improvement |
| BDL3 | 1017 | Napin | 0.492 | A | 13.4 |
| BDL6 | 1019 | Napin | 0.469 | B | 8.1 |
| BDL28 | 1036 | Napin | 0.470 | B | 8.3 |
| CONTROL (GUS_Intron) | 1049 | Napin | 0.434 | B | 0.0 |

Table 21.

TABLE 22

Genes showing improved plant performance: Seed yield

| Gene Id | SEQ ID NO: of over-expressed polynucleotide | Under regulation of | Seed yield per plant (gr) | | |
|---|---|---|---|---|---|
| | | | Least Sq Mean | Significance (t-Test compare to control) | % improvement |
| BDL1 | 1040 | 35S | 0.359 | A | 23.5 |
| BDL12 | 1023 | 35S | 0.319 | B | 9.7 |
| BDL14 | 1024 | 35S | 0.378 | A | 30.3 |
| BDL18 | 1027 | 35S | 0.334 | B | 15.0 |
| BDL20a | 1029 | 35S | 0.325 | B | 12.0 |
| BDL20b | 1044 | 35S | 0.323 | B | 11.4 |
| BDL26a | 1033 | 35S | 0.340 | B | 17.0 |
| BDL26b | 1034 | 35S | 0.318 | B | 9.7 |
| BDL30 | 1046 | 35S | 0.340 | B | 17.2 |
| CONTROL (GUS_Intron) | 1049 | 35S | 0.290 | B | 0.0 |

Table 22.

TABLE 23

Genes showing improved plant performance: Seed yield

| Gene Id | SEQ ID NO: of over-expressed polynucleotide | Under regulation of | Seed yield per plant (gr) | | |
|---|---|---|---|---|---|
| | | | Least Sq Mean | Significance (t-Test compare to control) | % improvement |
| BDL9 | 1022 | 35S | 0.312 | B | 10.1 |
| BDL27 | 1035 | 35S | 0.320 | A | 13.0 |
| BDL32b | 1039 | 35S | 0.334 | A | 17.8 |
| CONTROL (GUS_Intron) | 1049 | 35S | 0.283 | B | 0.0 |

Table 23.

TABLE 24

Genes showing improved plant performance: Seed yield

| Gene Id | SEQ ID NO: of over-expressed polynucleotide | Under regulation of | Seed yield per plant (gr) | | |
|---|---|---|---|---|---|
| | | | Least Sq Mean | Significance (t-Test compare to control) | % improvement |
| BDL25 | 1032 | Napin | 0.41 | B | 0.1 |
| BDL29 | 1037 | Napin | 0.44 | B | 8.3 |
| BDL32b | 1039 | Napin | 0.46 | A | 13.0 |
| CONTROL (GUS_Intron) | 1049 | Napin | 0.41 | B | 0.0 |

Table 24.

Tables 25-30 depict analyses of oil yield in plants overexpressing the polynucleotides of the invention under the regulation of a constitutive (35S) or seed specific (napin) promoter. Each Table represents an independent experiment, using at least 5 independent events per gene. Genes not connected by same letter as the control (A, B,) are significantly different from the control.

TABLE 25

Genes showing improved plant performance: Oil yield

| Gene Id | SEQ ID NO: of over-expressed polynucleotide | Under regulation of | Oil yield per plant (gr) | | |
|---|---|---|---|---|---|
| | | | Least Sq Mean | Significance (t-Test compare to control) | % improvement |
| BDL8 | 1021 | 35S | 0.080 | A | 17.1 |
| BDL25 | 1032 | 35S | 0.074 | B | 8.3 |
| BDL27 | 1035 | 35S | 0.070 | B | 2.1 |
| BDL32a | 1038 | 35S | 0.069 | B | 1.1 |
| CONTROL (GUS Intron) | 1049 | 35S | 0.069 | B | 0.0 |

Table 25,

TABLE 26

Genes showing improved plant performance: Oil yield

| Gene Id | SEQ ID NO: of over-expressed poly-nucleotide | Under regula-tion of | Least Sq Mean | Significance (t-Test compare to control) | % im-prove-ment |
|---|---|---|---|---|---|
| BDL3 | 1017 | 35S | 0.13 | A | 13.7 |
| BDL11 | 1042 | 35S | 0.12 | A | 7.0 |
| BDL17 | 1043 | 35S | 0.12 | A | 6.5 |
| CONTROL (GUS_Intron) | 1049 | 35S | 0.12 | A | 0.0 |

Table 26,

TABLE 27

Genes showing improved plant performance: Oil yield

| Gene Id | SEQ ID NO: of over-expressed poly-nucleotide | Under regula-tion of | Least Sq Mean | Significance (t-Test compare to control) | % im-prove-ment |
|---|---|---|---|---|---|
| BDL3 | 1017 | Napin | 0.149 | A | 13.7 |
| BDL6 | 1019 | Napin | 0.143 | B | 9.2 |
| BDL28 | 1036 | Napin | 0.138 | B | 5.3 |
| CONTROL (GUS_Intron) | 1049 | Napin | 0.131 | B | 0.0 |

Table 27,

TABLE 28

Genes showing improved plant performance: Oil yield

| Gene Id | SEQ ID NO: of over-expressed poly-nucleotide | Under regula-tion of | Least Sq Mean | Significance (t-Test compare to control) | % im-prove-ment |
|---|---|---|---|---|---|
| BDL1 | 1040 | 35S | 0.108 | A* | 23.7 |
| BDL12 | 1023 | 35S | 0.100 | B | 14.2 |
| BDL14 | 1024 | 35S | 0.114 | A | 31.1 |
| BDL18 | 1027 | 35S | 0.102 | B | 16.7 |
| BDL20a | 1029 | 35S | 0.098 | B | 12.0 |
| BDL20b | 1044 | 35S | 0.098 | B | 12.1 |
| BDL26a | 1033 | 35S | 0.103 | B | 18.0 |
| BDL26b | 1034 | 35S | 0.097 | B | 11.8 |
| BDL30 | 1046 | 35S | 0.107 | B | 22.4 |
| CONTROL (GUS_Intron) | 1049 | 35S | 0.087 | B | 0.0 |

Table 28,
*P = 0.07

TABLE 29

Genes showing improved plant performance: Oil yield

| Gene Id | SEQ ID NO: of over-expressed poly-nucleotide | Under regula-tion of | Least Sq Mean | Significance (t-Test compare to control) | % im-prove-ment |
|---|---|---|---|---|---|
| BDL9 | 1022 | 35S | 0.092 | B | 6.2 |
| BDL27 | 1035 | 35S | 0.095 | B | 9.1 |
| BDL32b | 1039 | 35S | 0.101 | A | 16.4 |
| CONTROL (GUS_Intron) | 1049 | 35S | 0.087 | B | 0.0 |

Table 29,

TABLE 30

Genes showing improved plant performance: Oil yield

| Gene Id | SEQ ID NO: of over-expressed poly-nucleotide | Under regula-tion of | Least Sq Mean | Significance (t-Test compare to control) | % im-prove-ment |
|---|---|---|---|---|---|
| BDL25 | 1032 | Napin | 0.12 | B | 2.2 |
| BDL29 | 1037 | Napin | 0.14 | A | 15.8 |
| BDL32b | 1039 | Napin | 0.15 | A | 20.6 |
| CONTROL (GUS_Intron) | 1049 | Napin | 0.12 | B | 0.0 |

Table 30,

Tables 31-32 depict analyses of dry matter in plants overexpressing the polynucleotides of the invention under the regulation of a constitutive (35S). Each Table represents an independent experiment, using at least 5 independent events per gene. Genes not connected by same letter as the control (A, B,) are significantly different from the control.

TABLE 31

Genes showing improved plant performance: Dry matter

| Gene Id | SEQ ID NO: of over-expressed poly-nucleotide | Under regula-tion of | Least Sq Mean | Significance (t-Test compare to control) | % im-prove-ment |
|---|---|---|---|---|---|
| BDL6 | 1019 | 35S | 1.0277 | A | 7.9 |
| BDL14 | 1024 | 35S | 1.0444 | A | 9.7 |
| BDL18 | 1027 | 35S | 0.985 | A | 3.4 |
| BDL20b | 1044 | 35S | 1.0656 | A | 11.9 |
| CONTROL (GUS_Intron) | 1049 | 35S | 0.9523 | A | 0.0 |

Table 31.

TABLE 32

Genes showing improved plant performance: Dry matter

| | | | Dry matter per plant (gr) | |
|---|---|---|---|---|
| Gene Id | SEQ ID NO: of over-expressed poly-nucleotide | Under regula-tion of | Least Sq Mean | Significance (t-Test compare to control) | % im-prove-ment |
| BDL3 | 1017 | 35S | 1.3915 | A | 3.3 |
| BDL11 | 1042 | 35S | 1.3638 | A | 1.2 |
| CONTROL (GUS_Intron) | 1049 | 35S | 1.3474 | A | 0.0 |

Table 32.

Tables 33-34 depict analyses of harvest index (HI) in plants overexpressing the polynucleotides of the invention under the regulation of a constitutive (35S) or seed specific (napin) promoter. Each Table represents an independent experiment, using at least 5 independent events per gene. Genes not connected by same letter as the control (A, B,) are significantly different from the control.

TABLE 33

Genes showing improved plant performance: harvest index (HI)

| | | | HI | |
|---|---|---|---|---|
| Gene Id | SEQ ID NO: of over-expressed poly-nucleotide | Under regula-tion of | Least Sq Mean | Significance (t-Test compare to control) | % im-prove-ment |
| BDL3 | 1017 | 35S | 0.3218 | B | 7.2 |
| BDL5 | 1018 | 35S | 0.3094 | B | 3.0 |
| BDL8 | 1021 | 35S | 0.3301 | B | 9.9 |
| BDL11 | 1042 | 35S | 0.3063 | B | 2.0 |
| BDL17 | 1043 | 35S | 0.3526 | A | 17.5 |
| BDL25 | 1032 | 35S | 0.3016 | B | 0.4 |
| CONTROL (GUS_Intron) | 1049 | 35S | 0.3002 | B | 0.0 |

Table 33

TABLE 34

Genes showing improved plant performance: harvest index (HI)

| | | | HI | |
|---|---|---|---|---|
| Gene Id | SEQ ID NO: of over-expressed poly-nucleotide | Under regula-tion of | Least Sq Mean | Significance (t-Test compare to control) | % im-prove-ment |
| BDL2 | 1016 | Napin | 0.342 | B | 3.7 |
| BDL3 | 1017 | Napin | 0.358 | B | 8.8 |
| BDL6 | 1019 | Napin | 0.365 | B | 10.9 |
| BDL28 | 1036 | Napin | 0.374 | A | 13.6 |
| CONTROL (GUS_Intron) | 1049 | Napin | 0.329 | B | 0.0 |

Table 34

Tables 35-38 depict analyses of growth rate in plants overexpressing the polynucleotides of the invention under the regulation of a constitutive (35S). Each Table represents an independent experiment, using at least 5 independent events per gene. Genes not connected by same letter as the control (A, B,) are significantly different from the control.

TABLE 35

Genes showing improved plant performance: Growth rate

| | | | Growth rate (cm²/day) | |
|---|---|---|---|---|
| Gene Id | SEQ ID NO: of over-expressed poly-nucleotide | Under regula-tion of | Least Sq Mean | Significance (t-Test compare to control) | % im-prove-ment |
| BDL14 | 1024 | 35S | 2.48 | A | 6.4 |
| BDL18 | 1027 | 35S | 2.41 | A | 3.5 |
| BDL20a | 1029 | 35S | 2.50 | A | 7.1 |
| CONTROL (GUS_Intron) | 1049 | 35S | 2.33 | A | 0.0 |

Table 35,

TABLE 36

Genes showing improved plant performance: Growth rate

| | | | Growth rate (cm²/day) | |
|---|---|---|---|---|
| Gene Id | SEQ ID NO: of over-expressed poly-nucleotide | Under regula-tion of | Least Sq Mean | Significance (t-Test compare to control) | % im-prove-ment |
| BDL11 | 1042 | 35S | 1.80 | A | 15.4 |
| CONTROL (GUS_Intron) | 1049 | 35S | 1.56 | A | 0.0 |

Table 36,

TABLE 37

Genes showing improved plant performance: Growth rate

| | | | Growth rate (cm²/day) | |
|---|---|---|---|---|
| Gene Id | SEQ ID NO: of over-expressed poly-nucleotide | Under regula-tion of | Least Sq Mean | Significance (t-Test compare to control) | % im-prove-ment |
| BDL1 | 1040 | 35S | 1.81 | A* | 17.1 |
| BDL12 | 1023 | 35S | 1.58 | B | 2.0 |
| BDL14 | 1024 | 35S | 1.95 | A | 26.3 |
| BDL18 | 1027 | 35S | 1.59 | B | 3.1 |
| BDL20b | 1044 | 35S | 1.77 | B | 14.6 |
| BDL26a | 1033 | 35S | 1.57 | B | 1.9 |
| BDL30 | 1046 | 35S | 1.75 | B | 13.0 |
| CONTROL (GUS_Intron) | 1049 | 35S | 1.55 | B | 0.0 |

Table 37,
*P = 0.06

TABLE 38

Genes showing improved plant performance: Growth rate

| | | | Growth rate (cm²/day) | |
|---|---|---|---|---|
| Gene Id | SEQ ID NO: of over-expressed poly-nucleotide | Under regula-tion of | Least Sq Mean | Significance (t-Test compare to control) | % im-prove-ment |
| BDL32b | 1039 | 35S | 1.19 | A | 0.8 |
| CONTROL (GUS_Intron) | 1049 | 35S | 1.18 | A | 0.0 |

Table 38.

Tables 39-42 depict analyses of rosette area in plants overexpressing the polynucleotides of the invention under the regulation of a constitutive (35S) or seed specific (napin) promoter. Each Table represents an independent experiment, using at least 5 independent events per gene. Genes not connected by same letter as the control (A, B,) are significantly different from the control.

TABLE 39

Genes showing improved plant performance: Rossete area

| Gene Id | SEQ ID NO: of over-expressed poly-nucleotide | Under regula-tion of | Rosette area (cm²) Least Sq Mean | Signif-icance (t-Test compare to control) | % im-prove-ment |
|---|---|---|---|---|---|
| BDL6 | 1019 | 35S | 9.73 | A | −10.2 |
| BDL7 | 1020 | 35S | 8.52 | A | −21.4 |
| BDL14 | 1024 | 35S | 11.83 | A | 9.2 |
| BDL18 | 1027 | 35S | 11.62 | A | 7.3 |
| BDL20a | 1029 | 35S | 11.90 | A | 9.9 |
| BDL20b | 1044 | 35S | 11.02 | B | 1.7 |
| BDL24 | 1045 | 35S | 8.12 | A | −25.1 |
| CONTROL (GUS_Intron) | 1049 | 35S | 10.83 | B | 0.0 |

Table 39: Increase in rosette area means better soil coverage and reduced water loss from soil. Decrease in rosette area means more plants could be put per area increasing yield.

TABLE 40

Genes showing improved plant performance: Rossete area

| Gene Id | SEQ ID NO: of over-expressed poly-nucleotide | Under regula-tion of | Rosette area (cm²) Least Sq Mean | Signif-icance (t-Test compare to control) | % im-prove-ment |
|---|---|---|---|---|---|
| BDL3 | 1017 | 35S | 11.99 | A | −3.6 |
| BDL5 | 1018 | 35S | 11.36 | A | −8.6 |
| BDL8 | 1021 | 35S | 9.31 | B | −25.1 |
| BDL11 | 1042 | 35S | 14.09 | A | 13.2 |
| BDL16 | 1026 | 35S | 10.91 | A | −12.3 |
| BDL17 | 1043 | 35S | 9.97 | B | −19.9 |
| BDL25 | 1032 | 35S | 7.95 | B | −36.1 |
| CONTROL (GUS_Intron) | 1049 | 35S | 12.44 | A | 0.0 |

Table 40: Increase in rosette area means better soil coverage and reduced water loss from soil. Decrease in rosette area means more plants could be put per area increasing yield.

TABLE 41

Genes showing improved plant performance: Rossete area

| Gene Id | SEQ ID NO: of over-expressed poly-nucleotide | Under regula-tion of | Rosette area (cm²) Least Sq Mean | Signif-icance (t-Test compare to control) | % im-prove-ment |
|---|---|---|---|---|---|
| BDL1 | 1040 | 35S | 9.13 | B | 12.4 |
| BDL12 | 1023 | 35S | 7.92 | B | −2.5 |
| BDL14 | 1024 | 35S | 9.96 | A | 22.7 |
| BDL18 | 1027 | 35S | 8.63 | B | 6.3 |
| BDL20a | 1029 | 35S | 8.03 | B | −1.1 |
| BDL20b | 1044 | 35S | 9.14 | B | 12.6 |
| BDL26a | 1033 | 35S | 8.51 | B | 4.8 |
| BDL26b | 1034 | 35S | 7.92 | B | −2.5 |
| BDL30 | 1046 | 35S | 9.28 | A | 14.2 |
| CONTROL (GUS_Intron) | 1049 | 35S | 8.12 | B | 0.0 |

Table 41: Increase in rosette area means better soil coverage and reduced water loss from soil. Decrease in rosette area means more plants could be put per area increasing yield.

TABLE 42

Genes showing improved plant performance: Rossete area

| Gene Id | SEQ ID NO: of over-expressed poly-nucleotide | Under regula-tion of | Rosette area (cm²) Least Sq Mean | Signif-icance (t-Test compare to control) | % im-prove-ment |
|---|---|---|---|---|---|
| BDL9 | 1022 | 35S | 5.05 | B | −17.0 |
| BDL21 | 1030 | 35S | 4.77 | B | −21.5 |
| BDL27 | 1035 | 35S | 5.22 | B | −14.2 |
| BDL32b | 1039 | 35S | 6.19 | A | 1.8 |
| CONTROL (GUS_Intron) | 1049 | 35S | 6.08 | A | 0.0 |

Table 42: Increase in rosette area means better soil coverage and reduced water loss from soil. Decrease in rosette area means more plants could be put per area increasing yield.

Tables 43-49 depict analyses of oil % in seed in plants overexpressing the polynucleotides of the invention under the regulation of a constitutive (35S) or seed specific (napin) promoter. Each Table represents an independent experiment, using at least 5 independent events per gene. Genes not connected by same letter as the control (A, B,) are significantly different from the control.

TABLE 43

Genes showing improved plant performance: oil % in seed

| Gene Id | SEQ ID NO: of over-expressed poly-nucleotide | Under regula-tion of | Oil % in seed Least Sq Mean | Signif-icance (t-Test compare to control) | % im-prove-ment |
|---|---|---|---|---|---|
| BDL8 | 1021 | 35S | 30.542 | A | 1.1 |
| BDL25 | 1032 | 35S | 31.09 | A | 2.9 |
| BDL32a | 1038 | 35S | 30.264 | A | 0.2 |
| CONTROL (GUS_Intron) | 1049 | 35S | 30.21 | A | 0.0 |

Table 43.

TABLE 44

Genes showing improved plant performance: oil % in seed

| Gene Id | SEQ ID NO: of over-expressed poly-nucleotide | Under regula-tion of | Oil % in seed | | |
|---|---|---|---|---|---|
| | | | Least Sq Mean | Significance (t-Test compare to control) | % improvement |
| BDL6 | 1019 | 35S | 30.565 | B | 0.7 |
| BDL14 | 1024 | 35S | 31.31 | B | 3.1 |
| BDL18 | 1027 | 35S | 30.56 | B | 0.7 |
| BDL20a | 1029 | 35S | 31.393 | B | 3.4 |
| BDL20b | 1044 | 35S | 31.928 | A | 5.2 |
| BDL24 | 1045 | 35S | 31.02 | B | 2.2 |
| CONTROL (GUS_Intron) | 1049 | 35S | 30.355 | B | 0.0 |

Table 44.

TABLE 45

Genes showing improved plant performance: oil % in seed

| Gene Id | SEQ ID NO: of over-expressed poly-nucleotide | Under regula-tion of | Oil % in seed | | |
|---|---|---|---|---|---|
| | | | Least Sq Mean | Significance (t-Test compare to control) | % improvement |
| BDL3 | 1017 | 35S | 29.39 | A | 2.1 |
| BDL5 | 1018 | 35S | 29.29 | A | 1.8 |
| BDL8 | 1021 | 35S | 28.903 | A | 0.4 |
| BDL11 | 1042 | 35S | 29.216 | A | 1.5 |
| BDL17 | 1043 | 35S | 28.904 | A | 0.4 |
| BDL25 | 1032 | 35S | 29.514 | A | 2.6 |
| CONTROL (GUS_Intron) | 1049 | 35S | 28.78 | A | 0 |

Table 45.

TABLE 46

Genes showing improved plant performance: oil % in seed

| Gene Id | SEQ ID NO: of over-expressed poly-nucleotide | Under regula-tion of | Oil % in seed | | |
|---|---|---|---|---|---|
| | | | Least Sq Mean | Significance (t-Test compare to control) | % improvement |
| BDL3 | 1017 | Napin | 30.34 | A | 0.46 |
| BDL6 | 1019 | Napin | 30.45 | A | 0.83 |
| BDL28 | 1036 | Napin | 29.49 | A | 2.35 |
| CONTROL (GUS_Intron) | 1049 | Napin | 30.2 | A | 0 |

Table 46.

TABLE 47

Genes showing improved plant performance: oil % in seed

| Gene Id | SEQ ID NO: of over-expressed poly-nucleotide | Under regula-tion of | Oil % in seed | | |
|---|---|---|---|---|---|
| | | | Least Sq Mean | Significance (t-Test compare to control) | % improvement |
| BDL12 | 1023 | 35S | 31.30 | A | 3.7 |
| BDL14 | 1024 | 35S | 30.27 | A | 0.3 |
| BDL18 | 1027 | 35S | 30.39 | A | 0.7 |
| BDL26a | 1033 | 35S | 30.33 | A | 0.5 |
| BDL26b | 1034 | 35S | 30.43 | A | 0.8 |
| BDL30 | 1046 | 35S | 31.42 | A | 4.1 |
| CONTROL (GUS_Intron) | 1049 | 35S | 30.19 | A | 0.0 |

Table 47.

TABLE 48

Genes showing improved plant performance: oil % in seed

| Gene Id | SEQ ID NO: of over-expressed poly-nucleotide | Under regula-tion of | Oil % in seed | | |
|---|---|---|---|---|---|
| | | | Least Sq Mean | Significance (t-Test compare to control) | % improvement |
| BDL21 | 1030 | 35S | 30.55 | A | 1.8 |
| BDL32b | 1039 | 35S | 30.35 | A | 1.1 |
| CONTROL (GUS_Intron) | 1049 | 35S | 30.01 | A | 0.0 |

Table 48.

TABLE 49

Genes showing improved plant performance: oil % in seed

| Gene Id | SEQ ID NO: of over-expressed poly-nucleotide | Under regula-tion of | Oil % in seed | | |
|---|---|---|---|---|---|
| | | | Least Sq Mean | Significance (t-Test compare to control) | % improvement |
| BDL25 | 1032 | Napin | 30.34 | B | 1.5 |
| BDL29 | 1037 | Napin | 31.54 | A | 5.5 |
| BDL32b | 1039 | Napin | 31.69 | A | 6.0 |
| CONTROL (GUS_Intron) | 1049 | Napin | 29.90 | B | 0.0 |

Table 49.

Tables 50-55 depict analyses of weight of 1000 seeds in plants overexpressing the polynucleotides of the invention under the regulation of a constitutive (35S) or seed specific (napin) promoter. Each Table represents an independent experiment, using at least 5 independent events per gene. Genes not connected by same letter as the control (A, B,) are significantly different from the control.

TABLE 50

Genes showing improved plant performance: weight of 1,000 seeds

| | | Weight of 1000 seeds (gr) | | | |
|---|---|---|---|---|---|
| Gene Id | SEQ ID NO: of over-expressed polynucleotide | Under regulation of | Least Sq Mean | Significance (t-Test compare to control) | % improvement |
| BDL8 | 1021 | 35S | 0.019 | B | 9.1 |
| BDL21 | 1030 | 35S | 0.018 | B | 0.3 |
| BDL25 | 1032 | 35S | 0.018 | B | 0.4 |
| BDL32a | 1038 | 35S | 0.019 | B | 5.5 |
| BDL32b | 1039 | 35S | 0.020 | A | 14.2 |
| CONTROL (GUS_Intron) | 1049 | 35S | 0.018 | B | 0.0 |

Table 50.

TABLE 51

Genes showing improved plant performance: weight of 1,000 seeds

| | | Weight of 1000 seeds (gr) | | | |
|---|---|---|---|---|---|
| Gene Id | SEQ ID NO: of over-expressed polynucleotide | Under regulation of | Least Sq Mean | Significance (t-Test compare to control) | % improvement |
| BDL6 | 1019 | 35S | 0.019 | B | 7.1 |
| BDL7 | 1020 | 35S | 0.018 | B | 3.8 |
| BDL14 | 1024 | 35S | 0.019 | B | 6.1 |
| BDL18 | 1027 | 35S | 0.019 | B | 8.2 |
| BDL20b | 1044 | 35S | 0.020 | A | 14.5 |
| BDL24 | 1045 | 35S | 0.018 | B | 4.5 |
| CONTROL (GUS_Intron) | 1049 | 35S | 0.018 | B | 0.0 |

Table 51.

TABLE 52

Genes showing improved plant performance: weight of 1,000 seeds

| | | Weight of 1000 seeds (gr) | | | |
|---|---|---|---|---|---|
| Gene Id | SEQ ID NO: of over-expressed polynucleotide | Under regulation of | Least Sq Mean | Significance (t-Test compare to control) | % improvement |
| BDL3 | 1017 | 35S | 0.0214 | B | 5.8 |
| BDL5 | 1018 | 35S | 0.0205 | B | 1.1 |
| BDL11 | 1042 | 35S | 0.0235 | A | 15.7 |
| CONTROL (GUS_Intron) | 1049 | 35S | 0.0203 | B | 0 |

Table 52.

TABLE 53

Genes showing improved plant performance: weight of 1,000 seeds

| | | Weight of 1000 seeds (gr) | | | |
|---|---|---|---|---|---|
| Gene Id | SEQ ID NO: of over-expressed polynucleotide | Under regulation of | Least Sq Mean | Significance (t-Test compare to control) | % improvement |
| BDL2 | 1016 | Napin | 0.0290 | A | 30.7 |
| BDL6 | 1019 | Napin | 0.0232 | B | 4.3 |
| BDL14 | 1024 | Napin | 0.0227 | B | 2.3 |
| BDL28 | 1036 | Napin | 0.0224 | B | 1.0 |
| CONTROL (GUS_Intron) | 1049 | Napin | 0.0222 | B | 0.0 |

Table 53.

TABLE 54

Genes showing improved plant performance: weight of 1,000 seeds

| | | Weight of 1000 seeds (gr) | | | |
|---|---|---|---|---|---|
| Gene Id | SEQ ID NO: of over-expressed polynucleotide | Under regulation of | Least Sq Mean | Significance (t-Test compare to control) | % improvement |
| BDL1 | 1040 | 35S | 0.0235 | B | 0.6 |
| BDL12 | 1023 | 35S | 0.0234 | B | 0.1 |
| BDL30 | 1046 | 35S | 0.0252 | A | 7.8 |
| CONTROL (GUS_Intron) | 1049 | 35S | 0.0234 | B | 0.0 |

Table 54.

TABLE 55

Genes showing improved plant performance: weight of 1,000 seeds

| | | Weight of 1000 seeds (gr) | | | |
|---|---|---|---|---|---|
| Gene Id | SEQ ID NO: of over-expressed polynucleotide | Under regulation of | Least Sq Mean | Significance (t-Test compare to control) | % improvement |
| BDL12 | 1023 | Napin | 0.0206 | B | 0.2 |
| BDL18 | 1027 | Napin | 0.0214 | B | 4.0 |
| BDL25 | 1032 | Napin | 0.0208 | B | 1.1 |
| BDL27 | 1035 | Napin | 0.0211 | B | 2.8 |
| BDL29 | 1037 | Napin | 0.0211 | B | 2.6 |
| BDL32b | 1039 | Napin | 0.0224 | A | 9.3 |
| CONTROL (GUS_Intron) | 1049 | Napin | 0.0205 | B | 0.0 |

Table 55.

Taking into account the results obtained using these assays, the following BDL genes, when exogenously introduced into plants, induced a significant improvement in:

1. Seed yield: BDL1, BDL3, BDL8, BDL14, BDL27, BDL32b.
2. Oil yield: BDL1, BDL3, BDL8, BDL14, BDL29, BDL32b.
3. Harvest Index: BDL17, BDL28.
4. Growth rate: BDL1, BDL14.
5. Roseate area: BDL14, BDL18, BDL20a, BDL30.
6. Oil % in seed: BDL20b, BDL29, BDL32b.
7. Weight of 1000 Seeds: BDL2, BDL11, BDL20b, BDL30, BDL32b

Example 7

Increased Oil Content in Leaves

In general, oil is composed mainly of tri acyl glycerols (TAG). Seeds of *Arabidopsis* and other oilseed contain high amounts of TAG. Usually the TAGs are being degraded into sugars through the germination process. Cermac and Benning (*Plant journal* 2004; 40, 575-585) in their paper used an assay to quantify TAG production in seedlings grown on sucrose. They used this stage of development since normally seedlings not present TAG in high levels. In their study, they demonstrated the importance of the wrinkled gene in the control of oil production by showing that transgenic seedlings overexpressing the wrinkled cDNA produce high amounts of TAG.

Materials and Experimental Methods

The present inventors used the assay of Cermac and Benning assay (Cermac and Benning, *Plant journal* 2004; 40, 575-585) with minor changes to qualify the effect of the transgenes identified herein for their ability to increase TAG in seedlings, similar to the wrinkled gene.

For triacylglycerol quantification $T_2$ transgenic seedlings were grown on ½ MS medium (Murashige and Skoog, 1962 Plant Physiology 15, 473-497), pH 5.9, 2% sucrose and 0.7% agar. Seeds were sterilized by evaporating of 100 ml bleach (10%) and 4 ml HCl (37%) for 90 minutes in close plastic chamber of 5.5 L vol. Glufosinate-ammonium and kanamaycin were added to final concentrations of 20 µg ml$^{-1}$ for glufosinate-ammonium and 50 µg ml$^{-1}$ kanamaycin. Follow sterilization, seeds were sown on agar plates. Plates were incubated for 3 days in the dark at 4° C. before placing them in a growth room. The conditions at the growth room were of 24° C., light period of 12 hour and a dark period of 12 hour. Seedlings were grown for 10-11 days.

Equal amount of 11 days old seedlings were ground in 1.5-mL polypropylene test tubes with a glass rod, and lipids were extracted in 50 mL of chloroform:methanol: formic acid (10:10:1, v/v). Following the extraction with 12.5 mL of 1 M KCl and 0.2 M $H_3PO_4$ and separation of the organic and aqueous phases by centrifugation at 16,000 g for 5 minutes, the lipids in the lower phase were separated on a silica TLC plate (Si 250 PA, J. T. Baker, Philipsburg, N.J.) developed with 80:20:1, petroleum ether:ethyl ether:acetic acid. Lipids were visualized by staining with iodine vapor.

As positive controls the following were used: The naturally produced TriAcyl Glycerols—extracted from seeds of wild-type *arabidopsis* (lane 5, FIG. 3); and transgenic seedlings expressing WRINKLED cDNA (SEQ ID NO:1050), which are known to produce significant amounts of TriAcyl Glycerols in leaves (Cernac A and Benning C, The *Plant Journal* 2004, 40, 575-585). As negative controls the transgenic seedlings expressing GUS-Intron gene (SEQ ID NO:1049) were used.

Experimental Results

FIG. 3 depicts iodine vapor staining of lipids isolated from the transgenic plants of independent events (BDL9, WRINKLED) or pool of events (GUS-Intron) expressing the following genes according to Table 56, hereinbelow. An independent Event represents a single stable transformed plant that resulted from random integration of the transformed construct in the *Arabidopsis* genome. Progenies of an event harboring the transformed construct were used for the gene evaluation separately as in the case of BDL9 and Wrinkeld genes or as pool of events in case of GUS-Intron.

TABLE 56

| Lane No. | Description of plant transformation | Name of upregulated gene or control plant |
|---|---|---|
| 1 | Transformed with SEQ ID NO: 1022 | BDL9 Event 1 |
| 2 | Transformed with SEQ ID NO: 1022 | BDL9 Event 2 |
| 3 | Transformed with SEQ ID NO: 1022 | BDL9 Event 3 |
| 4 | Transformed plant with control vector SEQ ID NO: 1049 | GUS-Intron |
| 5 | Untransformed plant | SEED |
| 6 | Transformed with SEQ ID NO: 1050 | Wrinkled Event 1 |
| 7 | Transformed with SEQ ID NO: 1050 | Wrinkled Event 2 |
| 8 | Transformed with SEQ ID NO: 1050 | Wrinkled Event 3 |

Table 56.

As shown in FIG. 3, transgenic plants expressing the BDL9 gene (SEQ ID NO:1022) produce a significantly higher oil content as compared to the oil content produced by control plants expressing the GUS-intron (SEQ ID NO:1049). In addition, the amount of oil produced by the BDL9-transgenic plants (e.g., FIG. 3, lane 2) is comparable to that produced by seeds (FIG. 3, lane 5) or by transgenic plants expressing the known Wrinkled gene (FIG. 3, lane 6).

Summary

The present inventors have identified genes from *Arabidopsis thaliana*, which are important for embryogenesis, seed development and oil synthesis and accumulation. These genes, when over-expressed in plants, can effectively increase oil content in seeds or leaves or any other plant part. Tissue or embryonic specific expression of the genes in plants can result in optimal increase oil content in any plant tissue. Thus, the transgenes can be expressed in certain stages of embryo, seed development or to developmental stages of any target tissue, defined as the oil accumulating tissue. This unique expression profile can be achieved by using specific promoters, such as developmental promoters, seed expressing and seed specific promoters.

The present inventors demonstrated improvement of oil synthesis and accumulation by increasing seed size, which enabled the synthesized oil to be accumulated to larger extent, within a larger volume.

In addition, increase of oil can be achieved by controlling embryogenesis. Oil is accumulated in the embryo of developed seed. Some of the early embryo development genes are directly in charge of the regulation of oil synthesis and storage.

The identified genes of the invention can improve oil yield in general, and more specifically oil synthesis, oil accumulation and seed size. The output of the bioinformatics method described herein is a set of genes highly predicted to improve oil and seed yields by modifying their expression. Although each gene is predicted to have its own impact, modifying the mode of expression of more than one gene is expected to provide an additive or synergistic effect on the plant seed/oil yield performance. Altering the expression of each gene described here alone or set of genes together increases the overall oil yield, hence expects to decrease vegetable oil price, as well as to increase productivity.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09487793B2). An electronic copy of the "Sequence Listing" will also be available from the USPTO upon request and payment of the fee set forth in 37 CFR 1.19(b)(3).

What is claimed is:

1. A method of increasing oil content and/or seed yield of a plant, comprising:
   (a) introducing into the plant an exogenous polynucleotide encoding the polypeptide set forth by SEQ ID NO: 329 or a homologous polypeptide which comprises conservative amino acid substitution(s) with respect to the amino acid sequence set forth by SEQ ID NO: 329, and which exhibits at least 93% sequence identity to the amino acid sequence set forth by SEQ ID NO: 329, and;
   (b) selecting plants resultant of step (a) for increased oil content and/or increased seed yield as compared to a non-transformed plant of the same species which is grown under the same growth conditions,
   thereby increasing the oil content and/or the seed yield of the plant.

2. A method of producing oil, comprising:
   (a) providing the plant according to claim 1; and
   (b) extracting the oil from the plant;
   thereby producing the oil.

3. The method of claim 1, wherein said exogenous polynucleotide comprises the nucleic acid sequence set forth by SEQ ID NO: 164 or a codon optimized nucleic acid sequence thereof.

4. The method of claim 1, wherein said amino acid sequence is selected from the group consisting of SEQ ID NOs: 329, 912, 914 and 916.

5. The method of claim 1, wherein said polynucleotide is selected from the group consisting of SEQ ID NOs: 164, 777, 781, and 779.

6. The method of claim 1, wherein said polypeptide is set forth by SEQ ID NO: 329.

7. The method of claim 1, wherein the oil comprises a seed oil.

8. The method of claim 1, wherein said polynucleotide comprises the nucleic acid sequence set forth by SEQ ID NO: 164.

9. A method of selecting a transformed plant having increased oil content and/or increased seed yield as compared to a non-transformed plant, the method comprising:
   (a) providing plants transformed with an exogenous polynucleotide encoding the polypeptide set forth by SEQ ID NO: 329 or a homologous polypeptide which comprises conservative amino acid substitution(s) with respect to the amino acid sequence set forth by SEQ ID NO: 329, and which exhibits at least 93% sequence identity to the amino acid sequence set forth by SEQ ID NO: 329,
   (b) selecting from said plants of step (a) a plant having increased oil content and/or increased seed yield as compared to a non-transformed plant of the same species which is grown under the same growth conditions,
   thereby selecting the plant having the increased oil content and/or the increased seed yield as compared to the non-transformed plant.

10. The method of claim 9, wherein said amino acid sequence is selected from the group consisting of SEQ ID NOs: 329, 912, 914 and 916.

11. The method of claim 9, wherein said exogenous polynucleotide encodes the polypeptide set forth by SEQ ID NO: 329.

12. The method of claim 9, wherein said exogenous polynucleotide comprises the nucleic acid sequence set forth by SEQ ID NO: 164 or a codon optimized sequence thereof.

13. The method of claim 9, wherein said exogenous polynucleotide comprises the nucleic acid sequence set forth by SEQ ID NO: 164.

14. A method of increasing oil content and/or seed yield of a plant, comprising:
   (a) introducing into the plant an exogenous polynucleotide encoding a polypeptide comprising the amino acid sequence set forth by SEQ ID NO: 329, and;
   (b) selecting plants resultant of step (a) for increased oil content and/or increased seed yield as compared to a non-transformed plant of the same species which is grown under the same growth conditions,
   thereby increasing the oil content and/or the seed yield of the plant.

15. A method of producing oil, comprising:
   (a) providing the plant according to claim 14; and
   (b) extracting the oil from the plant;
   thereby producing the oil.

16. A method of selecting a transformed plant having increased oil content and/or increased seed yield as compared to a non-transformed plant, the method comprising:
   (a) providing plants transformed with an exogenous polynucleotide encoding a polypeptide comprising the amino acid sequence set forth by SEQ ID NO: 329,
   (b) selecting from said plants of step (a) a plant having increased oil content and/or increased seed yield as compared to a non-transformed plant of the same species which is grown under the same growth conditions, thereby selecting the plant having the increased oil content and/or increased seed yield as compared to the non-transformed plant.

* * * * *